US009657013B2

(12) United States Patent
Cuconati et al.

(10) Patent No.: US 9,657,013 B2
(45) Date of Patent: May 23, 2017

(54) INHIBITORS OF HEPATITIS B VIRUS COVALENTLY CLOSED CIRCULAR DNA FORMATION AND THEIR METHOD OF USE

(71) Applicants: Baruch S. Blumberg Institute, Doylestown, PA (US); Drexel University, Philadelphia, PA (US)

(72) Inventors: Andrea Cuconati, Oreland, PA (US); Haitao Guo, Lansdale, PA (US); Timothy M. Block, Doylestown, PA (US); Ju-Tao Guo, Lansdale, PA (US); Xiaodong Xu, Doylestown, PA (US); Huagang Lu, Plainsboro, NJ (US); Dawei Cai, Doylestown, PA (US)

(73) Assignees: Baruch S. Blumberg Institute, Doylestown, PA (US); Drexel University, Philadelphia, PA (US)

( * ) Notice: Subject to any disclaimer, the term of this patent is extended or adjusted under 35 U.S.C. 154(b) by 0 days.

(21) Appl. No.: 14/382,074

(22) PCT Filed: Feb. 28, 2013

(86) PCT No.: PCT/US2013/028150
§ 371 (c)(1),
(2) Date: Aug. 29, 2014

(87) PCT Pub. No.: WO2013/130703
PCT Pub. Date: Sep. 6, 2013

(65) Prior Publication Data
US 2015/0038515 A1    Feb. 5, 2015

Related U.S. Application Data

(60) Provisional application No. 61/605,059, filed on Feb. 29, 2012, provisional application No. 61/605,071, filed on Feb. 29, 2012.

(51) Int. Cl.
| | | |
|---|---|---|
| *A61K 31/4409* | (2006.01) |
| *A61K 31/505* | (2006.01) |
| *A61K 31/4465* | (2006.01) |
| *A61K 31/445* | (2006.01) |
| *A61K 31/428* | (2006.01) |
| *A61K 31/165* | (2006.01) |
| *A61K 31/495* | (2006.01) |
| *C07D 471/04* | (2006.01) |
| *C07D 263/56* | (2006.01) |
| *C07D 213/76* | (2006.01) |
| *C07D 235/08* | (2006.01) |
| *C07D 401/12* | (2006.01) |
| *C07D 239/26* | (2006.01) |
| *C07D 209/08* | (2006.01) |
| *C07D 277/64* | (2006.01) |
| *C07D 211/26* | (2006.01) |
| *C07D 213/40* | (2006.01) |
| *C07C 311/21* | (2006.01) |
| *C07D 295/135* | (2006.01) |
| *C07C 317/32* | (2006.01) |
| *C07D 211/34* | (2006.01) |
| *C07D 211/60* | (2006.01) |
| *C07D 213/56* | (2006.01) |
| *C07D 295/155* | (2006.01) |

(52) U.S. Cl.
CPC .......... *C07D 471/04* (2013.01); *A61K 31/445* (2013.01); *A61K 31/4409* (2013.01); *A61K 31/4465* (2013.01); *A61K 31/505* (2013.01); *C07C 311/21* (2013.01); *C07C 317/32* (2013.01); *C07D 209/08* (2013.01); *C07D 211/26* (2013.01); *C07D 211/34* (2013.01); *C07D 211/60* (2013.01); *C07D 213/40* (2013.01); *C07D 213/56* (2013.01); *C07D 213/76* (2013.01); *C07D 235/08* (2013.01); *C07D 239/26* (2013.01); *C07D 263/56* (2013.01); *C07D 277/64* (2013.01); *C07D 295/135* (2013.01); *C07D 295/155* (2013.01); *C07D 401/12* (2013.01)

(58) Field of Classification Search
None
See application file for complete search history.

(56) References Cited

U.S. PATENT DOCUMENTS

| 4,595,780 | A | 6/1986 | Ogata et al. |
| 6,956,141 | B1 | 10/2005 | Maas-Brunner et al. |
| 6,967,196 | B1 * | 11/2005 | Smith .................. C07C 311/21 514/210.1 |
| 2007/0225344 | A1 | 9/2007 | Gopalsamy |
| 2009/0163545 | A1 | 6/2009 | Goldfarb |

(Continued)

FOREIGN PATENT DOCUMENTS

| JP | 2002537367 A | 11/2002 |
| JP | 2011507910 A | 3/2011 |

(Continued)

OTHER PUBLICATIONS

Cai, Dawei. Identification of Disubstituted Sulfonamide Compounds as Specific Inhibitors of Hepatitis B Virus Covalently Closed DNA Formation. Antimicrobial Agents and Chemotherapy. 2012, 56(8), 4277-4288.*

(Continued)

*Primary Examiner* — Samantha Shterengarts
(74) *Attorney, Agent, or Firm* — Saul Ewing LLP; Kathryn Doyle; Domingos J. Silva

(57) ABSTRACT

Pharmaceutical compositions of the invention comprise covalently closed circular DNA formation inhibitors having a disease-modifying action in the treatment of diseases associated with the formation of covalently closed circular DNA that include hepatitis B infection, and any disease involving formation of covalently closed circular DNA.

33 Claims, 6 Drawing Sheets

(56) References Cited

U.S. PATENT DOCUMENTS

| | | |
|---|---|---|
| 2009/0312328 A1 | 12/2009 | Kubota et al. |
| 2011/0009622 A1 | 1/2011 | Jitsuoka et al. |
| 2011/0033417 A1 | 2/2011 | Anilkumar et al. |
| 2011/0038884 A1 | 2/2011 | Takigawa et al. |
| 2011/0274655 A1 | 11/2011 | Bahadoor et al. |

FOREIGN PATENT DOCUMENTS

| | | |
|---|---|---|
| WO | 2006004622 A2 | 1/2006 |
| WO | 2011041713 A2 | 4/2011 |
| WO | 2011050284 A1 | 4/2011 |
| WO | 2012037108 A1 | 3/2012 |

OTHER PUBLICATIONS

Database Registry Chemical Abstracts Service, Columbus, Ohio, Accession No. RN 553615-40-0, Jul. 2003, RN 432516-49-9, Jun. 2002, RN 4172-31-0, Nov. 1984, RN 300574-10-1, Oct. 2000, RN 683261-44-1, May 2004, RN 922858-24-0, Feb. 2007, RN 683259-53-2, May 2004, RN 941966-19-4, Jul. 2007, RN 875581-27-4, Mar. 2006, RN 476297-93-5, Dec. 2002.*

Ito, Nobuyuki. Cancer Science 94(1), (2003) 3-8.*

Database Registry Chemical Abstracts Service, Columbus, Ohio, Accession No. RN 432018-03-6, Entered STN: Jun. 19, 2002.*

International Search Report dated May 13, 2013 for PCT International Application No. PCT/US2013/028150.

Kim, et al., "Discovery and Development of Anti-HBV Agents and Their Resistance", Molecules 15(9), Aug. 27, 2010, 5878-5908.

Supplementary European Search Report for European Patent Application No. 13755289.9 dated Dec. 4, 2015.

Database Registry Chemical Abstracts Service, Columbus, Ohio, Accession No. RN 431922-27-9, Jun. 2002.

Liu, et al., "Discovery of Novel 2-N-Aryl-Substituted Benzenesutfonamidoacetamides: Orally Bioavailable Tubulin Polymerization Inhibitors with Marked Antitumor Activities", ChemMedChem, vol. 7, No. 4, 2012, pp. 680-693.

Markt, et al., "Discovery of Novel CB2 Receptor Ligands by a Pharmacophore-based Virtual Screening Workflow", J. Med. Chem., vol. 52, 2009, pp. 369-378.

* cited by examiner

Figure 1: 2-[Benzenesulfonyl-(2-chloro-5-trifluoromethyl-phenyl)-amino]-N-pyridin-4-ylmethyl-acetamide (example 1) as an inhibitor of HBeAg production in HepDE19 cells.
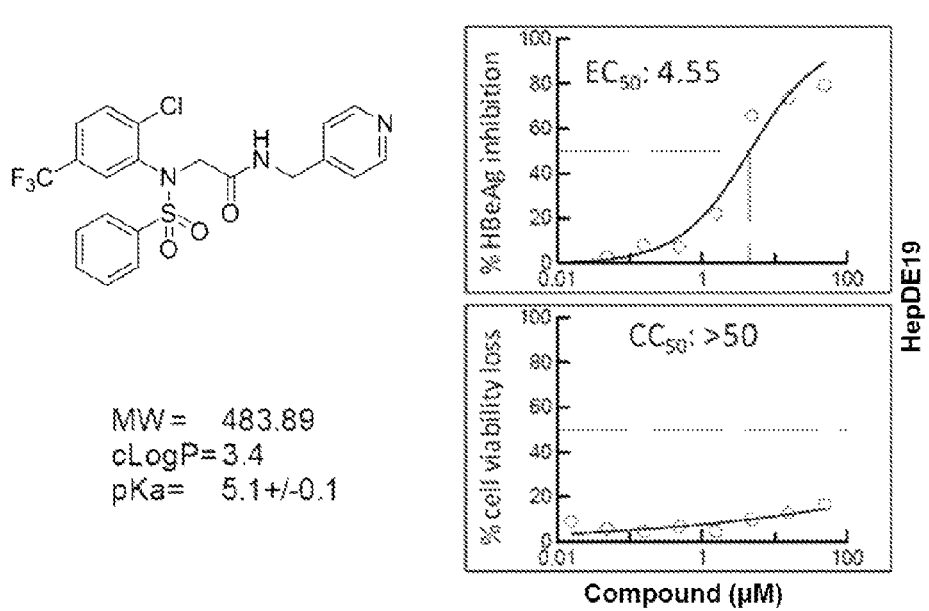

Figure 2: 2-[Benzenesulfonyl-(2-chloro-5-trifluoromethyl-phenyl)-amino]-N-pyridin-4-ylmethyl-acetamide (Example 1) reduces the levels of HBV cccDNA and DP-rcDNA in cell cultures.
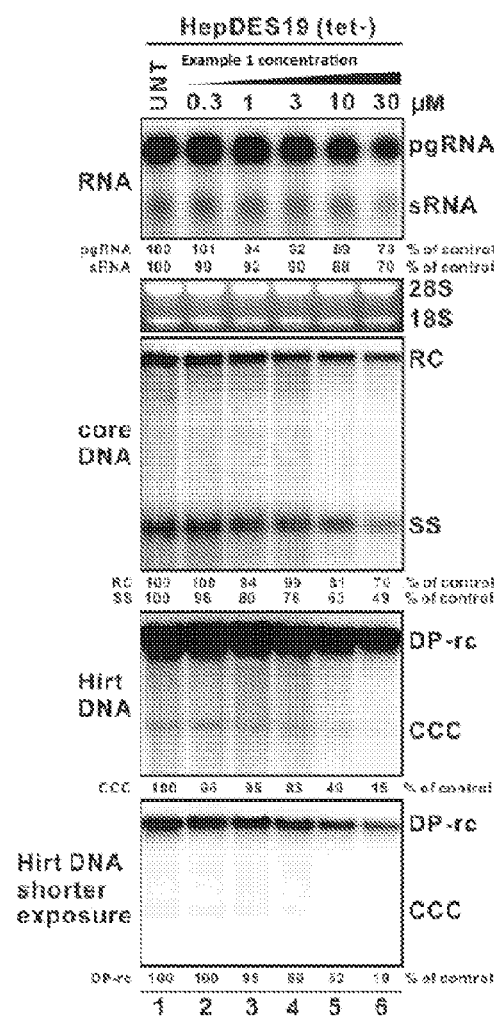

Figure 3: 2-[Benzenesulfonyl-(2-chloro-5-trifluoromethyl-phenyl)-amino]-N-pyridin-4-ylmethyl-acetamide (Example 1) does not inhibit viral polymerase activity.

Figure 4: 4-(Benzyl-methyl-sulfamoyl)-N-(2-methyl-benzothiazol-5-yl)-benzamide (example 1) as an inhibitor of HBeAg production in HepDE19 cells.
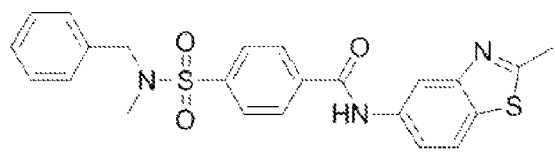
MW = 451.56
cLogP = 4.81
pKa = 2.78+/-0.3
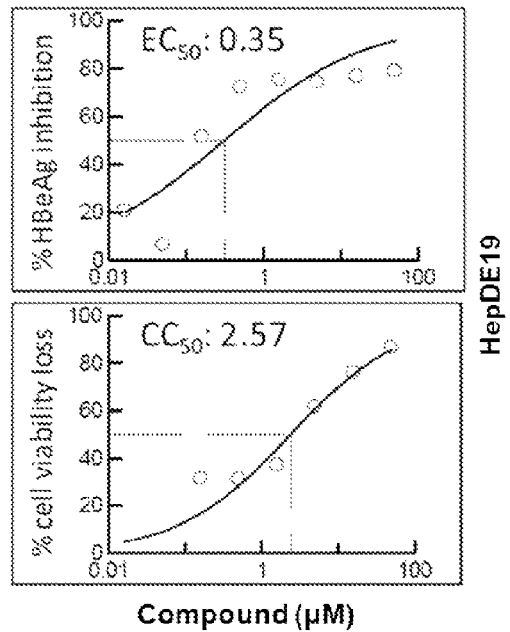

Figure 5: 4-(Benzyl-methyl-sulfamoyl)-N-(2-methyl-benzothiazol-5-yl)-benzamide (example 1) reduces the levels of cccDNA and DP-rcDNA in cell cultures.
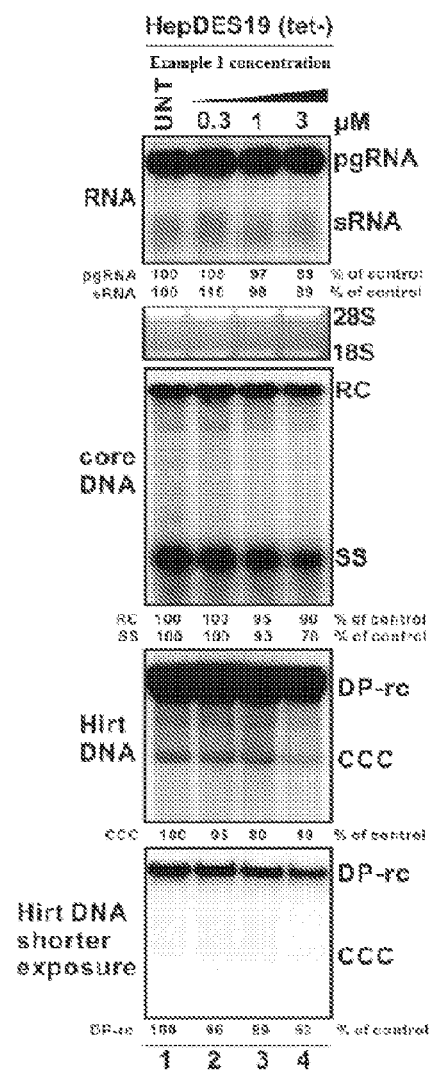

Figure 6: 4-(Benzyl-methyl-sulfamoyl)-N-(2-methyl-benzothiazol-5-yl)-benzamide (example 1) does not inhibit viral polymerase activity at 3 µM.
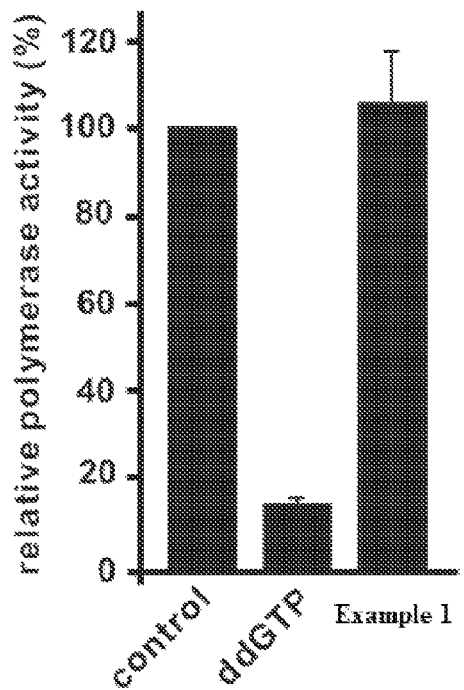

INHIBITORS OF HEPATITIS B VIRUS COVALENTLY CLOSED CIRCULAR DNA FORMATION AND THEIR METHOD OF USE

CROSS REFERENCE TO RELATED APPLICATION

This application is a U.S. National Phase of International Application No. PCT/US2013/028150, filed Feb. 28, 2013, which claims the benefit of U.S. Provisional Application No. 61/605,059 filed Feb. 29, 2012 and U.S. Provisional Application No. 61/605,071 filed Feb. 22, 2012, which are herein incorporated by reference in their entirety.

STATEMENT REGARDING FEDERALLY SPONSORED RESEARCH OR DEVELOPMENT

This invention was made with government support under Contract Nos. R56AI066024 and R01AI094474 awarded by the National Institutes of Health. The government has certain rights in the invention.

FIELD OF INVENTION

The present invention describes compounds and methods useful as inhibitors of hepatitis B Virus covalently closed circular DNA formation, useful for the treatment of hepatitis B and related conditions. The present invention further describes a novel chemotype useful for the treatment of diseases that involve the formation of covalently closed circular DNA.

BACKGROUND OF THE INVENTION

It is estimated that 2 billion people worldwide have been infected with hepatitis B virus (HBV). Although most adulthood infections are transient, approximately 5-10% of infected adults and over 90% of infected neonates fail to mount a sufficient immune response to clear the virus, and develop a life-long chronic infection (Liang, T. J. 2009. McMahon, B. J. 2005). Chronic hepatitis B is currently a substantial public health burden affecting approximately 350 million individuals worldwide. These patients have an elevated risk of liver cirrhosis, hepatocellular carcinoma (HCC), and other severe clinical sequelae (Block, T. M., H. Guo, and J. T. Guo. 2007. Liang, T. J. 2009). It is therefore a global health priority to cure chronic HBV infection and prevent its dire consequences.

HBV is a noncytopathic, liver tropic DNA virus belonging to Hepadnaviridae family. Upon infection, the virus genomic relaxed circular (rc) DNA is transported into the cell nucleus and converted to episomal covalently closed circular (ccc) DNA, which serves as the transcription template for all the viral mRNAs. After transcription and nuclear exportation, cytoplasmic viral pregenomic (pg) RNA is assembled with HBV polymerase and capsid proteins to form the nucleocapsid, inside of which polymerase-catalyzed reverse transcription yields minus-strand DNA, which is subsequently copied into plus-strand DNA to form the progeny rcDNA genome. The newly synthesized mature nucleocapsids will either be packaged with viral envelope proteins and egress as virion particles, or shuttle to the nucleus to amplify the cccDNA reservoir through intracellular cccDNA amplification pathway (Block, T. M., H. Guo, and J. T. Guo. 2007. Nassal, M. 2008. Seeger, C., and W. S. Mason. 2000).

cccDNA is an essential component of the HBV life cycle, and is responsible for the establishment of infection and viral persistence. Currently, the detailed molecular mechanism by which rcDNA is converted into cccDNA remains poorly understood. Considering the subcellular location and unique structures of these two viral DNA molecules, intricate transitions and biochemical reactions should occur during cccDNA formation. First, the cytoplasmic capsid rcDNA needs to be transported into the nucleus via karyopherin-dependent recognition of nuclear localization signals (NLS) on the capsid protein (Kann, M., A. Schmitz, and B. Rabe. 2007. Rabe, B., A. Vlachou, N. Pante, A. Helenius, and M. Kann. 2003). Second, several reactions are required due to the unique terminal features of rcDNA, these include, but may not be in a sequential order: 1) completion of viral plus strand DNA synthesis; 2) removal of the 5'-capped RNA primer at the 5' terminus of plus strand DNA; 3) removal of the viral polymerase covalently attached to the 5' end of minus strand DNA; 4) removal of one copy of the terminal redundancies on minus strand DNA (Sohn, J. A., S. Litwin, and C. Seeger. 2009); 5) ligation of both strands to generate cccDNA. Recently, a protein-free rcDNA form without covalently bonded viral polymerase has been identified, which was designated as deproteinized rcDNA (DP-rcDNA) and demonstrated as a functional precursor intermediate, if not the only, for cccDNA formation (Gao, W., and J. Hu. 2007. Guo, H., D. Jiang, T. Zhou, A. Cuconati, T. M. Block, and J. T. Guo. 2007. Guo, H., R. Mao, T. M. Block, and J. T. Guo. 2010). This DP-rcDNA species thus provides a potential antiviral target for cccDNA intervention.

To date, there is no definitive cure for chronic hepatitis B. Currently approved drugs for HBV treatment are interferon-α (IFN-α) and 5 nucleos(t)ide analogues (lamivudine, adefovir, entecavir, telbivudine, and tenofovir). IFN-α only achieves sustained virological response in less than 40% of patients after 48 weeks of treatment, with significant side effects. The five nucleos(t)ide analogues all act as potent inhibitors of viral polymerase, but rarely cure HBV infection (Gish, R. G., A. S. Lok, T. T. Chang, R. A. de Man, A. Gadano, J. Sollano, K. H. Han, Y. C. Chao, S. D. Lee, M. Harris, J. Yang, R. Colonno, and H. Brett-Smith. 2007), and emergence of resistance dramatically limits their long-term efficacy (Pawlotsky, J. M., G. Dusheiko, A. Hatzakis, D. Lau, G. Lau, T. J. Liang, S. Locarnini, P. Martin, D. D. Richman, and F. Zoulim. 2008). Theoretically, the major limitation of current treatment is the failure to eliminate the preexisting cccDNA pool, and/or prevent cccDNA formation from trace-level wild-type or drug-resistant virus. Thus there is an urgent unmet need for the development of novel therapeutic agents that directly target cccDNA formation and maintenance.

There is a long felt need for new antiviral drugs that are both disease-modifying and effective in treating patients that are infected with hepatitis B virus. There is also a clear and present need for new antiviral drugs that are both disease modifying and effective in treating patients that are infected with drug resistant hepatitis B virus. The present invention addresses the need for new antiviral drugs that are both disease-modifying and effective in treating patients that are infected with hepatitis B virus. The present invention also addresses the long felt need for new treatments for and means of preventing diseases that involve the formation of covalently closed circular DNA.

BRIEF SUMMARY OF THE INVENTION

The present invention is directed toward novel functionalized sulfonamides compounds of formula (I),

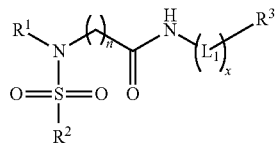

(I)

Including hydrates, solvates, pharmaceutically acceptable salts, prodrugs and complexes thereof, wherein:

$R^1$ is selected from the group consisting of optionally substituted phenyl, optionally substituted $C_1$-$C_6$ linear alkyl, optionally substituted $C_1$-$C_6$ branched alkyl, optionally substituted $C_3$-$C_7$ cycloalkyl, and optionally substituted heteroaryl;

$R^2$ is selected from the group consisting of optionally substituted phenyl, optionally substituted $C_1$-$C_6$ linear alkyl, optionally substituted $C_1$-$C_6$ branched alkyl, optionally substituted $C_3$-$C_7$ cycloalkyl, and optionally substituted heteroaryl;

$R^3$ is selected from the group consisting of optionally substituted phenyl, optionally substituted $C_1$-$C_6$ linear alkyl, optionally substituted $C_1$-$C_6$ branched alkyl, optionally substituted $C_3$-$C_7$ cycloalkyl, optionally substituted heteroaryl,

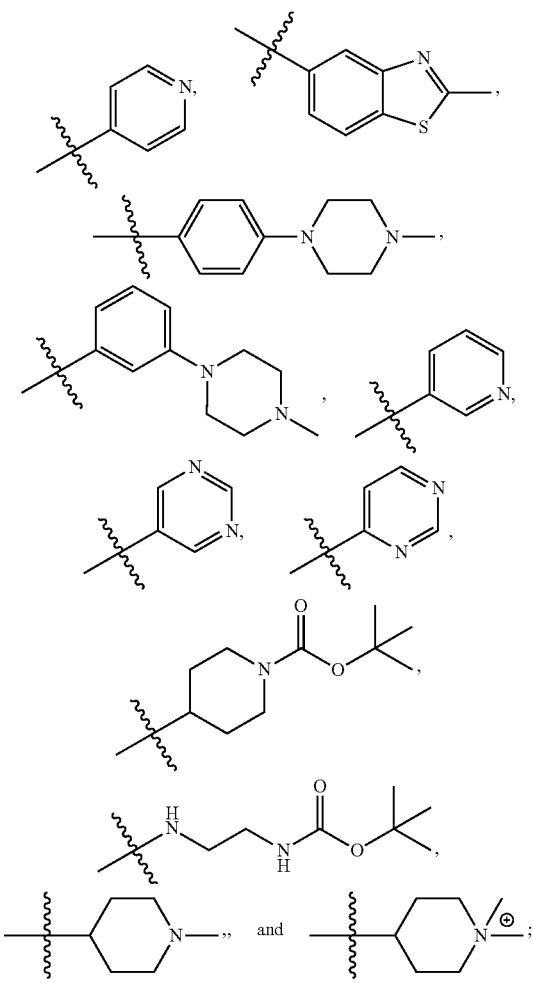

n is 1, 2, or 3;
$L^1$ is, independently, —[C($R^{4a}R^{4b}$)]$_m$—;
m is 1 or 2;

$R^{4a}$ and $R^{4b}$ are, at each occurrence, each independently selected from a group consisting of hydrogen and methyl; $R^{4a}$ and $R^{4b}$ are taken together with the atom to which they are bound to form a cyclopropyl ring;

x, at each occurrence, independently is 0 or 1;

The present invention is further directed toward novel functionalized sulfonamides compounds of formula (Ia),

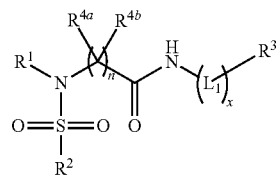

(Ia)

Including hydrates, solvates, pharmaceutically acceptable salts, prodrugs and complexes thereof.

The present invention is further directed toward novel functionalized sulfonamides compounds of formula (Ib),

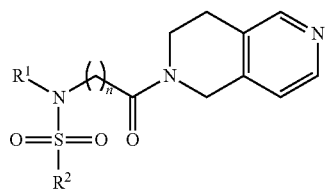

(Ib)

Including hydrates, solvates, pharmaceutically acceptable salts, prodrugs and complexes thereof.

The present invention is further directed toward novel functionalized sulfonamides compounds of formula (Ic),

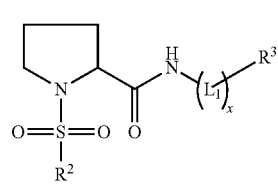

(Ic)

Including hydrates, solvates, pharmaceutically acceptable salts, prodrugs and complexes thereof.

The present invention is further directed toward novel functionalized sulfonamides compounds of formula (Id),

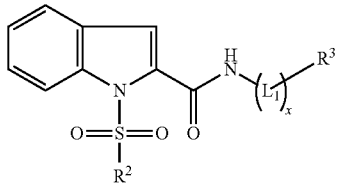

(Id)

Including hydrates, solvates, pharmaceutically acceptable salts, prodrugs and complexes thereof.

The present invention is further directed toward novel functionalized sulfonamides compounds of formula (II),

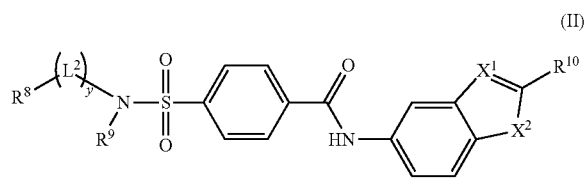

(II)

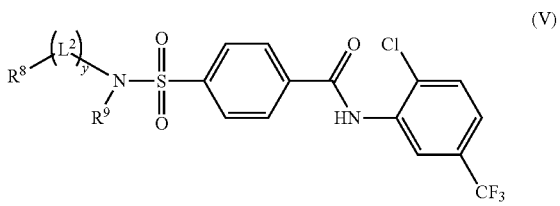

(V)

Including hydrates, solvates, pharmaceutically acceptable salts, prodrugs and complexes thereof, wherein:

$R^8$ is selected from the group consisting of optionally substituted phenyl, optionally substituted $C_1$-$C_6$ linear alkyl, optionally substituted $C_1$-$C_6$ branched alkyl, optionally substituted $C_3$-$C_7$ cycloalkyl, and optionally substituted heteroaryl;

$R^9$ is selected from the group consisting of hydrogen, optionally substituted $C_1$-$C_6$ linear alkyl, and optionally substituted $C_1$-$C_6$ branched alkyl;

$R^{10}$ is selected from the group consisting of hydrogen, optionally substituted $C_1$-$C_6$ linear alkyl, optionally substituted $C_1$-$C_6$ branched alkyl, and optionally substituted $C_3$-$C_7$ cycloalkyl;

$X^1$ is selected from the group consisting of CH and nitrogen;

$X^2$ is selected from the group consisting of, sulfur, oxygen, and NH;

$L^2$ is, independently, —$[C(R^{11a}R^{11b})]_q$—;

q is 1 or 2;

$R^{11a}$ and $R^{11b}$ are, at each occurrence, each independently selected from the group consisting of hydrogen and methyl;

$R^{11a}$ and $R^{11b}$ are taken together with the atom to which they are bound to form a cyclopropyl ring;

y is 0 or 1;

The present invention is further directed toward novel functionalized sulfonamides compounds of formula (III),

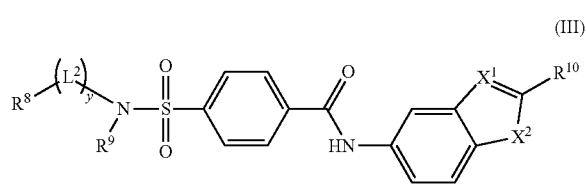

(III)

Including hydrates, solvates, pharmaceutically acceptable salts, prodrugs and complexes thereof.

The present invention is further directed toward novel functionalized sulfonamides compounds of formula (IV),

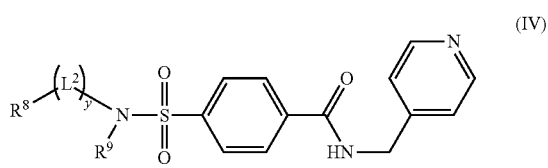

(IV)

Including hydrates, solvates, pharmaceutically acceptable salts, prodrugs and complexes thereof.

The present invention is further directed toward novel functionalized sulfonamides compounds of formula (V), Including hydrates, solvates, pharmaceutically acceptable salts, prodrugs and complexes thereof.

The present invention further relates to compositions comprising:

an effective amount of one or more compounds according to the present invention and an excipient.

The present invention also relates to a method for treating or preventing diseases that involve the formation of covalently closed circular DNA, including, for example, hepatitis B infection, said method comprising administering to a subject an effective amount of a compound or composition according to the present invention.

The present invention yet further relates to a method for treating or preventing diseases that involve the formation of covalently closed circular DNA, including, for example, hepatitis B infection, wherein said method comprises administering to a subject a composition comprising an effective amount of one or more compounds according to the present invention and an excipient.

The present invention also relates to a method for treating or preventing disease or conditions associated with hepatitis B infection, and diseases that involve the formation of covalently closed circular DNA. Said methods comprise administering to a subject an effective amount of a compound or composition according to the present invention.

The present invention yet further relates to a method for treating or preventing disease or conditions associated with hepatitis B infection, and diseases that involve the formation of covalently closed circular DNA, wherein said method comprises administering to a subject a composition comprising an effective amount of one or more compounds according to the present invention and an excipient.

The present invention also relates to a method for treating or preventing disease or conditions associated with the formation of covalently closed circular DNA. Said methods comprise administering to a subject an effective amount of a compound or composition according to the present invention.

The present invention yet further relates to a method for treating or preventing disease or conditions associated with the formation of covalently closed circular DNA, wherein said method comprises administering to a subject a composition comprising an effective amount of one or more compounds according to the present invention and an excipient.

The present invention further relates to a process for preparing the covalently closed circular DNA inhibitors of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

BRIEF DESCRIPTION OF THE DRAWINGS

FIG. 1: 2-[Benzenesulfonyl-(2-chloro-5-trifluoromethyl-phenyl)-amino]-N-pyridin-4-ylmethyl-acetamide as an inhibitor of HBV e antigen (HBeAg) production in HepDE19 cells. The chemical structure and property of 2-[Benzenesulfonyl-(2-chloro-5-trifluoromethyl-phenyl)-amino]-N-pyridin-4-ylmethyl-acetamide are presented (left panel). Graphs represent inhibition of HBeAg secretion (right top panel) and loss of HepDE19 cell viability (right bottom panel) in the same samples. Incubation was for nine days with actively dividing cells. $EC_{50}$ and $CC_{50}$ values (μM) were calculated with XLfit 4.0 (IDBS, Surrey UK). In HepDE19 cells, under the conditions used (Zhou, T., H. Guo, J. T. Guo, A. Cuconati, A. Mehta, and T. M. Block. 2006. Guo, H., D. Jiang, T. Zhou, A. Cuconati, T. M. Block, and J. T. Guo. 2007), authentic precore mRNA containing an intact HBeAg gene is only transcribed from cccDNA template, thus inhibition of HBeAg production is a surrogate marker for inhibition of HBV cccDNA.

FIG. 2: 2-[Benzenesulfonyl-(2-chloro-5-trifluoromethyl-phenyl)-amino]-N-pyridin-4-ylmethyl-acetamide reduces the levels of HBV cccDNA and DP-rcDNA in cell cultures. After withdrawal of tetracycline, HepDES19 cells were left untreated or treated with 2-[Benzenesulfonyl-(2-chloro-5-trifluoromethyl-phenyl)-amino]-N-pyridin-4-ylmethyl acetamide at indicated concentrations with regular media changes. The cells were harvested at day 12, viral RNA (top panel), core DNA (middle panel), and protein-free DNA (DP-rcDNA and cccDNA) (bottom panels) were extracted and analyzed by Northern blot and Southern blot, respectively (Guo, H., D. Jiang, T. Zhou, A. Cuconati, T. M. Block, and J. T. Guo. 2007. Zhou, T., H. Guo, J. T. Guo, A. Cuconati, A. Mehta, and T. M. Block. 2006). longer exposure was used to highlight the cccDNA signals. The relative intensity was quantitated and plotted as percentage of RNA or DNA level of the controls.

FIG. 3: 2-[Benzenesulfonyl-(2-chloro-5-trifluoromethyl-phenyl)-amino]-N-pyridin-4-ylmethyl-acetamide does not inhibit viral polymerase activity. HBV virion particles purified from the HepDE19 culture fluid were subjected to endogenous polymerase reaction with $^{32}$P-dCTP plus 2-[Benzenesulfonyl-(2-chloro-5-trifluoromethyl-phenyl)-amino]-N-pyridin-4-ylmethyl-acetamide at indicated concentrations. ddGTP was a reference chain terminator in the reaction. Incorporated $^{32}$P-dCTP was counted with a liquid scintillation counter (PerkinElmer). The relative polymerase activity was plotted as percentage of CPM read out of control reaction (Y-axis).

FIG. 4: 4-(Benzyl-methyl-sulfamoyl)-N-(2-methyl-benzothiazol-5-yl)-benzamide as an inhibitor of HBV e antigen (HBeAg) production in HepDE19 cells: The chemical calculated properties of 4-(Benzyl-methyl-sulfamoyl)-N-(2-methyl-benzothiazol-5-yl)-benzamide are presented (left panel). Graphs represent inhibition of HBeAg secretion (right top panel) and loss of HepDE19 cell viability (right bottom panel) in the same samples. Incubation was for nine days with actively dividing cells. $EC_{50}$ and $CC_{50}$ values (μM) were calculated with XLfit 4.0 (IDBS, Surrey UK). In HepDE19 cells, under the conditions used (Zhou, T., H. Guo, J. T. Guo, A. Cuconati, A. Mehta, and T. M. Block. 2006. Guo, H., D. Jiang, T. Zhou, A. Cuconati, T. M. Block, and J. T. Guo. 2007), authentic precore mRNA containing an intact HBeAg gene is only transcribed from cccDNA template, thus inhibition of HBeAg production is a surrogate marker for inhibition of HBV cccDNA.

FIG. 5: 4-(Benzyl-methyl-sulfamoyl)-N-(2-methyl-benzothiazol-5-yl)-benzamide reduces the levels of HBV cccDNA and DP-rcDNA in cell cultures. After withdrawal of tetracycline, HepDES19 cells were left untreated or treated with 4-(Benzyl-methyl-sulfamoyl)-N-(2-methyl-benzothiazol-5-yl)-benzamide at indicated concentrations with regular media changes. The cells were harvested at day 12, viral RNA (top panel), core DNA (middle panel), and protein-free DNA (DP-rcDNA and cccDNA) (bottom panels) were extracted and analyzed by Northern blot and Southern blot, respectively. (6, 20) longer exposure was used to highlight the cccDNA signals. The relative intensity was quantitated and plotted as percentage of RNA or DNA level of the controls.

FIG. 6: 4-(Benzyl-methyl-sulfamoyl)-N-(2-methyl-benzothiazol-5-yl)-benzamide does not inhibit viral polymerase activity. HBV virion particles purified from the HepDE19 culture fluid were subjected to endogenous polymerase reaction with $^{32}$P-dCTP plus 4-(Benzyl-methyl-sulfamoyl)-N-(2-methyl-benzothiazol-5-yl)-benzamide at 3 μM. ddGTP was a reference chain terminator in the reaction. Incorporated $^{32}$P-dCTP was counted with a liquid scintillation counter (PerkinElmer). The relative polymerase activity was plotted as percentage of CPM read out of control reaction (Y-axis).

DETAILED DESCRIPTION OF THE INVENTION

The underlying cause of hepatitis B virus chronicity is the intracellular persistence of an multicopy episomal form of the virus genome, covalently closed circular (ccc) DNA, which has a very long half life in the nucleus of infected hepatocytes, and is only indirectly affected by current therapies (Lok, A. S. 2009). In order to clear the infection, a durable, curative antiviral therapy that reduces the level of HBV cccDNA directly without killing of infected hepatocytes is warranted. It has been discovered that the covalently closed circular DNA inhibitors of the present invention are capable of treating and preventing diseases associated with the formation of covalently closed circular DNA, for example hepatitis B infection.

Without wishing to be limited by theory, it is believed that covalently closed circular DNA inhibitors can ameliorate, abate, otherwise cause to be controlled, diseases associated the formation of covalently closed circular DNA.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

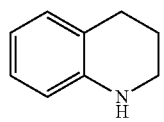

is, for the purposes of the present invention, considered a heterocyclic unit. 6,7-Dihydro-5H-cyclopentapyrimidine having the formula:

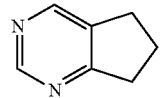

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

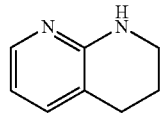

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{12}$, —SR$^{12}$, —N(R$^{12}$)$_2$, —NR$^{12}$C(O)R$^{12}$, —SO$_2$R$^{12}$, —SO$_2$OR$^{12}$, —SO$_2$N(R$^{12}$)$_2$, —C(O)R$^{12}$, —C(O)OR$^{12}$, —C(O)N(R$^{12}$)$_2$, C$_{1-6}$ alkyl, C$_{1-6}$ haloalkyl, C$_{1-6}$ alkoxy, C$_{2-8}$ alkenyl, C$_{2-8}$ alkynyl, C$_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{12}$; wherein R$^{12}$, at each occurrence, independently is hydrogen, —OR$^{13}$, —SR$^{13}$, —C(O)R$^{13}$, —C(O)OR$^{13}$, —C(O)N(R$^{13}$)$_2$, —SO$_2$R$^{13}$, —S(O)$_2$OR$^{13}$, —N(R$^{13}$)$_2$, —NR$^{13}$C(O)R$^{13}$, C$_{1-6}$alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{12}$ units taken together with the atom(s) to which they are bound form an optionally substituted carbocycle or heterocycle wherein said carbocycle or heterocycle has 3 to 7 ring atoms; wherein R$^{13}$, at each occurrence, independently is hydrogen, C$_{1-6}$ alkyl, C$_{1-6}$ haloalkyl, C$_{2-8}$ alkenyl, C$_{2-8}$ alkynyl, cycloalkyl (e.g., C$_{3-6}$ cycloalkyl), aryl, heterocycle, or heteroaryl, or two R$^{13}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{14}$; for example, —OH, —OCH$_3$, —OCH$_2$CH$_3$, —OCH$_2$CH$_2$CH$_3$;
ii) —C(O)R$^{14}$; for example, —COCH$_3$, —COCH$_2$CH$_3$, —COCH$_2$CH$_2$CH$_3$;
iii) —C(O)OR$^{14}$; for example, —CO$_2$CH$_3$, —CO$_2$CH$_2$CH$_3$, —CO$_2$CH$_2$CH$_2$CH$_3$;
iv) —C(O)N(R$^{14}$)$_2$; for example, —CONH$_2$, —CONHCH$_3$, —CON(CH$_3$)$_2$;
v) —N(R$^{14}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_q$X$_z$; wherein X is halogen, m is from 0 to 2, q+z=3; for example, —CH$_2$F, —CHF$_2$, —CF$_3$, —CCl$_3$, or —CBr$_3$;
viii) —SO$_2$R$^{14}$; for example, —SO$_2$H; —SO$_2$CH$_3$; —SO$_2$C$_6$H$_5$;
ix) C$_1$-C$_6$ linear, branched, or cyclic alkyl;
x) Cyano
xi) Nitro;
xii) N(R$^{14}$)C(O)R$^{14}$;
xiii) Oxo (═O);
xiv) Heterocycle; and
xv) Heteroaryl.
wherein each R$^{14}$ is independently hydrogen, optionally substituted C$_1$-C$_6$ linear or branched alkyl (e.g., optionally substituted C$_1$-C$_4$ linear or branched alkyl), or optionally substituted C$_3$-C$_6$ cycloalkyl (e.g optionally substituted C$_3$-C$_4$ cycloalkyl); or two R$^{14}$ units can be taken together to form a ring comprising 3-7 ring atoms. In certain aspects, each R$^{14}$ is independently hydrogen, C$_1$-C$_6$ linear or branched alkyl optionally substituted with halogen or C$_3$-C$_6$ cycloalkyl or C$_3$-C$_6$ cycloalkyl.

At various places in the present specification, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_{1-6}$, C$_{1-5}$, C$_{1-4}$, C$_{1-3}$, C$_{1-2}$, C$_{2-6}$, C$_{2-5}$, C$_{2-4}$, C$_{2-3}$, C$_{3-6}$, C$_{3-5}$, C$_{3-4}$, C$_{4-6}$, C$_{4-5}$, and C$_{5-6}$, alkyl.

For the purposes of the present invention the terms "compound," "analog," and "composition of matter" stand equally well for the covalently closed circular DNA inhibitors described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include NaHCO$_3$, Na$_2$CO$_3$, KHCO$_3$, K$_2$CO$_3$, Cs$_2$CO$_3$, LiOH, NaOH, KOH, NaH$_2$PO$_4$, Na$_2$HPO$_4$, and Na$_3$PO$_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in N(R$^{13}$)$_2$, each R$^{13}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Covalently Closed Circular DNA Inhibitors

The covalently closed circular DNA inhibitors of the present invention are functionalized sulfonamides, and include all enantiomeric and diastereomeric forms and pharmaceutically accepted salts thereof having the formula (I):

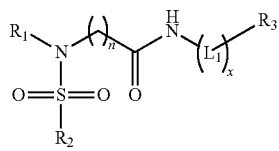
(I)

Including hydrates, solvates, pharmaceutically acceptable salts, prodrugs and complexes thereof, wherein:

$R^1$ is selected from the group consisting of optionally substituted phenyl, optionally substituted $C_1$-$C_6$ linear alkyl, optionally substituted $C_1$-$C_6$ branched alkyl, optionally substituted $C_3$-$C_7$ cycloalkyl, and optionally substituted heteroaryl;

$R^2$ is selected from the group consisting of optionally substituted phenyl, optionally substituted $C_1$-$C_6$ linear alkyl, optionally substituted $C_1$-$C_6$ branched alkyl, optionally substituted $C_3$-$C_7$ cycloalkyl, and optionally substituted heteroaryl;

$R^3$ is selected from the group consisting of optionally substituted phenyl, optionally substituted $C_1$-$C_6$ linear alkyl, optionally substituted $C_1$-$C_6$ branched alkyl, optionally substituted $C_3$-$C_7$ cycloalkyl, optionally substituted heteroaryl,

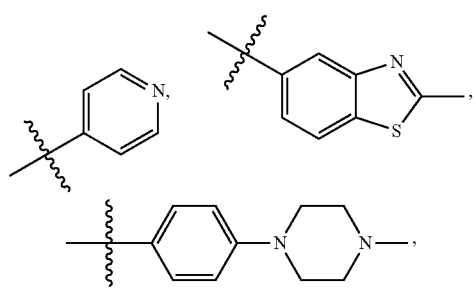

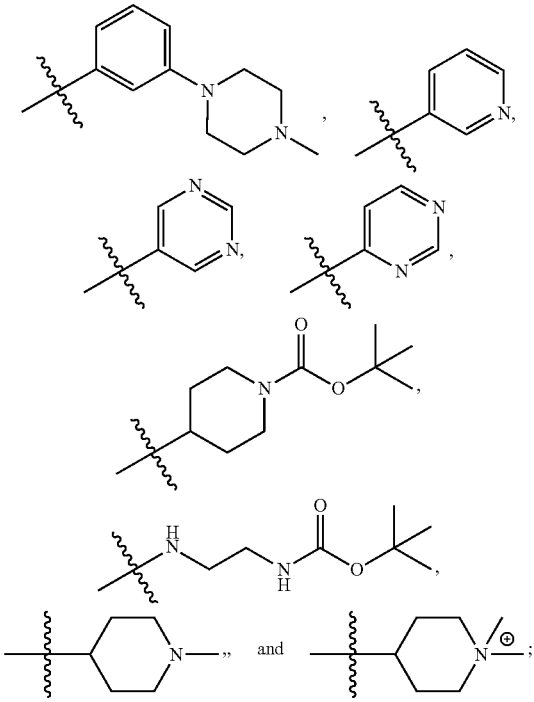

n is 1, 2, or 3;
$L^1$ is, independently, $-[C(R^{4a}R^{4b})]_m-$;
m is 1 or 2;
$R^{4a}$ and $R^{4b}$ are, at each occurrence, each independently selected from a group consisting of hydrogen and methyl;
$R^{4a}$ and $R^{4b}$ are taken together with the atom to which they are bound to form a cyclopropyl ring;
x, at each occurrence, independently is 0 or 1;

The present invention is further directed toward novel functionalized sulfonamides, compounds of formula (Ia),

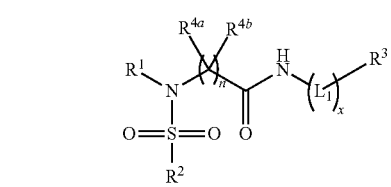
(Ia)

Including hydrates, solvates, pharmaceutically acceptable salts, prodrugs and complexes thereof.

The present invention is further directed toward novel functionalized sulfonamides, compounds of formula (Ib),

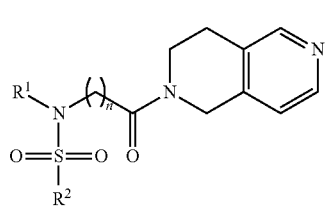
(Ib)

Including hydrates, solvates, pharmaceutically acceptable salts, prodrugs and complexes thereof.

The present invention is further directed toward novel functionalized sulfonamides, compounds of formula (Ic), (Ic)

Including hydrates, solvates, pharmaceutically acceptable salts, prodrugs and complexes thereof.

The present invention is further directed toward novel functionalized sulfonamides, compounds of formula (Id), (Id)

Including hydrates, solvates, pharmaceutically acceptable salts, prodrugs and complexes thereof.

The embodiments of the present invention include compounds having formula (Ie), (Ie)

Including hydrates, solvates, pharmaceutically acceptable salts, prodrugs and complexes thereof.

The embodiments of the present invention include compounds having formula (If), (If)

Including hydrates, solvates, pharmaceutically acceptable salts, prodrugs and complexes thereof.

The embodiments of the present invention include compounds having formula (Ig), (Ig)

Including hydrates, solvates, pharmaceutically acceptable salts, prodrugs and complexes thereof.

The embodiments of the present invention include compounds having formula (Ih), (Ih)

Including hydrates, solvates, pharmaceutically acceptable salts, prodrugs and complexes thereof.

The present invention is further directed toward novel functionalized sulfonamides, compounds of formula (II):

(II)

Including hydrates, solvates, pharmaceutically acceptable salts, prodrugs and complexes thereof, wherein:

$R^8$ is selected from the group consisting of optionally substituted phenyl, optionally substituted $C_1$-$C_6$ linear alkyl, optionally substituted $C_1$-$C_6$ branched alkyl, optionally substituted $C_3$-$C_7$ cycloalkyl, and optionally substituted heteroaryl;

$R^9$ is selected from the group consisting of hydrogen, optionally substituted $C_1$-$C_6$ linear alkyl, and optionally substituted $C_1$-$C_6$ branched alkyl;

$R^{10}$ is selected from the group consisting of hydrogen, optionally substituted $C_1$-$C_6$ linear alkyl, optionally substituted $C_1$-$C_6$ branched alkyl, and optionally substituted $C_3$-$C_7$ cycloalkyl;

$X^1$ is selected from the group consisting of CH and nitrogen;

$X^2$ is selected from the group consisting of, sulfur, oxygen, and NH;

$L^2$ is, independently, $-[C(R^{11a}R^{11b})]_q-$;

q is 1 or 2;

$R^{11a}$ and $R^{11b}$ are, at each occurrence, each independently selected from the group consisting of hydrogen and methyl;

$R^{11a}$ and $R^{11b}$ are taken together with the atom to which they are bound to form a cyclopropyl ring;

y is 0 or 1;

The embodiments of the present invention include compounds having formula (IIa), (IIa)

Including hydrates, solvates, pharmaceutically acceptable salts, prodrugs and complexes thereof.

The embodiments of the present invention include compounds having formula (IIb),

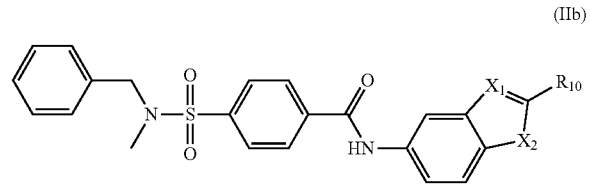
(IIb)

Including hydrates, solvates, pharmaceutically acceptable salts, prodrugs and complexes thereof.

The present invention is further directed toward novel functionalized sulfonamides, compounds of formula (III),

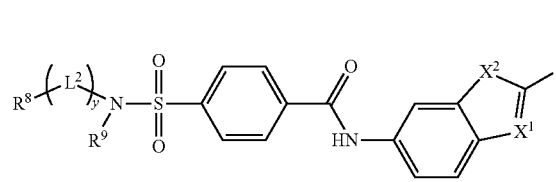
(III)

Including hydrates, solvates, pharmaceutically acceptable salts, prodrugs and complexes thereof The present invention is further directed toward novel functionalized sulfonamides, compounds of formula (IV),

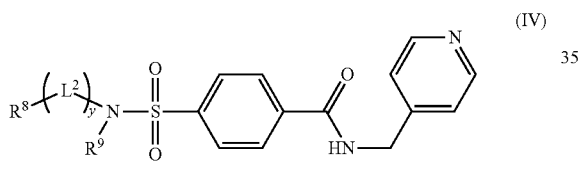
(IV)

Including hydrates, solvates, pharmaceutically acceptable salts, prodrugs and complexes thereof.

The present invention is further directed toward novel functionalized sulfonamides, compounds of formula (V),

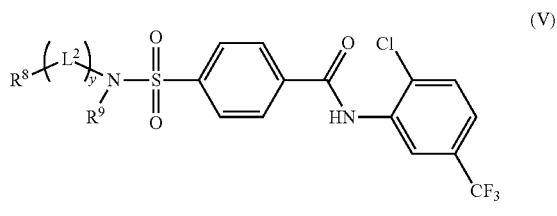
(V)

Including hydrates, solvates, pharmaceutically acceptable salts, prodrugs and complexes thereof.

In some embodiments $R^1$ is optionally substituted phenyl.
In some embodiments $R^1$ is optionally substituted $C_1$-$C_6$ linear alkyl.
In some embodiments $R^1$ is optionally substituted $C_1$-$C_6$ branched alkyl.
In some embodiments $R^1$ is optionally substituted $C_3$-$C_7$ cycloalkyl.
In some embodiments $R^1$ is optionally substituted heteroaryl.
In some embodiments $R^1$ is selected from a group consisting of 2-chloro-5-trifluoromethylphenyl, 2-bromo-5-trifluorophenyl, 2-fluoro-5-trifluoromethylphenyl, 2-chloro-5-fluorophenyl, and 4-pyridyl.

In some embodiments $R^2$ is optionally substituted phenyl
In some embodiments $R^2$ is optionally substituted $C_1$-$C_6$ linear alkyl
In some embodiments $R^2$ is optionally substituted $C_1$-$C_6$ branched alkyl
In some embodiments $R^2$ is optionally substituted $C_3$-$C_7$ cycloalkyl
In some embodiments $R^2$ is optionally substituted heteroaryl
In some embodiments $R^2$ is phenyl, 4-fluorophenyl, 4-chlorophenyl, 4-methylphenyl, 4-methoxyphenyl, or 4-trifluorophenyl.

In some embodiments $R^3$ is optionally substituted phenyl.
In some embodiments $R^3$ is optionally substituted $C_1$-$C_6$ linear alkyl.
In some embodiments $R^3$ is optionally substituted $C_1$-$C_6$ branched alkyl.
In some embodiments $R^3$ is optionally substituted $C_3$-$C_7$ cycloalkyl.
In some embodiments $R^3$ is optionally substituted heteroaryl.
In some embodiments $R^3$ is 4-pyridyl.
In some embodiments $R^3$ is selected from a group consisting of

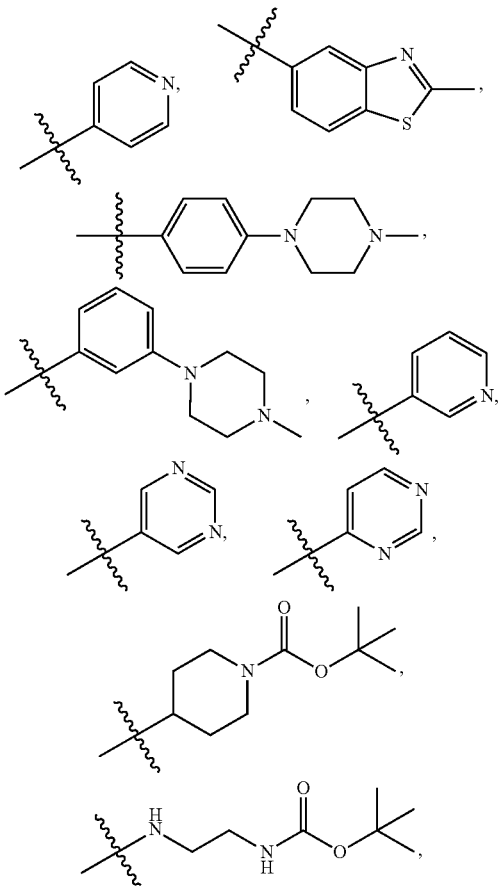

-continued

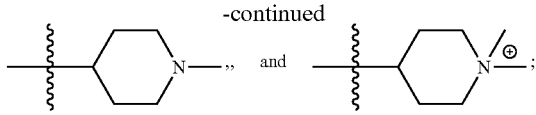

In some embodiments $R^{4a}$ is hydrogen.
In some embodiments $R^{4a}$ is methyl.
In some embodiments $R^{4b}$ is hydrogen.
In some embodiments $R^{4b}$ is methyl.
In some embodiments $R^{4a}$ and $R^{4b}$ are taken together with the atom to which they are bound to form a cyclopropyl ring.
In some embodiments n is 1.
In some embodiments n is 2.
In some embodiments n is 3.
In some embodiments m is 1.
In some embodiments m is 2.
In some embodiments x is 0.
In some embodiments x is 1.
In some embodiments $R^8$ is optionally substituted phenyl.
In some embodiments $R^8$ is optionally substituted $C_1$-$C_6$ linear alkyl.
In some embodiments $R^8$ is optionally substituted $C_1$-$C_6$ branched alkyl.
In some embodiments $R^8$ is optionally substituted $C_3$-$C_7$ cycloalkyl.
In some embodiments $R^8$ is optionally substituted heteroaryl.
In some embodiments $R^8$ is phenyl.
In some embodiments $R^9$ is hydrogen.
In some embodiments $R^9$ is optionally substituted $C_1$-$C_6$ linear alkyl
In some embodiments $R^9$ is optionally substituted $C_1$-$C_6$ branched alkyl
In some embodiments $R^9$ is methyl.
In some embodiments $R^{10}$ is hydrogen.
In some embodiments $R^{10}$ is optionally substituted $C_1$-$C_6$ linear alkyl.
In some embodiments $R^{10}$ is optionally substituted $C_1$-$C_6$ branched alkyl.
In some embodiments $R^{10}$ is methyl.
In some embodiments $R^{10}$ is cyclopropyl.
In some embodiments $R^{11a}$ is hydrogen.
In some embodiments $R^{11a}$ is methyl.
In some embodiments $R^{11b}$ is hydrogen.
In some embodiments $R^{11b}$ is methyl.
In some embodiments $R^{11a}$ and $R^{11b}$ are taken together with the atom to which they are bound to form a cyclopropyl ring.
In some embodiments q is 1.
In some embodiments q is 2.
In some embodiments y is 0.
In some embodiments y is 1.
In some embodiments $X^1$ is N
In some embodiments $X^1$ is CH
In some embodiments $X^2$ is NH.
In some embodiments $X^2$ is oxygen.
In some embodiments $X^2$ is sulfur.

Exemplary embodiments include compounds having the formula (I) or a pharmaceutically acceptable salt form thereof:

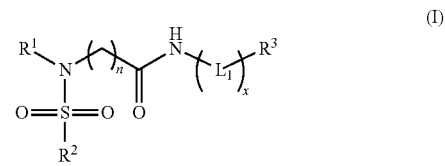

wherein non-limiting examples of $R^1$, $R^2$, $R^3$, n, $L^1$ and X are defined herein below in Table 1.

TABLE 1

| Example | $R^1$ | $R^2$ | $R^3$ | n | $L^1$ | X |
|---|---|---|---|---|---|---|
| 1 | 2-Cl,5-$CF_3$-Phenyl | Phenyl | 4-Pyridyl | 1 | $CH_2$ | 1 |
| 2 | 2-Br,5-$CF_3$-Phenyl | Phenyl | 4-Pyridyl | 1 | $CH_2$ | 1 |
| 3 | 2-F,5-$CF_3$-Phenyl | Phenyl | 4-Pyridyl | 1 | $CH_2$ | 1 |
| 4 | 2-Cl,5-$CF_3$-Phenyl | Phenyl | 4-Pyridyl | 2 | $CH_2$ | 1 |
| 5 | 2-Cl,5-$CF_3$-Phenyl | Phenyl | 4-Pyridyl | 3 | $CH_2$ | 1 |
| 6 | 2-Cl,5-$CF_3$-Phenyl | 4-F-Phenyl | 4-Pyridyl | 1 | $CH_2$ | 1 |
| 7 | 2-Cl,5-$CF_3$-Phenyl | 4-Cl-Phenyl | 4-Pyridyl | 1 | $CH_2$ | 1 |
| 8 | 2-Cl,5-$CF_3$-Phenyl | 4-$CH_3$-Phenyl | 4-Pyridyl | 1 | $CH_2$ | 1 |
| 9 | 2-Cl,5-$CF_3$-Phenyl | 4-$OCH_3$-Phenyl | 4-Pyridyl | 1 | $CH_2$ | 1 |
| 10 | 2-Cl,5-F-Phenyl | Phenyl | 4-Pyridyl | 1 | $CH_2$ | 1 |
| 11 | 4-Pyridyl | Phenyl | 4-Pyridyl | 1 | $CH_2$ | 1 |
| 12 | 2-Cl,5-$CF_3$-Phenyl | 4-$CF_3$—Ph | 4-Pyridyl | 1 | $CH_2$ | 1 |
| 13 | 2-Cl,5-$CF_3$-Phenyl | Phenyl | 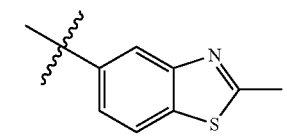 [SMILES: *c1ccc2sc(C)nc2c1] | 1 | — | 0 |
| 14 | 2-Cl,5-$CF_3$-Phenyl | Phenyl | Phenyl | 1 | $CH_2$ | 1 |
| 15 | 2-Cl,5-$CF_3$-Phenyl | Phenyl | 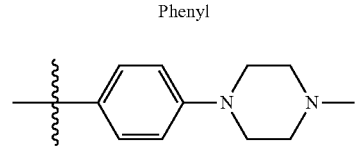 | 1 | $CH_2$ | 1 |

TABLE 1-continued

| Example | R¹ | R² | R³ | n | L¹ | X |
|---|---|---|---|---|---|---|
| 16 | 2-Cl,5-CF₃-Phenyl | Phenyl | 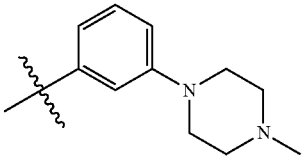 [SMILES: *c1cccc(N2CCN(C)CC2)c1] | 1 | CH₂ | 1 |
| 17 | 2-Cl,5-CF₃-Phenyl | Phenyl | 3-Pyridyl | 1 | CH₂ | 1 |
| 18 | 2-Cl,5-CF₃-Phenyl | Phenyl | 5-pyrimidinyl | 1 | CH₂ | 1 |
| 19 | 2-Cl,5-CF₃-Phenyl | Phenyl | 4-pyrimidinyl | 1 | CH₂ | 1 |
| 20 | 2-Cl,5-CF₃-Phenyl | Phenyl | 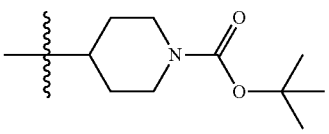 | 1 | CH₂ | 1 |
| 21 | 2-Cl,5-CF₃-Phenyl | Phenyl | 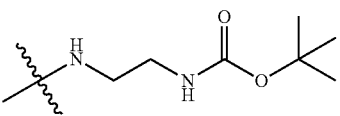 [SMILES: *NCCNC(=O)OC(C)(C)C] | 1 | CH₂ | 1 |
| 22 | 2-Cl,5-CF₃-Phenyl | Phenyl | 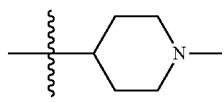 [SMILES: *C1CCN(C)CC1] | 1 | CH₂ | 1 |
| 23 | 2-Cl,5-CF₃-Phenyl | Phenyl | 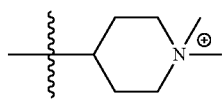 | 1 | CH₂ | 1 |

Exemplary embodiments include compounds having the formula (VI) or a pharmaceutically acceptable salt form thereof:

Exemplary embodiments include compounds having the formula (VII) or a pharmaceutically acceptable salt form thereof:

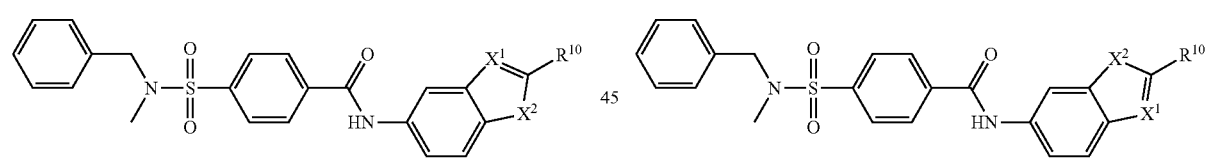

wherein non-limiting examples of $R^{10}$, $X^1$ and $X^2$ are defined herein below in Table 2.

wherein non-limiting examples of $R^{10}$, $X^1$ and $X^2$ are defined herein below in Table 3.

TABLE 2

| Example | R¹⁰ | X¹ | X² |
|---|---|---|---|
| 1 | CH₃ | N | O |
| 2 | H | N | NH |
| 3 | H | N | O |
| 4 | Cyclopropyl | N | O |
| 5 | H | N | S |
| 6 | Cyclopropyl | N | S |
| 7 | CH₃ | N | NH |
| 8 | Cyclopropyl | N | NH |
| 9 | CH₃ | CH | NH |
| 10 | Cyclopropyl | CH | NH |
| 11 | CH₃ | N | S |

TABLE 3

| Example | R¹⁰ | X¹ | X² |
|---|---|---|---|
| 1 | CH₃ | N | O |
| 2 | H | N | NH |
| 3 | H | N | O |
| 4 | Cyclopropyl | N | O |
| 5 | H | N | S |
| 6 | Cyclopropyl | N | S |
| 7 | CH₃ | N | NH |
| 8 | Cyclopropyl | N | NH |
| 9 | CH₃ | CH | NH |
| 10 | Cyclopropyl | CH | NH |
| 11 | CH₃ | N | S |

Exemplary embodiments include compounds having the formula (VIII) or a pharmaceutically acceptable salt form thereof:

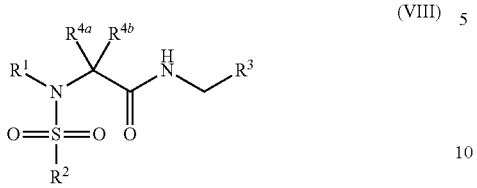

(VIII)

wherein non-limiting examples of $R^1$, $R^2$, $R^3$, $R^{4a}$, and $R^{4b}$ are defined herein below in Table 4.

TABLE 4

| Example | $R^1$ | $R^2$ | $R^3$ | $R^{4a}$ | $R^{4b}$ |
|---|---|---|---|---|---|
| 1 | 2-Cl,5-CF$_3$-Phenyl | phenyl | 4-pyridyl | CH$_3$ | H |
| 2 | 2-Cl,5-CF$_3$-Phenyl | phenyl | 4-pyridyl | H | CH$_3$ |

Exemplary embodiments include compounds having the formula (Ib) or a pharmaceutically acceptable salt form thereof:

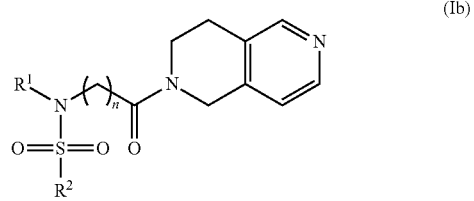

(Ib)

wherein non-limiting examples of $R^1$, $R^2$, and n are defined herein below in Table 5.

TABLE 5

| Example | $R^1$ | $R^2$ | n |
|---|---|---|---|
| 1 | 2-Cl,5-CF$_3$-Phenyl | phenyl | 1 |

Exemplary embodiments include compounds having the formula (Ic) or a pharmaceutically acceptable salt form thereof:

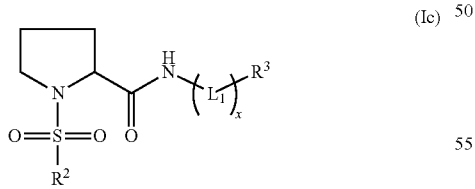

(Ic)

wherein non-limiting examples of $R^2$, $R^3$, $L_1$ and x are defined herein below in Table 6.

TABLE 6

| Example | $R^2$ | $R^3$ | $L_1$ | X |
|---|---|---|---|---|
| 1 | Phenyl | 4-pyridyl | CH$_2$ | 1 |

Exemplary embodiments include compounds having the formula (Id) or a pharmaceutically acceptable salt form thereof:

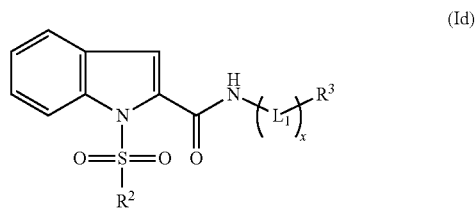

(Id)

wherein non-limiting examples of $R^2$, $R^3$, $L_1$ and x are defined herein below in Table 7.

TABLE 7

| Example | $R^2$ | $R^3$ | $L_1$ | X |
|---|---|---|---|---|
| 1 | Phenyl | 4-pyridyl | CH$_2$ | 1 |

Exemplary embodiments include compounds having the formula (IV) or a pharmaceutically acceptable salt form thereof:

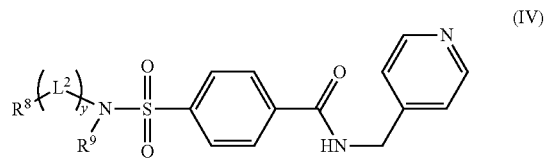

(IV)

wherein non-limiting examples of $R^8$, $R^9$, $L_2$ and y are defined herein below in Table 8.

TABLE 8

| Example | $R^8$ | $R^9$ | $L_2$ | Y |
|---|---|---|---|---|
| 1 | Phenyl | CH$_3$ | CH$_2$ | 1 |

Exemplary embodiments include compounds having the formula (V) or a pharmaceutically acceptable salt form thereof:

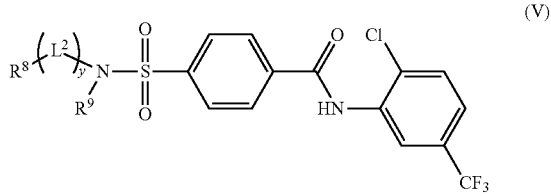

(V)

wherein non-limiting examples of $R^8$, $R^9$, $L_2$ and y are defined herein below in Table 9.

TABLE 9

| Example | $R^8$ | $R^9$ | $L_2$ | Y |
|---|---|---|---|---|
| 1 | Phenyl | CH$_3$ | CH$_2$ | 1 |

For the purposes of demonstrating the manner in which the compounds of the present invention are named and referred to herein, the compound having the formula:

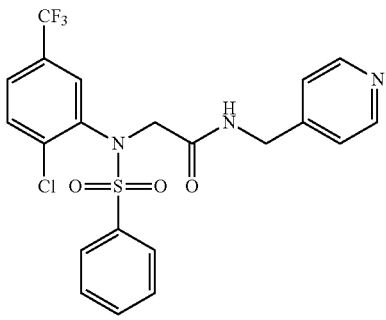 [SMILES: O=C(CN(c1cc(C(F)(F)F)ccc1Cl)S(=O)(=O)c1ccccc1)NCc1ccncc1]

has the chemical name 2-[Benzenesulfonyl-(2-chloro-5-trifluoromethyl-phenyl)-amino]-N-pyridin-4-ylmethyl-acetamide.

For the purposes of demonstrating the manner in which the compounds of the present invention are named and referred to herein, the compound having the formula:

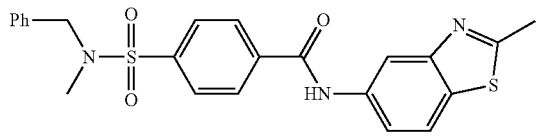 [SMILES: Cc1nc2cc(NC(=O)c3ccc(S(=O)(=O)N(C)Cc4ccccc4)cc3)ccc2s1]

has the chemical name 4-(Benzyl-methyl-sulfamoyl)-N-(2-methyl-benzothiazol-5-yl)-benzamide.

For the purposes of the present invention, a compound depicted by the racemic formula will stand equally well for either of the two enantiomers or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the covalently closed circular DNA inhibitors of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in Scheme 1.

Scheme 1

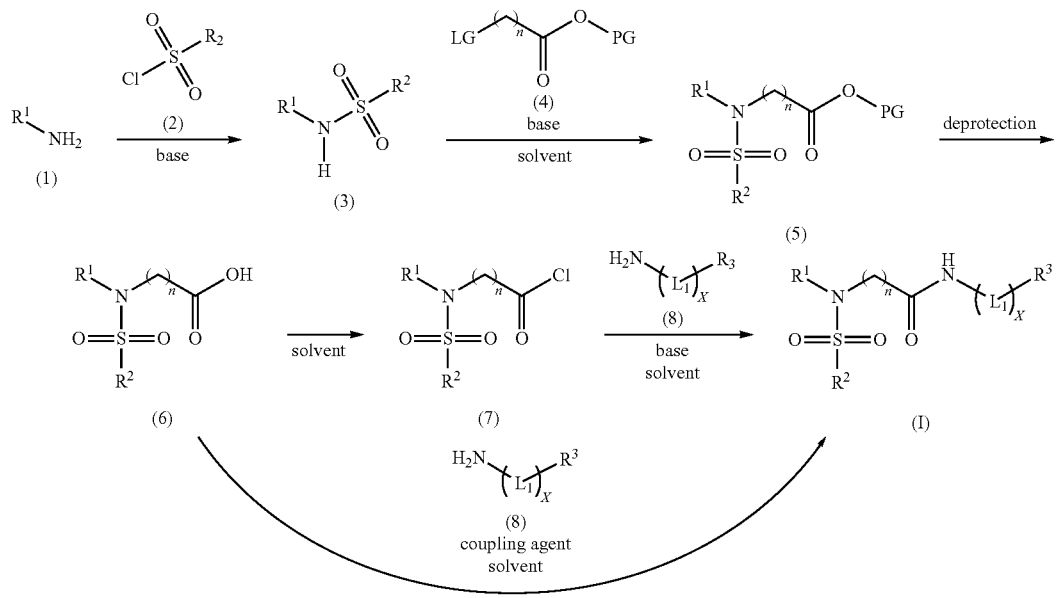

Accordingly, a suitably substituted compound, $R^1$—$NH_2$ (1), a known compound or compound prepared by known methods, is reacted with a suitably substituted compound $R^2SO_2Cl$ (2) in the presence of a base such as pyridine, triethyl amine, diisopropylethylamine and the like, optionally in an organic solvent such as tetrahydrofuran, diethyl ether, methylene chloride and the like, to provide the compound of the formula (3). The compound of the formula (3) is then reacted with a base such as sodium hydride, n-butyl lithium, or isopropylmagnesium chloride and the like in an organic solvent like tetrahydrofuran, diethyl ether, 1-4 dioxane, methylene chloride, N,N-dimethylformamide, and the like, to give the corresponding metalated species. This is then reacted with a compound of the formula (4), wherein PG is a protecting group and LG is a suitable leaving group such as chloride, bromide, iodide, methansulfonate, and the like, in an organic solvent like tetrahydrofuran, diethyl ether 1-4 dioxane, methylene chloride, N,N-dimethylformamide, and the like, to provide compounds of the formula (5). The protecting group can be remove by treatment under suitable conditions such as 1) with acid, such as hydrogen chloride, trifluoroacetic acid, and the like in organic solvent such as 1,4-dioxane, dichloromethane, and the like, or 2) hydrogen in the presence of a catalyst such as palladium on activated carbon, platinum oxide and the like in an organic solvent such as ethyl acetate, methanol, ethanol or 3) base such as lithium hydroxide, sodium hydroxide, potassium carbonate and the like in a solvent like water, methanol, tetrahydrofuran and the like to provide compounds of the formula (6).

A compound of formula (6) can then be converted into a compound of formula (I) via multiple pathways.

A compound of formula (6) can be reacted with thionyl chloride or oxalyl chloride, optionally in an organic solvent such as methylene chloride, tetrahydrofuran, 1,4-dioxane and the like, and optionally in the presence of N, N-dimethylforamide, to provide a compound of the formula (7). A compound of the formula (7) is then reacted with a compound of the formula (8) in the presence of a base such as pyridine, triethyl amine, diisopropylethylamine and the like, in an organic solvent such as tetrahydrofuran, diethyl ether and the like, to provide compounds of the formula (I).

Alternatively, a compound of formula (6) can be reacted with a compound of the formula (8) in the presence of a coupling agent such as 1-ethyl-3-(3-dimethylaminopropyl) carbodiimide, N,N'-Dicyclohexylcarbodiimide, 2-(7-Aza-1H-benzotriazole-1-yl)-1,1,3,3-tetramethyluronium hexafluorophosphate and the like, in an organic solvent such as methylene chloride, tetrahydrofuran, 1,4-dioxane, dimethylforamide and the like, optionally in the presence of a base such as pyridine, triethyl amine, diisopropylethylamine and the like, to provide a compound of the formula (I).

Scheme 2

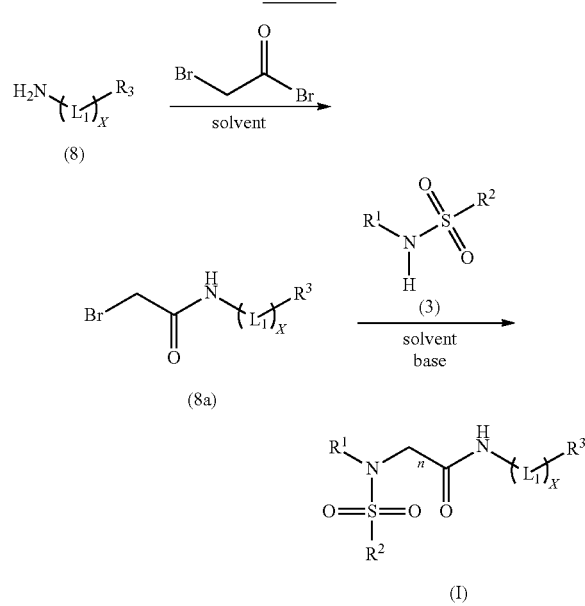

Alternatively, a compound of the formula (I) may be prepared according to scheme 2. Thus, a compound of formula (8) can be reacted with bromoacetyl bromide in an organic solvent such as methylene chloride, tetrahydrofuran, 1,4-dioxane, dimethylforamide and the like, in the presence of a base such as pyridine, triethyl amine, diisopropylethylamine and the like, to provide a compound of the formula (8a). A compound of the formula (8a) is then reacted with a compound of the formula (3) in the presence of a base such as potassium carbonate, sodium carbonate, lithium carbonate, and the like, in an organic solvent such as acetonitrile, methanol, ethanol, tetrahydrofuran, 1,4-dioxane, N,N-dimethylformamide, and the like, optionally with heating, optionally with microwave irradiation to provide a compound of the formula (I).

Compounds of formula (Ia) may be prepared according to the process outlined in Scheme 3.

protecting group can be remove by treatment under suitable conditions such as 1) with acid, such as hydrogen chloride, trifluoroacetic acid, and the like in organic solvent such as 1,4-dioxane, dichloromethane, and the like, or 2) hydrogen in the presence of a catalyst such as palladium on activated carbon, platinum oxide and the like in an organic solvent such as ethyl acetate, methanol, ethanol or 3) base such as lithium hydroxide, sodium hydroxide, potassium carbonate and the like in a solvent like water, methanol, tetrahydrofuran and the like to provide compounds of the formula (6a).

A compound of formula (6a) can then be converted into a compound of formula (Ia) via multiple pathways.

A compound of formula (6a) can be reacted with thionyl chloride or oxalyl chloride, optionally in an organic solvent such as methylene chloride, tetrahydrofuran, 1,4-dioxane and the like, and optionally in the presence of N, N-dim-

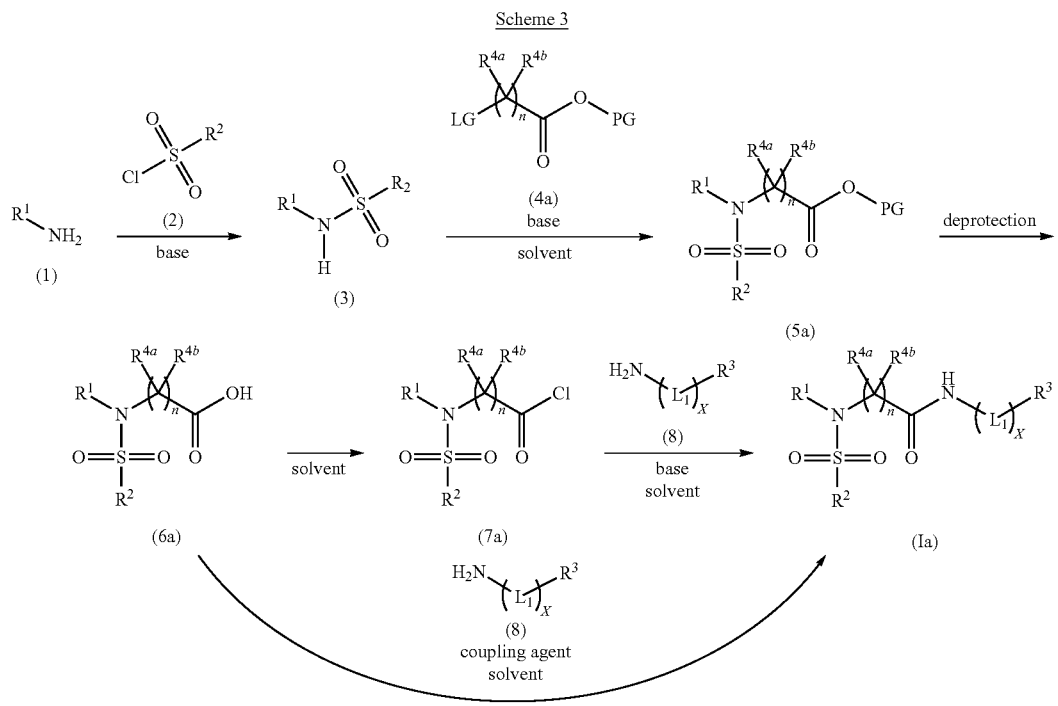

Scheme 3

Accordingly, a suitably substituted compound, $R^1$—$NH_2$ (1), a known compound or compound prepared by known methods, is reacted with a suitably substituted compound $R^2SO_2Cl$ (2) in the presence of a base such as pyridine, triethyl amine, diisopropylethylamine and the like, optionally in an organic solvent such as tetrahydrofuran, diethyl ether, methylene chloride and the like, to provide the compound of the formula (3). The compound of the formula (3) is then reacted with a base such as sodium hydride, n-butyl lithium, or isopropylmagnesium chloride and the like in an organic solvent like tetrahydrofuran, diethyl ether and the like, to give the corresponding metalated species. This is then reacted with a compound of the formula (4a), wherein PG is a protecting group and LG is a suitable leaving group such as chloride, bromide, iodide, methansulfonate, and the like, in an organic solvent like tetrahydrofuran, diethyl ether, 1-4 dioxane, methylene chloride, N,N-dimethylformamide, and the like, to provide compounds of the formula (5a). The ethylforamide, to provide a compound of the formula (7a). A compound of the formula (7a) is then reacted with a compound of the formula (8) in the presence of a base such as pyridine, triethyl amine, diisopropylethylamine and the like, in an organic solvent such as tetrahydrofuran, diethyl ether and the like, to provide compounds of the formula (Ia).

Alternatively, a compound of formula (6a) can be reacted with a compound of formula (8) in the presence of a coupling agent such as 1-ethyl-3-(3-dimethylaminopropyl) carbodiimide, N,N'-Dicyclohexylcarbodiimide, 2-(7-Aza-1H-benzotriazole-1-yl)-1,1,3,3-tetramethyluronium hexafluorophosphate and the like, in an organic solvent such as methylene chloride, tetrahydrofuran, 1,4-dioxane, dimethylforamide and the like, optionally in the presence of a base such as pyridine, triethyl amine, diisopropylethylamine and the like, to provide a compound of the formula (Ia).

Compounds of formula (Ib) may be prepared according to the process outlined in Scheme 4.

Scheme 4

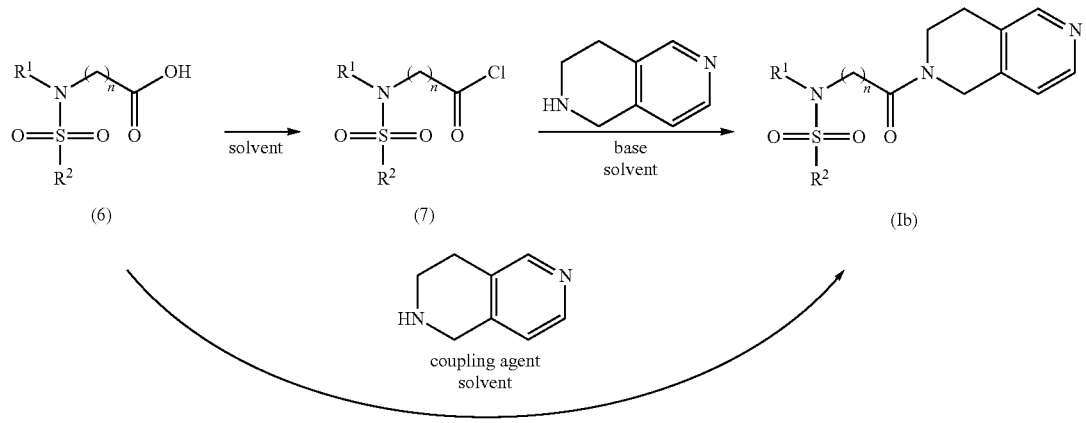

A compound of formula (6) can be reacted with thionyl chloride or oxalyl chloride, optionally in an organic solvent such as methylene chloride, tetrahydrofuran, 1,4-dioxane and the like, and optionally in the presence of N, N-dimethylforamide, to provide a compound of the formula (7). A compound of the formula (7) is then reacted with 1,2,3,4-tetrahydro-[2,6]naphthyridine in the presence of a base such as pyridine, triethyl amine, diisopropylethylamine and the like, in an organic solvent such as tetrahydrofuran, diethyl ether and the like, to provide compounds of the formula (Ib).

Alternatively, a compound of formula (6) can be reacted with 1,2,3,4-tetrahydro-[2,6]naphthyridine in the presence of a coupling agent such as 1-ethyl-3-(3-dimethylaminopropyl) carbodiimide, N,N'-Dicyclohexylcarbodiimide, 2-(7-Aza-1H-benzotriazole-1-yl)-1,1,3,3-tetramethyluronium hexafluorophosphate and the like, in an organic solvent such as methylene chloride, tetrahydrofuran, 1,4-dioxane, dimethylforamide and the like, optionally in the presence of a base such as pyridine, triethyl amine, diisopropylethylamine and the like, to provide a compound of the formula (Ib).

Compounds of formula (Ic) may be prepared according to the process outlined in Scheme 5.

pyridine, triethyl amine, diisopropylethylamine and the like, optionally in an organic solvent such as tetrahydrofuran, diethyl ether, methylene chloride and the like, to provide the compound of the formula (3c).

A compound of formula (3c) can then be converted into a compound of formula (Ic) via multiple pathways.

A compound of formula (3c) can be reacted with thionyl chloride or oxalyl chloride, optionally in an organic solvent such as methylene chloride, tetrahydrofuran, 1,4-dioxane and the like, and optionally in the presence of N, N-dimethylforamide, to provide a compound of the formula (7c). A compound of the formula (7c) is then reacted with a compound of the formula (8) in the presence of a base such as pyridine, triethyl amine, diisopropylethylamine and the like, in an organic solvent such as tetrahydrofuran, diethyl ether and the like, to provide compounds of the formula (Ic).

Alternatively, a compound of formula (3c) can be reacted with a compound of the formula (8) in the presence of a coupling agent such as 1-ethyl-3-(3-dimethylaminopropyl) carbodiimide, N,N'-Dicyclohexylcarbodiimide, 2-(7-Aza-1H-benzotriazole-1-yl)-1,1,3,3-tetramethyluronium hexafluorophosphate and the like, optionally in the presence Scheme 5

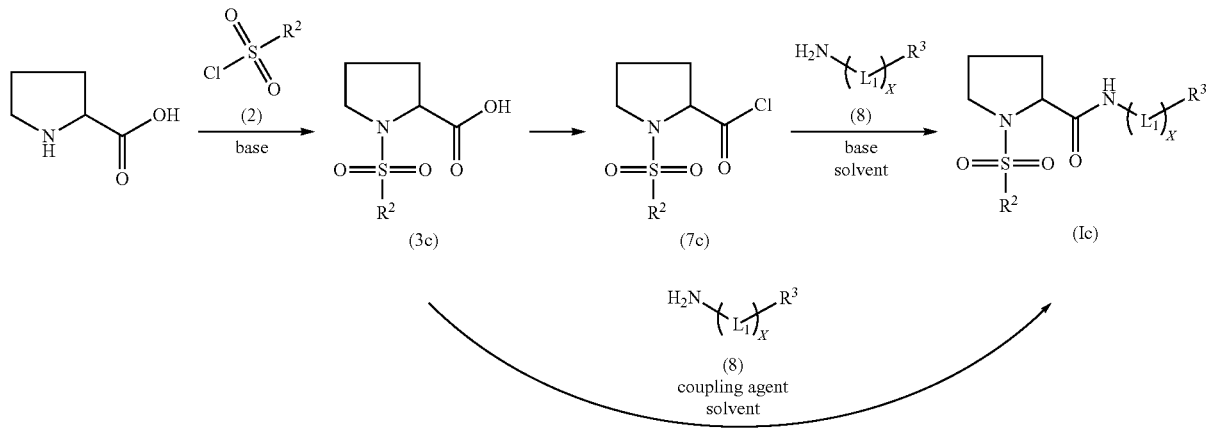

Accordingly, proline is reacted with a suitably substituted compound $R^2SO_2Cl$ (2) in the presence of a base such as of hydroxybenzotriazole, in an organic solvent such as methylene chloride, tetrahydrofuran, 1,4-dioxane, dimethylforamide and the like, optionally in the presence of a base such as pyridine, triethyl amine, diisopropylethylamine and the like, to provide a compound of the formula (Ic).

Compounds of formula (Id) may be prepared according to the process outlined in Scheme 6.

Scheme 6

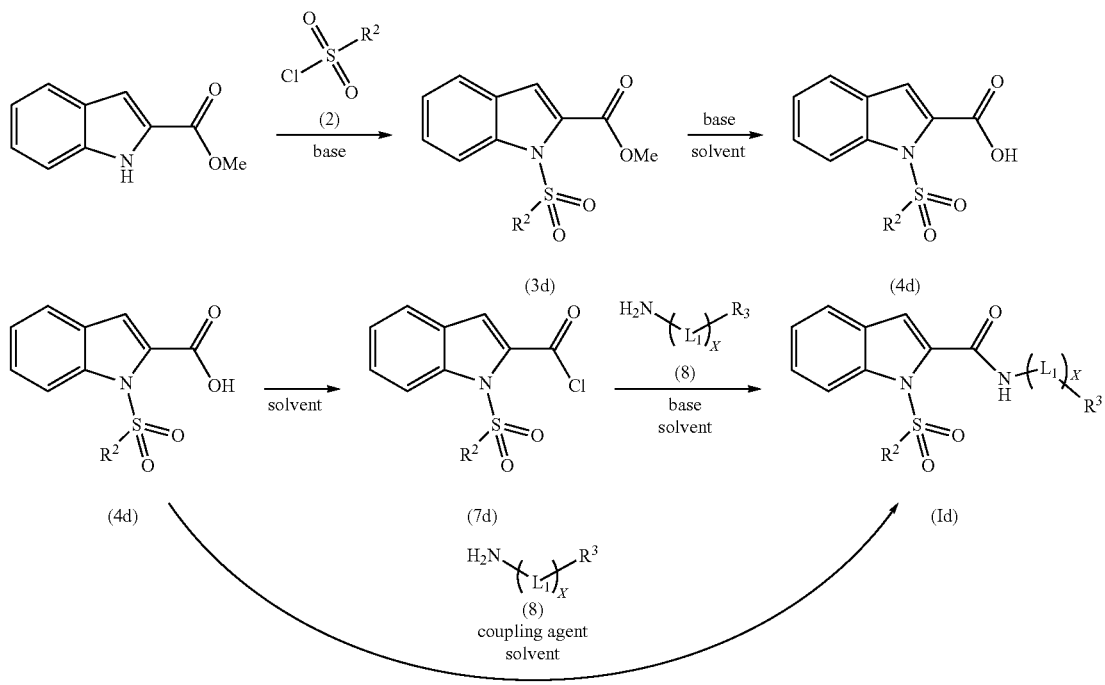

Accordingly, 1H-indole-2-carboxylic acid methyl ester is reacted with a suitably substituted compound $R^2SO_2Cl$ (2) in the presence of a base such as sodium hydride, lithium hydride, potassium hydride, butyl lithium, lithium diisopropylamide, sodium diisopropyl amide, and the like, optionally in an organic solvent such as tetrahydrofuran, 1,4-dioxane, N,N-dimethylformamide, diethyl ether, methylene chloride and the like, to provide the compound of the formula (3d). A compound of the formula (3d) is then reacted with a base such as lithium hydroxide, sodium hydroxide, potassium hydroxide, and the like, in an organic solvent such as methanol, ethanol, tetrahydrofuran, and the like, optionally in the presence of water, optionally with heating, optionally with microwave irradiation to provide a compound of the formula (4d).

A compound of formula (4d) can then be converted into a compound of formula (Id) via multiple pathways.

A compound of formula (4d) can be reacted with thionyl chloride or oxalyl chloride, optionally in an organic solvent such as methylene chloride, tetrahydrofuran, 1,4-dioxane and the like, and optionally in the presence of N, N-dimethylforamide, to provide a compound of the formula (7d). A compound of the formula (7d) is then reacted with a compound of the formula (8) in the presence of a base such as pyridine, triethyl amine, diisopropylethylamine and the like, in an organic solvent such as tetrahydrofuran, diethyl ether and the like, to provide compounds of the formula (Id).

Alternatively, a compound of formula (4d) can be reacted with a compound of the formula (8) in the presence of a coupling agent such as 1-ethyl-3-(3-dimethylaminopropyl) carbodiimide, N,N'-Dicyclohexylcarbodiimide, 2-(7-Aza-1H-benzotriazole-1-yl)-1,1,3,3-tetramethyluronium hexafluorophosphate and the like, optionally in the presence of hydroxybenzotriazole, in an organic solvent such as methylene chloride, tetrahydrofuran, 1,4-dioxane, dimethylforamide and the like, optionally in the presence of a base such as pyridine, triethyl amine, diisopropylethylamine and the like, to provide a compound of the formula (Id).

Compounds of formula (II) may be prepared according to the process outlined in Scheme 7.

Scheme 7

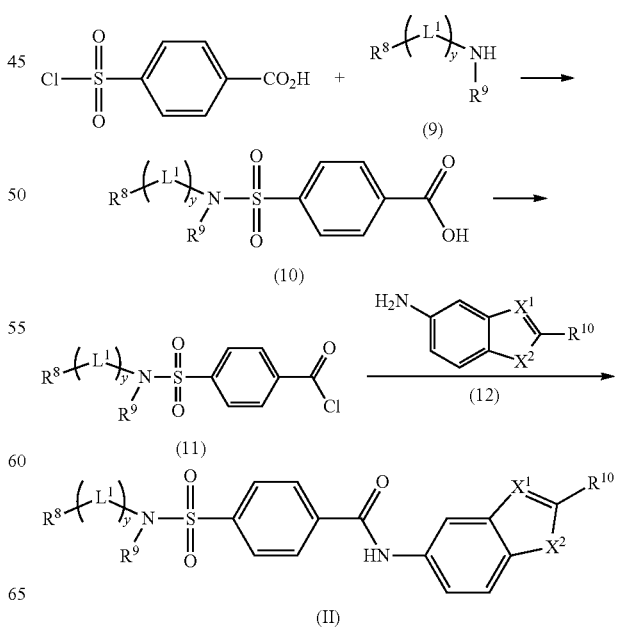

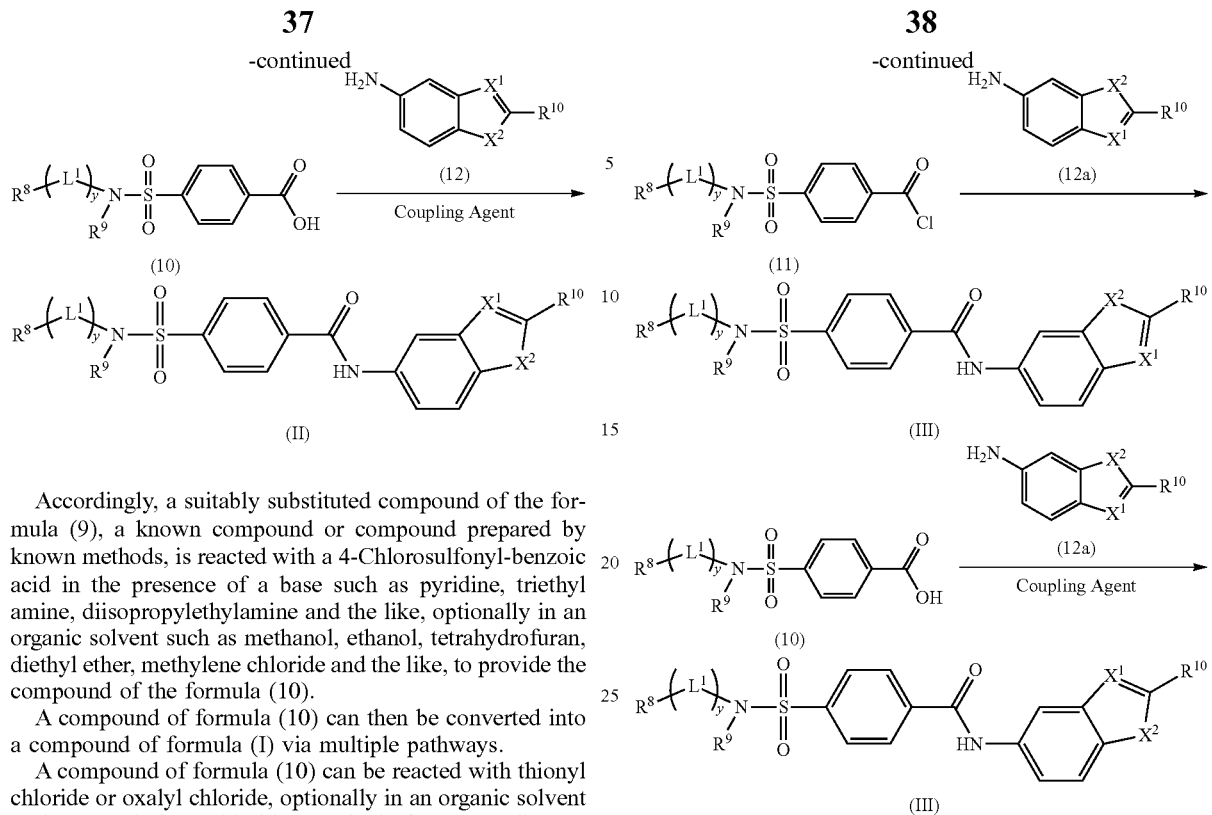

Accordingly, a suitably substituted compound of the formula (9), a known compound or compound prepared by known methods, is reacted with a 4-Chlorosulfonyl-benzoic acid in the presence of a base such as pyridine, triethyl amine, diisopropylethylamine and the like, optionally in an organic solvent such as methanol, ethanol, tetrahydrofuran, diethyl ether, methylene chloride and the like, to provide the compound of the formula (10).

A compound of formula (10) can then be converted into a compound of formula (I) via multiple pathways.

A compound of formula (10) can be reacted with thionyl chloride or oxalyl chloride, optionally in an organic solvent such as methylene chloride, tetrahydrofuran, 1,4-dioxane and the like, and optionally in the presence of N, N-dimethylforamide, to provide a compound of the formula (11). A compound of the formula (11) is then reacted with a compound of the formula (12), a known compound or compound prepared by known methods, in the presence of a base such as pyridine, triethyl amine, diisopropylethylamine and the like, in an organic solvent such as tetrahydrofuran, diethyl ether, methylene chloride and the like, to provide compounds of the formula (II).

Alternatively, a compound of formula (10) can be reacted with a compound of the formula (12), a known compound or compound prepared by known methods, in the presence of a coupling agent such as 1-ethyl-3-(3-dimethylaminopropyl) carbodiimide, N,N'-Dicyclohexylcarbodiimide, 2-(7-Aza-1H-benzotriazole-1-yl)-1,1,3,3-tetramethyluronium hexafluorophosphate and the like, in an organic solvent such as methylene chloride, tetrahydrofuran, 1,4-dioxane, dimethylforamide and the like, optionally in the presence of a base such as pyridine, triethyl amine, diisopropylethylamine and the like, to provide a compound of the formula (II).

Compounds of formula (1H) may be prepared according to the process outlined in Scheme 8.

Scheme 8

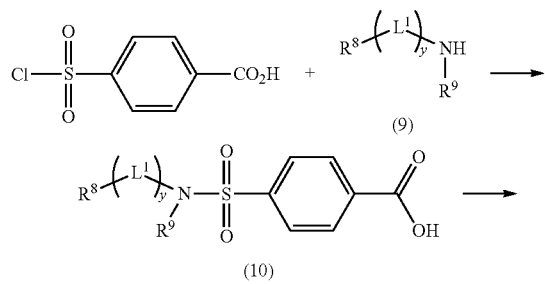

Accordingly, a suitably substituted compound of the formula (9), a known compound or compound prepared by known methods, is reacted with a 4-Chlorosulfonyl-benzoic acid in the presence of a base such as pyridine, triethyl amine, diisopropylethylamine and the like, optionally in an organic solvent such as methanol, ethanol, tetrahydrofuran, diethyl ether, methylene chloride and the like, to provide the compound of the formula (10).

A compound of formula (10) can then be converted into a compound of formula (III) via multiple pathways.

A compound of formula (10) can be reacted with thionyl chloride or oxalyl chloride, optionally in an organic solvent such as methylene chloride, tetrahydrofuran, 1,4-dioxane and the like, and optionally in the presence of N, N-dimethylforamide, to provide a compound of the formula (11). A compound of the formula (11) is then reacted with a compound of the formula (12a), a known compound or compound prepared by known methods, in the presence of a base such as pyridine, triethyl amine, diisopropylethylamine and the like, in an organic solvent such as tetrahydrofuran, diethyl ether, methylene chloride and the like, to provide compounds of the formula (III).

Alternatively, a compound of formula (10) can be reacted with a compound of the formula (12a), a known compound or compound prepared by known methods, in the presence of a coupling agent such as 1-ethyl-3-(3-dimethylaminopropyl) carbodiimide, N,N'-Dicyclohexylcarbodiimide, 2-(7-Aza-1H-benzotriazole-1-yl)-1,1,3,3-tetramethyluronium hexafluorophosphate and the like, in an organic solvent such as methylene chloride, tetrahydrofuran, 1,4-dioxane, dimethylforamide and the like, optionally in the presence of a base such as pyridine, triethyl amine, diisopropylethylamine and the like, to provide a compound of the formula (III).

Compounds of formula (IV) may be prepared according to the process outlined in Scheme 9.

Scheme 9

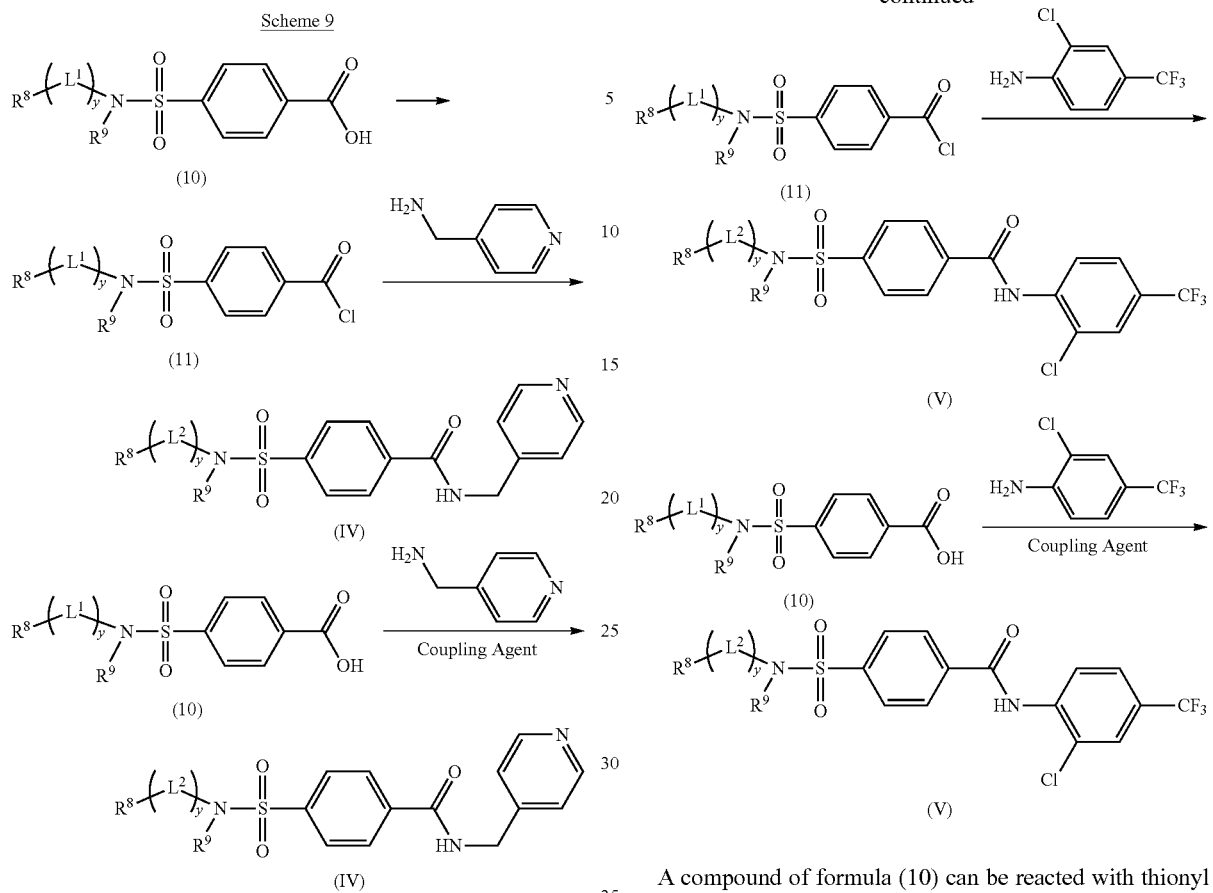

A compound of formula (10) can be reacted with thionyl chloride or oxalyl chloride, optionally in an organic solvent such as methylene chloride, tetrahydrofuran, 1,4-dioxane and the like, and optionally in the presence of N, N-dimethylforamide, to provide a compound of the formula (11). A compound of the formula (11) is then reacted with pyridin-4-yl-methylamine in the presence of a base such as pyridine, triethyl amine, diisopropylethylamine and the like, in an organic solvent such as tetrahydrofuran, diethyl ether, methylene chloride and the like, to provide compounds of the formula (IV).

Alternatively, a compound of formula (10) can be reacted with pyridin-4-yl-methylamine in the presence of a coupling agent such as 1-ethyl-3-(3-dimethylaminopropyl) carbodiimide, N,N'-Dicyclohexylcarbodiimide, 2-(7-Aza-1H-benzotriazole-1-yl)-1,1,3,3-tetramethyluronium hexafluorophosphate and the like, optionally in the presence of hydroxybenzotriazole, in an organic solvent such as methylene chloride, tetrahydrofuran, 1,4-dioxane, dimethylforamide and the like, optionally in the presence of a base such as pyridine, triethyl amine, diisopropylethylamine and the like, to provide a compound of the formula (IV).

Compounds of formula (V) may be prepared according to the process outlined in Scheme 10.

Scheme 10

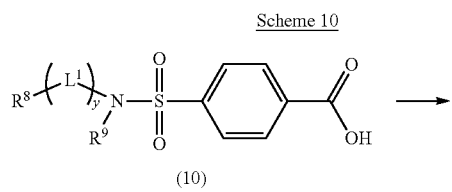

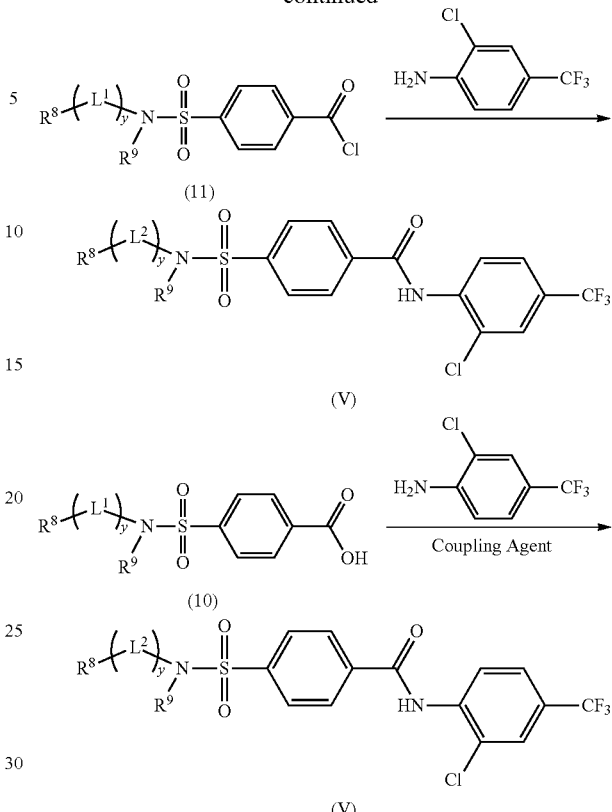

A compound of formula (10) can be reacted with thionyl chloride or oxalyl chloride, optionally in an organic solvent such as methylene chloride, tetrahydrofuran, 1,4-dioxane and the like, and optionally in the presence of N, N-dimethylforamide, to provide a compound of the formula (11). A compound of the formula (11) is then reacted with 2-chloro-4-trifluoromethyl-phenylamine in the presence of a base such as pyridine, triethyl amine, diisopropylethylamine and the like, in an organic solvent such as tetrahydrofuran, diethyl ether, methylene chloride and the like, to provide compounds of the formula (V).

Alternatively, a compound of formula (10) can be reacted with 2-chloro-4-trifluoromethyl-phenylamine in the presence of a coupling agent such as 1-ethyl-3-(3-dimethylaminopropyl) carbodiimide, N,N'-Dicyclohexylcarbodiimide, 2-(7-Aza-1H-benzotriazole-1-yl)-1,1,3,3-tetramethyluronium hexafluorophosphate and the like, optionally in the presence of hydroxybenzotriazole, in an organic solvent such as methylene chloride, tetrahydrofuran, 1,4-dioxane, dimethylforamide and the like, optionally in the presence of a base such as pyridine, triethyl amine, diisopropylethylamine and the like, to provide a compound of the formula (V).

The examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H-NMR spectra were obtained on a Varian Mercury 300-MHz NMR. Purity (%) and mass spectral data were determined with a Waters Alliance 2695 HPLC/MS (Waters Symmetry C18, 4.6×75 mm, 3.5 μm) with a 2996 diode array detector from 210-400 nm.

EXAMPLES

The examples provided below provide representative methods for preparing exemplary compounds of the present invention. The skilled practitioner will know how to substitute the appropriate reagents, starting materials and purification methods known to those skilled in the art, in order to prepare the compounds of the present invention.

The examples provide methods for preparing representative compounds of the disclosure. The skilled practitioner will know how to substitute the appropriate reagents, starting materials and purification methods known to those skilled in the art, in order to prepare additional compounds of the present invention.

Example 1

Synthesis of 2-[Benzenesulfonyl-(2-chloro-5-trifluoromethyl-phenyl)-amino]-N-pyridin-4-ylmethyl-acetamide

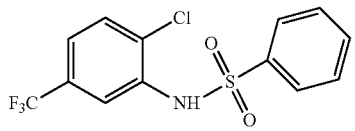 [SMILES: O=S(=O)(Nc1cc(C(F)(F)F)ccc1Cl)c1ccccc1]

Synthesis of N-(2-Chloro-5-trifluoromethyl-phenyl)-benzenesulfonamide

To a solution of 2-Chloro-5-trifluoromethyl-phenylamine (0.41 mL, 3 mmol) in pyridine (5 ml), was added dropwise of benzenesulfonyl chloride (0.44 mL, 3 mmol) at 0° C. After addition, the reaction was stirred at 0° C. for 2 hours. Then, the reaction was quenched with 2 N HCl at 0° C., and the resulting solution was extracted with ethyl acetate. The combined organic layer was washed with brine, dried with $Na_2SO_4$, filtered and concentrated to give the crude product. Purification by silica gel chromatography (Ethyl acetate/Hexane) provided 0.677 g (65%) of N-(2-Chloro-5-trifluoromethyl-phenyl)-benzenesulfonamide.

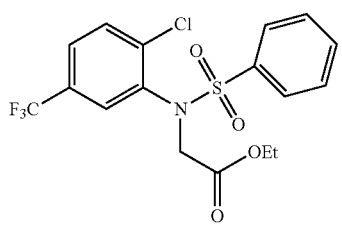

Synthesis of [Benzenesulfonyl-(2-chloro-5-trifluoromethyl-phenyl)-amino]-acetic acid ethyl ester N-(2-Chloro-5-trifluoromethyl-phenyl)-benzenesulfonamide (0.655 g, 1.95 mmol) in tetrahydrofuran was cooled to 0° C. and 60% NaH (0.156 g, 3.9 mmol) was added. The mixture was stirred at this temperature for half hour, followed by addition of bromo-acetic acid ethyl ester (0.49 g, 2.925 mmol). The mixture was stirred at room temperature overnight, then quenched with saturated aqueous $NH_4Cl$, and extracted with Ethyl acetate. The combined organic layers were washed with $H_2O$, saturated aqueous NaCl, dried over $Na_2SO_4$, filtered and concentrated to give the crude product. Purification by silica gel chromatography (Ethyl acetate/Hexane) provided 0.756 g (92%) of [Benzenesulfonyl-(2-chloro-5-trifluoromethyl-phenyl)-amino]-acetic acid ethyl ester.

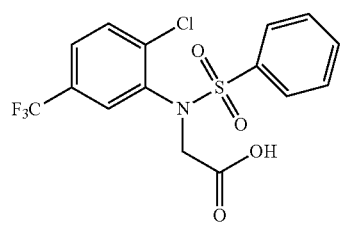 [SMILES: O=C(O)CN(c1cc(C(F)(F)F)ccc1Cl)S(=O)(=O)c1ccccc1]

Synthesis of [Benzenesulfonyl-(2-chloro-5-trifluoromethyl-phenyl)-amino]-acetic acid

[Benzenesulfonyl-(2-chloro-5-trifluoromethyl-phenyl)-amino]-acetic acid ethyl ester (0.756 g, 0.00179 mmol) and LiOH (0.376 g, 0.00896 mmol) were stirred in a solution of 1,4-dioxane/$H_2O$ (9/1) at room temperature overnight. After acidic workup (5% HCl), the mixture was extracted with Ethyl acetate, dried over $Na_2SO_4$, filtered and concentrated to give the crude product. Purification by silica gel chromatography (Ethyl acetate/Hexane) provided 0.595 g (84%) of [Benzenesulfonyl-(2-chloro-5-trifluoromethyl-phenyl)-amino]-acetic acid.

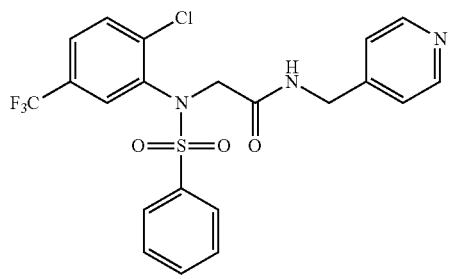 [SMILES: O=C(CN(c1cc(C(F)(F)F)ccc1Cl)S(=O)(=O)c1ccccc1)NCc1ccncc1]

Synthesis of 2-[Benzenesulfonyl-(2-chloro-5-trifluoromethyl-phenyl)-amino]-N-pyridin-4-ylmethyl-acetamide

[Benzenesulfonyl-(2-chloro-5-trifluoromethyl-phenyl)-amino]-acetic acid (0.38 g, 0.96 mmol) in thionyl chloride (10 mL) was heated to 80° C. overnight. The reaction was cooled and the solvent was evaporated to dryness. The residue was re-dissolved in tetrahydrofuran, pyridin-4-ylmethylamine (0.16 g, 1.46 mmol) was added, followed by diisopropylethyl amine (1 mL). The mixture was stirred at room temperature overnight and the resulting precipitate was collected by filtration to provide the crude product. The crude product was purified via re-crystallization and trituration with ethyl acetate, hexane, and ethyl ether to provided 0.32 g (67%) of 2-[Benzenesulfonyl-(2-chloro-5-trifluoromethyl-phenyl)-amino]-N-pyridin-4-ylmethyl-acetamide.

Example 2

Synthesis of 2-[(2-Chloro-5-trifluoromethyl-phenyl)-(toluene-4-sulfonyl)-amino]-N-pyridin-4-ylmethyl-acetamide

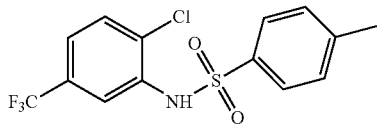 [SMILES: Cc1ccc(S(=O)(=O)Nc2cc(C(F)(F)F)ccc2Cl)cc1]

Synthesis of N-(2-Chloro-5-trifluoromethyl-phenyl)-4-methyl-benzene sulfonamide

To a solution of 2-chloro-5-trifluoromethylaniline (585 mg, 3 mmol) in pyridine (5 ml) added was dropwise at 0° C. 4-methylbenzenesulfonyl chloride (570 mg, 3 mmol). After addition, the mixture was stirred at the same temperature for two hours and then quenched with 2N HCl. The acidic mixture was extracted with ethyl acetate three times. The combined organic solvent was dried over sodium sulfate, filtered and concentrated to give 0.98 g crude product, which was purified by silica gel chromatography (30-50% ethyl acetate in hexane) to afford 0.94 g of N-(2-Chloro-5-trifluoromethyl-phenyl)-4-methyl-benzene sulfonamide.

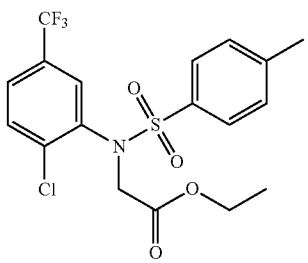 [SMILES: CCOC(=O)CN(c1cc(C(F)(F)F)ccc1Cl)S(=O)(=O)c1ccc(C)cc1]

Synthesis of [(2-Chloro-5-trifluoromethyl-phenyl)-(toluene-4-sulfonyl)-amino]-acetic acid ethyl ester To a solution of N-(2-Chloro-5-trifluoromethyl-phenyl)-4-methyl-benzene sulfonamide. (130 mg, 0.37 mmol) in 2 mL of N,N-dimethylformamide was added ethyl bromoacetate (93 mg, 0.56 mmol) and potassium carbonate (154 mg, 1.1 mmol). The mixture was heated at 60° C. for 30 minutes. The mixture was diluted with 50 ml ethyl acetate and washed with water and brine. The organic solution was dried over Na$_2$SO$_4$, filtered and concentrated to give 150 mg [(2-Chloro-5-trifluoromethyl-phenyl)-(toluene-4-sulfonyl)-amino]-acetic acid ethyl ester which was used without further purification.

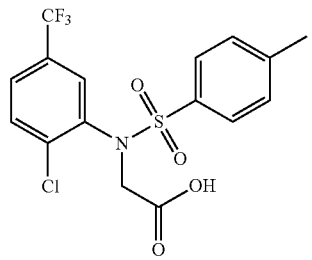 [SMILES: Cc1ccc(S(=O)(=O)N(CC(=O)O)c2cc(C(F)(F)F)ccc2Cl)cc1]

Synthesis of [(2-Chloro-5-trifluoromethyl-phenyl)-(toluene-4-sulfonyl)-amino]-acetic acid To a solution of [(2-Chloro-5-trifluoromethyl-phenyl)-(toluene-4-sulfonyl)-amino]-acetic acid ethyl ester in 4 ml of methanol was added 1 ml water and 0.8 ml 5N NaOH (4 mmol). The mixture was stirred at room temperature for 2 hours, and then the solvents were removed under vacuum. The residual material was partitioned between 100 ml of ethyl acetate and 100 mL of 2N HCl. The organic phase was washed with brine and dried over Na$_2$SO$_4$. The solution was then filtered and stripped of solvent to provide 100 mg of [(2-Chloro-5-trifluoromethyl-phenyl)-(toluene-4-sulfonyl)-amino]-acetic acid, which was used without further purification.

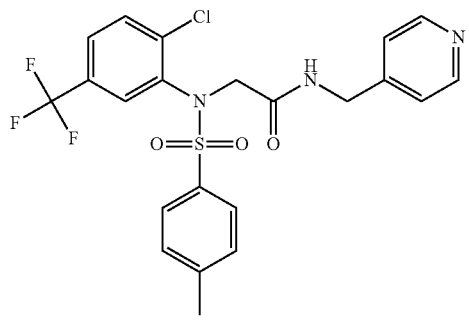 [SMILES: Cc1ccc(S(=O)(=O)N(CC(=O)NCc2ccncc2)c2cc(C(F)(F)F)ccc2Cl)cc1]

Synthesis of 2-[(2-Chloro-5-trifluoromethyl-phenyl)-(toluene-4-sulfonyl)-amino]-N-pyridin-4-ylmethyl-acetamide To a solution of [(2-Chloro-5-trifluoromethyl-phenyl)-(toluene-4-sulfonyl)-amino]-acetic acid in 2 mL N,N-dimethylformamide was added 4-aminomethylpyridine (45 mg, 0.42 mmol), N,N,N',N'-Tetramethyl-O-(1H-benzotriazol-1-yl)uronium hexafluorophosphate (HBTU, 212 mg, 0.56 mmol) and triethylamine (113 mg, 1.12 mmol). After 10 minutes, the reaction was diluted with 100 ml ethyl acetate and washed with water (×5) and brine. The organic solvent was then dried over sodium sulfate, filtered and stripped of solvent. The residual material was purified by silica gel chromatography (eluted with 30-50% ethyl acetate in hexane) to afford 40 mg 2-[(2-Chloro-5-trifluoromethyl-phenyl)-(toluene-4-sulfonyl)-amino]-N-pyridin-4-ylmethyl-acetamide. LC/MS: 498 (M+H). $^1$H-NMR (CDCl$_3$, ppm): 8.42 (s, broad, 1H), 7.45 (m, 4H), 7.23 (d, 2H), 7.19 (s, 1H), 7.04 (m, 4H), 4.42 (d, 2H), 4.18 (s, 2H), 2.18 (s, 3H).

The following compounds can be prepared by the procedure of 2-[(2-Chloro-5-trifluoromethyl-phenyl)-(toluene-4-sulfonyl)-amino]-N-pyridin-4-ylmethyl-acetamide. The skilled practitioner will know how to substitute the appropriate reagents, starting materials and purification methods known to those skilled in the art, in order to prepare the compounds provided herein.

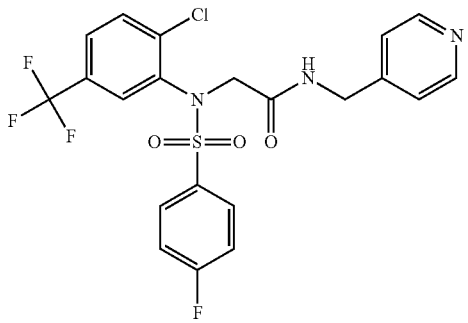 [SMILES: O=C(CN(c1cc(C(F)(F)F)ccc1Cl)S(=O)(=O)c1ccc(F)cc1)NCc1ccncc1]

Example 3

Synthesis of 2-[(2-Chloro-5-trifluoromethyl-phenyl)-(4-fluoro-benzenesulfonyl)-amino]-N-pyridin-4-ylmethyl-acetamide The title compound was prepared according to the procedure for 2-[(2-Chloro-5-trifluoromethyl-phenyl)-(toluene-4-sulfonyl)-amino]-N-pyridin-4-ylmethyl-acetamide except 4-fluorobenzenesulfonyl chloride was substituted for 4-methylbenzenesulfonyl chloride. LC/MS: 502 (M+H). 1H-NMR (CDCl$_3$, ppm): 8.42 (s, broad, 1H), 7.60 (m, 2H), 7.52 (d, 2H), 7.39 (m, 2H), 7.30 (s, 1H), 7.10 (m, 4H), 4.42 (d, 2H), 4.20 (s, 2H).

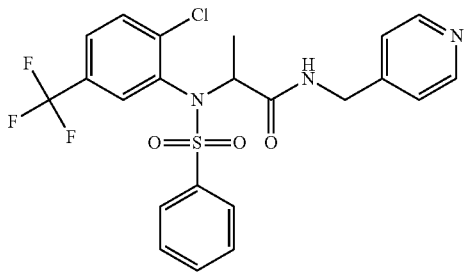 [SMILES: CC(C(=O)NCc1ccncc1)N(c1cc(C(F)(F)F)ccc1Cl)S(=O)(=O)c1ccccc1]

Example 4

Synthesis of 2-(N-(2-chloro-5-(trifluoromethyl)phenyl)phenylsulfonamido)-N-(pyridin-4-ylmethyl)propanamide The title compound was prepared according to the procedure for 2-[(2-Chloro-5-trifluoromethyl-phenyl)-(toluene-4-sulfonyl)-amino]-N-pyridin-4-ylmethyl-acetamide except 2-bromo-propionic acid ethyl ester was substituted for ethyl bromoacetate. LC/MS: 498 (M+H). $^1$H-NMR (CDCl$_3$, ppm): 8.56 (s, broad, 1H), 7.60 (m, 6H), 7.40 (m, 2H), 7.22 (m, 3H), 6.86 (s, 1H), 4.85 (q, 1H), 4.64 (m, 2H), 1.10 (d, 3H).

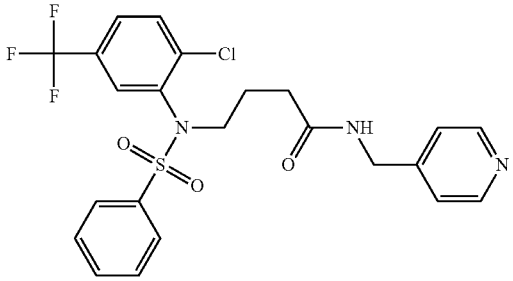 [SMILES: O=C(CCCN(c1cc(C(F)(F)F)ccc1Cl)S(=O)(=O)c1ccccc1)NCc1ccncc1]

Example 5

Synthesis of 4-(N-(2-chloro-5-(trifluoromethyl)phenyl)phenylsulfonamido)-N-(pyridin-4-ylmethyl)butanamide The title compound was prepared according to the procedure for 2-[(2-Chloro-5-trifluoromethyl-phenyl)-(toluene-4-sulfonyl)-amino]-N-pyridin-4-ylmethyl-acetamide except 4-bromo-butyric acid ethyl ester was substituted for ethyl bromoacetate. LC/MS: 512 (M+H). $^1$H-NMR (CDCl$_3$, ppm): 8.52 (s, broad, 1H), 7.52 (m, 8H), 7.24 (m, 2H), 7.15 (s, 1H), 6.52 (s, 1H), 4.45 (d, 2H), 3.64 (s, 1H), 3.42 (s, 1H), 2.50 (s, 2H), 1.80 (s, 2H).

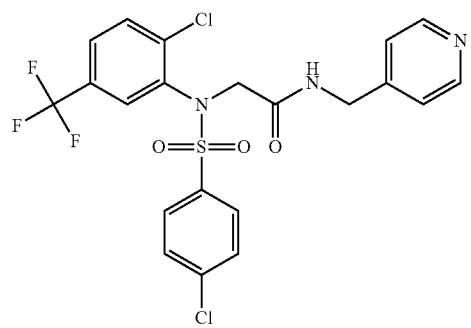

Example 6

Synthesis of 2-(4-chloro-N-(2-chloro-5-(trifluoromethyl)phenyl)phenylsulfonamido)-N-(pyridin-4-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except 4-Chlorobenzenesulfonyl chloride was substituted for 4-methylbenzenesulfonyl chloride. LC/MS: 518 (M+H). $^1$H-NMR (CDCl$_3$, ppm): 8.42 (s, broad, 1H), 7.60 (m, 6H), 7.34 (m, 3H), 7.15 (m, 2H), 4.45 (s, 2H), 4.20 (s, 2H).

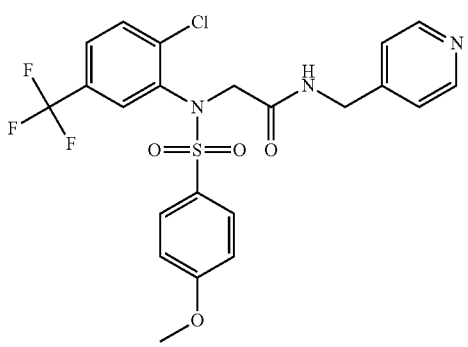 [SMILES: COc1ccc(S(=O)(=O)N(CC(=O)NCc2ccncc2)c2cc(C(F)(F)F)ccc2Cl)cc1]

Example 7

Synthesis of 2-(N-(2-chloro-5-(trifluoromethyl)phenyl)-4-methoxyphenylsulfonamido)-N-(pyridin-4-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except 4-methoxybenzenesulfonyl chloride was substituted for 4-methylbenzenesulfonyl chloride. LC/MS: 514 (M+H). $^1$H-NMR (CDCl$_3$, ppm): 8.42 (s, broad, 1H), 7.45 (m, 6H), 7.10 (m, 3H), 6.85 (d, 2H), 4.40 (d, 2H), 4.12 (s, 2H), 3.75 (s, 3H).

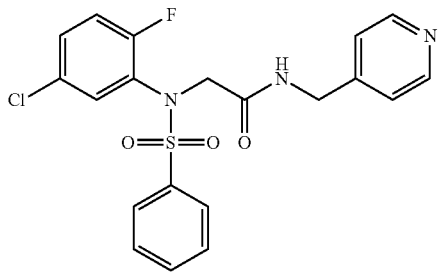 [SMILES: O=C(CN(c1cc(Cl)ccc1F)S(=O)(=O)c1ccccc1)NCc1ccncc1]

Example 8

Synthesis of 2-(N-(5-chloro-2-fluorophenyl)phenylsulfonamido)-N-(pyridin-4-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except 2-chloro-5-fluoroaniline was substituted for 2-chloro-5-trifluoromethylaniline. LC/MS: 434 (M+H). $^1$H-NMR (CDCl$_3$, ppm): 8.42 (s, broad, 1H), 7.58 (m, 2H), 7.45 (m, 2H), 7.22 (m, 2H), 7.15 (m, 2H), 7.04 (m, 2H), 6.85 (m, 2H), 4.40 (d, 2H), 4.12 (s, 2H).

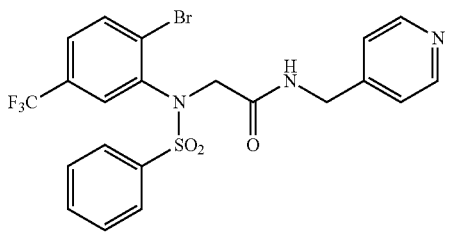 [SMILES: O=C(CN(c1cc(C(F)(F)F)ccc1Br)S(=O)(=O)c1ccccc1)NCc1ccncc1]

Example 9

Synthesis of 2-(N-(5-bromo-2-fluorophenyl)phenylsulfonamido)-N-(pyridin-4-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except 2-bromo-5-trifluoromethylaniline was substituted for 2-chloro-5-trifluoromethylaniline. LC/MS: 528.

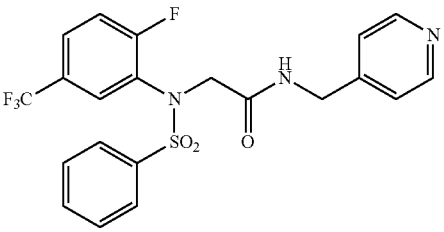 [SMILES: O=C(CN(c1cc(C(F)(F)F)ccc1F)S(=O)(=O)c1ccccc1)NCc1ccncc1]

Example 10

Synthesis of 2-(N-(5-bromo-2-fluorophenyl)phenylsulfonamido)-N-(pyridin-4-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except 2-fluoro-5-trifluoromethylaniline was substituted for 2-chloro-5-trifluoromethylaniline. LC/MS: 468.

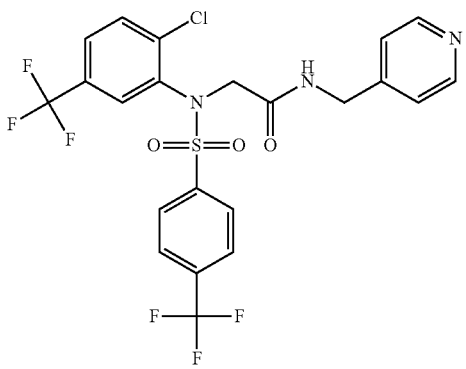 [SMILES: O=C(CN(c1cc(C(F)(F)F)ccc1Cl)S(=O)(=O)c1ccc(C(F)(F)F)cc1)NCc1ccncc1]

Example 11

Synthesis of 2-(N-(2-chloro-5-(trifluoromethyl)phenyl)-4-(trifluoromethyl)phenylsulfonamido)-N-(pyridin-4-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except 4-trifluoromethyl benzenesulfonyl chloride was substituted for 4-methylbenzenesulfonyl chloride. LC/MS: 552 (M+H). $^1$H-NMR (CDCl$_3$, ppm): 8.20 (s, broad, 1H), 7.42 (m, 5H), 7.24 (m, 2H), 7.02 (s, 1H), 6.95 (m, 1H), 6.80 (m, 2H), 4.15 (d, 2H), 3.95 (s, 2H).

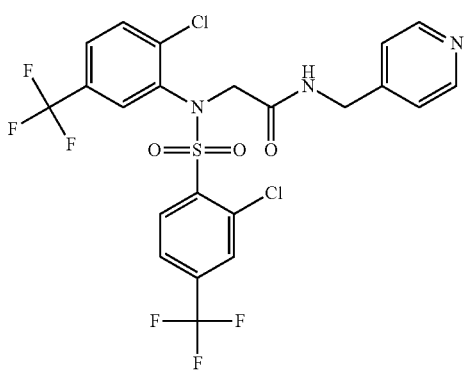 [SMILES: O=C(CN(c1cc(C(F)(F)F)ccc1Cl)S(=O)(=O)c1ccc(C(F)(F)F)cc1Cl)NCc1ccncc1]

Example 12

Synthesis of 2-(2-chloro-N-(2-chloro-5-(trifluoromethyl)phenyl)-4-(trifluoromethyl)phenylsulfonamido)-N-(pyridin-4-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except 2-chloro-4-trifluoromethyl benzenesulfonyl chloride was substituted for 4-methylbenzenesulfonyl chloride. LC/MS: 596 (M +H). 1H-NMR (300 MHz, CD3OD, ppm): 8.42 (d, 2H), 8.17 (s, 1H), 8.00 (d, 1H), 7.97 (s, 1H), 7.73 (d, 1H), 7.67 (d, 1H), 7.61 (d, 1H), 7.28 (d, 2H), 4.42 (s, 2H), 3.28 (s, 2H).

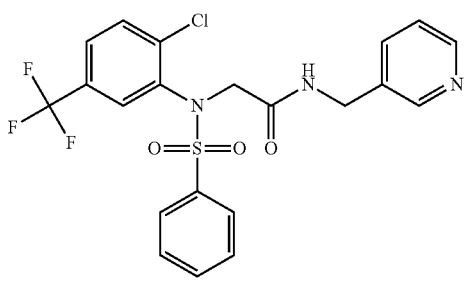 [SMILES: O=C(CN(c1cc(C(F)(F)F)ccc1Cl)S(=O)(=O)c1ccccc1)NCc1cccnc1]

Example 13

Synthesis of 2-(N-(2-chloro-5-(trifluoromethyl)phenyl)phenyl sulfonamido)-N-(pyridin-3-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except benzenesulfonyl chloride was substituted for 4-methylbenzenesulfonyl chloride and 3-aminomethylpyridine was substituted for 4-aminomethylpyridine. LC/MS: 484 (M+H). 1H-NMR (300 MHz, CD3OD, ppm): 8.43 (m, 2H), 7.86 (s, 1H), 7.54-7.71 (m, 6H), 7.51-7.54 (t, 2H), 7.36 (m, 1H), 4.40 (s, 2H), 3.30 (s, 2H).

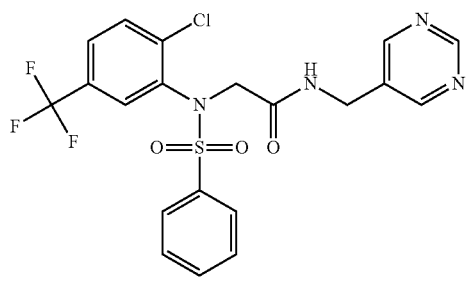 [SMILES: O=C(CN(c1cc(C(F)(F)F)ccc1Cl)S(=O)(=O)c1ccccc1)NCc1cncnc1]

Example 14

Synthesis of 2-(N-(2-chloro-5-(trifluoromethyl)phenyl)phenyl sulfonamido)-N-(pyrimidin-5-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except benzenesulfonyl chloride was substituted for 4-methylbenzenesulfonyl chloride and pyrimidin-5-yl-methylamine was substituted for 4-aminomethylpyridine.

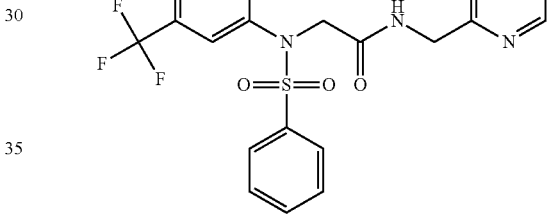

Example 15

Synthesis of 2-(N-(2-chloro-5-(trifluoromethyl)phenyl)phenyl sulfonamido)-N-(pyrimidin-4-ylmethyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except benzenesulfonyl chloride was substituted for 4-methylbenzenesulfonyl chloride and pyrimidin-4-yl-methylamine was substituted for 4-aminomethylpyridine. LC/MS: 485 (M+H). 1H-NMR (300 MHz, CD3OD, ppm): 9.04 (s, 1H), 8.68 (d, 1H), 7.91 (s, 1H), 7.74-7.65 (m, 5H), 7.55 (t, 2H), 7.41 (d, 1H), 4.48 (s, 2H), 3.31 (s, 2H).

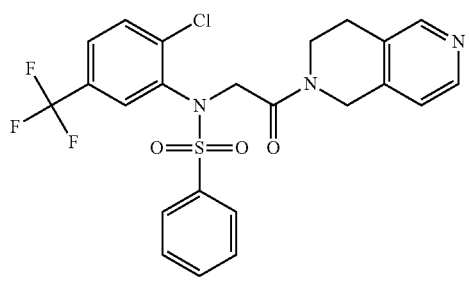 [SMILES: O=C(CN(c1cc(C(F)(F)F)ccc1Cl)S(=O)(=O)c1ccccc1)N1CCc2cnccc2C1]

Example 16

Synthesis of N-(2-chloro-5-(trifluoromethyl)phenyl)-N-(2-(3,4-dihydro-2,6-naphthyridin-2(1H)-yl)-2-oxoethyl)benzenesulfonamide The title compound was prepared according to the procedure for 2-[(2-Chloro-5-trifluoromethyl-phenyl)-(toluene-4-sulfonyl)-amino]-N-pyridin-4-ylmethyl-acetamide except benzenesulfonyl chloride was substituted for 4-methylbenzenesulfonyl chloride and 1,2,3,4-tetrahydro-[2,6]naphthyridine was substituted for 4-aminomethylpyridine. LC/MS: 510 (M+H). 1H-NMR (300 MHz, CD3OD, ppm): 8.39 (m, 2H), 7.95 (s, 1H), 7.73-7.50 (m, 7H), 7.25 (t, 1H), 4.83-4.67 (m, 4H), 3.84-3.77 (m, 2H), 2.98 (t, 1H), 2.83 (t, 1H)

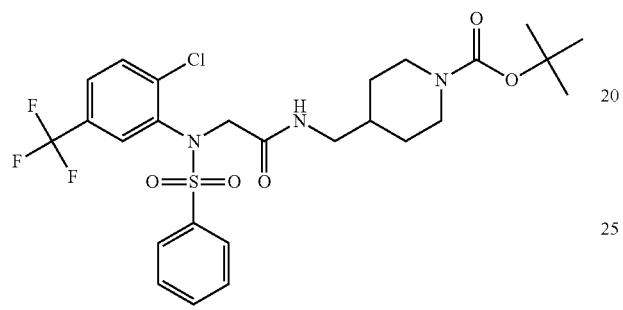

Example 17

Synthesis of tert-butyl 4-((2-(N-(2-chloro-5-(trifluoromethyl)phenyl)phenylsulfonamido)acetamido)methyl) piperidine-1-carboxylate The title compound was prepared according to the procedure for 2-[(2-Chloro-5-trifluoromethyl-phenyl)-(toluene-4-sulfonyl)-amino]-N-pyridin-4-ylmethyl-acetamide except benzenesulfonyl chloride was substituted for 4-methylbenzenesulfonyl chloride and 4-aminomethyl-piperidine-1-carboxylic acid tert-butyl ester was substituted for 4-aminomethylpyridine. LC/MS: 612 (M+Na). 1H-NMR (300 MHz, CDCl3, ppm): 7.72-7.66 (m, 3H), 7.60-7.25 (m, 3H), 7.17 (s, 1H), 7.05 (t, 1H), 4.11 (s, broad, 3H), 3.20 (s, 2H), 2.65 (t, 2H), 1.68 (t, 4H), 1.45 (s, 9H), 1.20-1.02 (m, 2H).

Example 18

Synthesis of tert-butyl (2-(2-(N-(2-chloro-5-(trifluoromethyl)phenyl)phenylsulfonamido)acetamido)ethyl)carbamate The title compound was prepared according to the procedure for 2-[(2-Chloro-5-trifluoromethyl-phenyl)-(toluene-4-sulfonyl)-amino]-N-pyridin-4-ylmethyl-acetamide except benzenesulfonyl chloride was substituted for 4-methylbenzenesulfonyl chloride and (2-amino-ethyl)-carbamic acid tert-butyl ester was substituted for 4-aminomethylpyridine. LC/MS: 558 (M+Na). 1H-NMR (300 MHz, CDCl3, ppm): 7.69 (m, 2H), 7.57 (m, 5H), 7.38 (s, 1H), 4.15 (s, 2H), 3.42 (t, 2H), 3.29 (t, 2H), 1.46 (s, 9H).

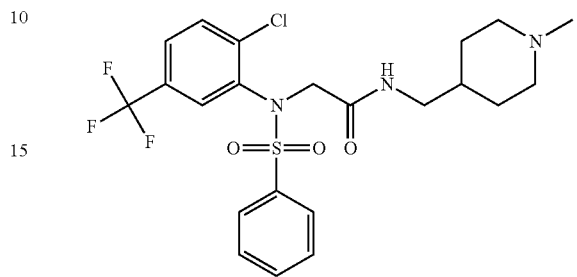

Example 19

Synthesis of 2-(N-(2-chloro-5-(trifluoromethyl)phenyl)phenylsulfonamido)-N-((1-methylpiperidin-4-yl)methyl)acetamide The title compound was prepared according to the procedure for 2-[(2-Chloro-5-trifluoromethyl-phenyl)-(toluene-4-sulfonyl)-amino]-N-pyridin-4-ylmethyl-acetamide except benzenesulfonyl chloride was substituted for 4-methylbenzenesulfonyl chloride and (1-methyl-piperidin-4-yl)-methylamine was substituted for 4-aminomethylpyridine. LC/MS: 504 (M+H). 1H-NMR (300 MHz, CD3OD, ppm): 7.82 (s, 1H), 7.72-7.64 (m, 5H), 7.58-7.52 (m, 2H), 4.35 (broad s, 2H), 3.06 (d, 2H), 2.95 (d, 2H), 2.34 (s, 3H), 2.14 (t, 2H), 1.65 (m, 2H), 1.28 (m, 3H).

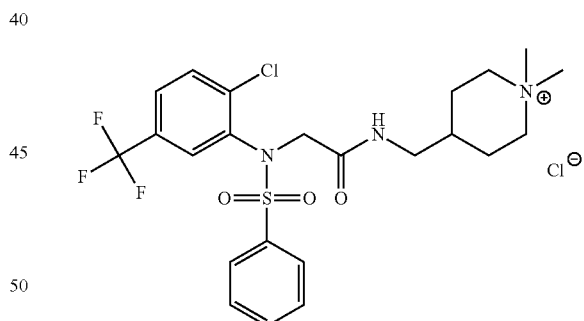

Example 20

Synthesis of 4-((2-(N-(2-chloro-5-(trifluoromethyl)phenyl)phenylsulfonamido)acetamido)methyl)-1,1-dimethylpiperidin-1-ium chloride The title compound was prepared according to the procedure for 2-[(2-Chloro-5-trifluoromethyl-phenyl)-(toluene-4-sulfonyl)-amino]-N-pyridin-4-ylmethyl-acetamide except benzenesulfonyl chloride was substituted for 4-methylbenzenesulfonyl chloride and (1,1-dimethyl-piperidin-4-yl)-methylamium chloride was substituted for 4-aminomethylpyridine. LC/MS: 518 (M+H). 1H-NMR (300 MHz,

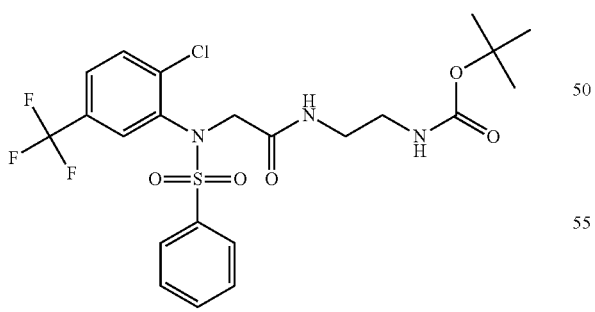

CD3OD, ppm): 7.89 (s, 1H), 7.72-7.64 (m, 5H), 7.58-7.52 (m, 2H), 4.38 (broad s, 2H), 3.50-2.94 (m, 10H), 2.00-1.75 (m, 5H), 1.45-1.32 (m, 2H).

Example 21

Synthesis of 2-[Benzenesulfonyl-(2-chloro-5-trifluoromethyl-phenyl)-amino]-N-(2-methyl-benzothiazol-5-yl)-acetamide

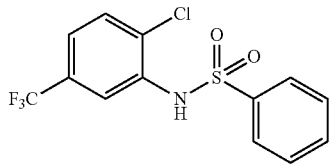 [SMILES: O=S(=O)(Nc1cc(C(F)(F)F)ccc1Cl)c1ccccc1]

Synthesis of N-(2-Chloro-5-trifluoromethyl-phenyl)-benzenesulfonamide

To a solution of 2-chloro-5-(trifluoromethyl)aniline (0.41 mL, 3 mmol) in pyridine (5 mL), was added dropwise benzenesulfonyl chloride (0.44 mL 3.1 mmol) at 0° C. After addition, the reaction was stirred at the same temperature for 2 hours. Then, it was quenched with 2 N HCl (20 mL) at 0° C., and extracted with ethyl acetate (2×20 mL). The combined organic layer was washed with brine (20 mL), dried over anhydrous sodium sulfate, filtered, and concentrated. The resulting crude product was re-crystallized in a mixture of ethyl acetate and hexanes to afford N-(2-Chloro-5-trifluoromethyl-phenyl)-benzenesulfonamide. $^1$H NMR (300 MHz, CDCl$_3$): δ 7.93 (s, 1H), 7.82-7.79 (m, 2H), 7.61-7.55 (m, 1H), 7.50-7.44 (m, 2H), 7.38 (d, J=8.4 Hz, 1H), 7.28 (d, J=8.4 Hz, 1H), 7.13 (s, 1H). MS: MNa$^+$=358.

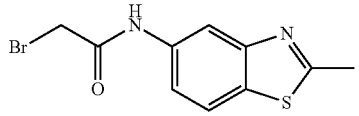

Synthesis of 2-bromo-N-(2-methylbenzo[d]thiazol-5-yl)acetamide

To a solution of 2-methylbenzo[d]thiazol-5-amine (493 mg, 3 mmol) and triethylamine (0.42 mL, 3 mmol) in dichloromethane (10 mL), was added dropwise a solution of bromoacetyl bromide (0.26 mL, 3 mmol) in dichloromethane (5 mL) at 0° C. After addition, the reaction was stirred at this temperature for 1 hour. Then, it was washed with water (20 mL×4), dried over anhydrous sodium sulfate and filtered. The solvent was removed under vacuum and the resulting residue was washed with hexanes to provide 2-bromo-N-(2-methylbenzo[d]thiazol-5-yl)acetamide which was used without further purification.

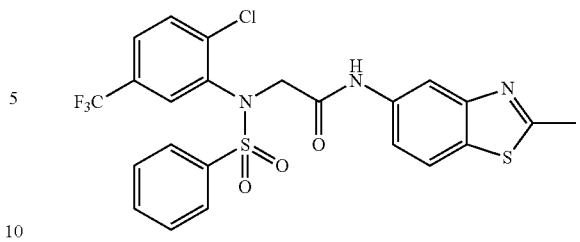

Synthesis of 2-[Benzenesulfonyl-(2-chloro-5-trifluoromethyl-phenyl)-amino]-N-(2-methyl-benzothiazol-5-yl)-acetamide A mixture of N-(2-Chloro-5-trifluoromethyl-phenyl)-benzenesulfonamide (101 mg, 0.3 mmol), 2-bromo-N-(2-methylbenzo[d]thiazol-5-yl)acetamide (94 mg, 0.33 mmol) and potassium carbonate (46 mg, 0.33 mmol) in acetonitrile (15 mL) was stirred at 60° C. for 24 hours. After cooling to room temperature, the reaction was quenched with water (20 mL) and extracted with ethyl acetate (3×20 mL). The combined organic layer was dried over anhydrous sodium sulfate, filtered, concentrated under vacuum, and purified with silica gel chromatography (ethyl acetate:hexanes=10:90 to 50:50) to afford 2-[Benzenesulfonyl-(2-chloro-5-trifluoromethyl-phenyl)-amino]-N-(2-methyl-benzothiazol-5-yl)-acetamide. $^1$H NMR (300 MHz, CDCl$_3$): δ 8.92 (s, 1H), 8.16 (d, J=2.1 Hz, 1H), 7.77-7.55 (m, 9H), 7.16 (d, J=0.6 Hz, 1H), 4.40 (br, s, 2H), 2.83 (s, 3H). MS: MH$^+$=540.

The following compounds can be prepared by the procedure of 2-[Benzenesulfonyl-(2-chloro-5-trifluoromethyl-phenyl)-amino]-N-(2-methyl-benzothiazol-5-yl)-acetamide. The skilled practitioner will know how to substitute the appropriate reagents, starting materials and purification methods known to those skilled in the art, in order to prepare the compounds provided herein.

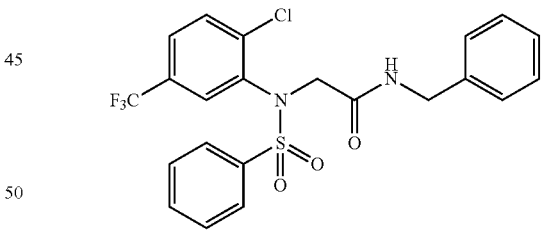

Example 22

Synthesis of 2-[Benzenesulfonyl-(2-chloro-5-trifluoromethyl-phenyl)-amino]-N-benzyl-acetamide The title compound was prepared according to the procedure for 2-[Benzenesulfonyl-(2-chloro-5-trifluoromethyl-phenyl)-amino]-N-(2-methyl-benzothiazol-5-yl)-acetamide except benzyl amine was substituted for 2-methylbenzo[d]thiazol-5-amine. $^1$H NMR (300 MHz, CDCl$_3$): δ 7.69-7.67 (m, 3H), 7.57-7.52 (m, 4H), 7.35-7.20 (m, 7H), 4.49 (d, J=5.7 Hz, 2H), 4.23 (s, 2H). MS: MNa$^+$=505.

Example 23

Synthesis of 2-[Benzenesulfonyl-(2-chloro-5-trifluoromethyl-phenyl)-amino]-N-[4-(4-methyl-piperazin-1-yl)-benzyl]-acetamide

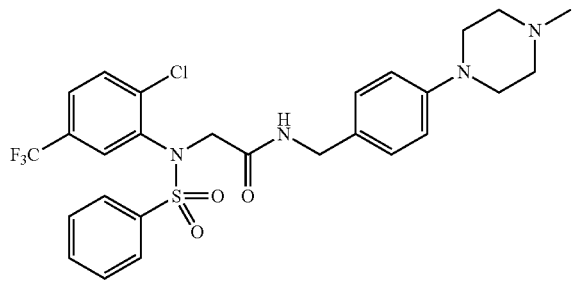 [SMILES: CN1CCN(c2ccc(CNC(=O)CN(c3cc(C(F)(F)F)ccc3Cl)S(=O)(=O)c3ccccc3)cc2)CC1]

To a stirred mixture of 2-(N-(2-chloro-5-(trifluoromethyl)phenyl)phenylsulfonamido)acetic acid (40.3 mg, 0.10 mmol), 1-ethyl-3-(3-dimethylaminopropyl)carbodiimide HCl (24.2 mg, 0.13 mmol), and hydroxybenzotriazole (17.6 mg, 0.13 mmol) in methylene chloride (1 mL) was added a solution of (4-(4-methylpiperazin-1-yl)phenyl)methanamine (20 mg, 0.10 mmol) in N,N-dimethylformamide: methylene chloride (0.1 mL:1 mL). The resulting solution was stirred at room temperature for a week. The mixture was concentrated, purified on silica gel eluted with a gradient of methanol: methylene chloride from 0:1 to 1:9 to provide the title product (39.2 mg). $^1$H NMR (300 MHz, CDCl$_3$): δ 7.64-7.56 (m, 3H), 7.50-7.41 (m, 4H), 7.15-7.12 (m, 1H), 7.11-7.04 (m, 2H), 6.97 (t, J=5.3 Hz, 1H), 6.85-6.78 (m, 2H), 4.30 (d, J=5.3 Hz, 2H), 4.13 (broad s, 2H), 3.18-3.10 (m, 4H), 2.56-2.46 (m, 4H), 2.29 (s, 3H); Calculated for C$_{27}$H28ClF3N4O3S, 580.15; observed MS (ESI) (m/z) 581.2 (M+1)$^+$.

Example 24

Synthesis of 2-[Benzenesulfonyl-(2-chloro-5-trifluoromethyl-phenyl)-amino]-N-[3-(4-methyl-piperazin-1-yl)-benzyl]-acetamide

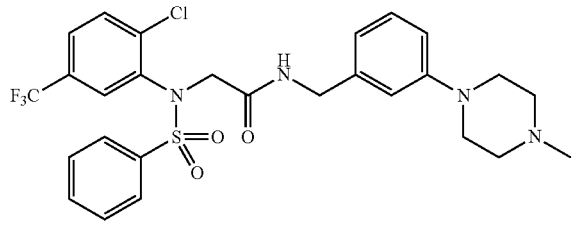 [SMILES: CN1CCN(c2cccc(CNC(=O)CN(c3cc(C(F)(F)F)ccc3Cl)S(=O)(=O)c3ccccc3)c2)CC1]

To a stirred mixture of 2-(N-(2-chloro-5-(trifluoromethyl)phenyl)phenylsulfonamido)acetic acid (40.3 mg, 0.10 mmol), 1-ethyl-3-(3-dimethylaminopropyl) carbodiimide HCl (24.2 mg, 0.13 mmol), and hydroxybenzotriazole (17.6 mg, 0.13 mmol) in methylene chloride (1 mL) was added a solution of (3-(4-methylpiperazin-1-yl)phenyl)methanamine (20 mg, 0.10 mmol) in N,N-dimethylformamide: methylene chloride (0.1 mL: 1 mL). The resulting solution was stirred at room temperature for a week. The mixture was concentrated, purified on silica gel eluted with a gradient of methanol: methylene chloride from 0:1 to 1:9 to provide the title compound (41.5 mg, 74%). $^1$H NMR (300 MHz, CDCl$_3$): δ 7.64-7.56 (m, 3H), 7.50-7.42 (m, 4H), 7.18-7.02 (m, 3H), 6.81-6.74 (m, 2H), 6.65 (d, J=7.4 Hz, 1H), 4.35 (d, J=8.9 Hz, 2H), 4.13 (broad s, 2H), 3.18-3.10 (m, 4H), 2.54-2.45 (m, 4H), 2.28 (s, 3H); Calculated for C27H28ClF3N4O3S, 580.15; observed MS (ESI) (m/z) 581.2 (M+1)$^+$.

Example 25

Synthesis of 4-(Benzyl-methyl-sulfamoyl)-N-(2-methyl-benzothiazol-5-yl)-benzamide

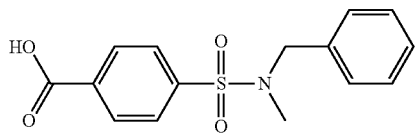 [SMILES: CN(Cc1ccccc1)S(=O)(=O)c1ccc(C(=O)O)cc1]

Synthesis of 4-(N-benzyl-N-methylsulfamoyl)benzoic acid

To a stirred solution of 4-(chlorosulfonyl)benzoic acid (6.00 g, 27.2 mmol) in methanol (60 mL) at 0° C., was added N-benzylmethylamine (3.86 mL, 29.9 mmol), followed by the addition of triethylamine (5.31 mL, 38.1 mmol). The reaction mixture was stirred at room temperature for 24 hours. Then, it was quenched with 1 N HCl (200 mL), filtered and washed with water (200 mL). The crude product was purified by re-crystallization from ethanol to provide 7.45 g of the title compound as white solid. $^1$H NMR (300 MHz, DMSO-d$_6$): δ 13.50 (s, 1H), 8.16 (d, J=8.7 Hz, 2H), 7.95 (d, J=8.4 Hz, 2H), 7.35-7.27 (m, 5H), 4.15 (s, 2H), 2.55 (s, 3H).

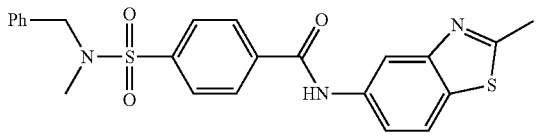 [SMILES: Cc1nc2cc(NC(=O)c3ccc(S(=O)(=O)N(C)Cc4ccccc4)cc3)ccc2s1]

Synthesis of 4-(Benzyl-methyl-sulfamoyl)-N-(2-methyl-benzothiazol-5-yl)-benzamide To a suspension of 4-(N-benzyl-N-methylsulfamoyl)benzoic acid (140 mg, 0.46 mmol) in dichloromethane (5 mL), was added oxalyl chloride (47 μL, 0.55 mmol) at room temperature, followed by 2 drops of DMF. After stirred for 1 hour, the solvent and excessive oxalyl chloride were removed by evaporation to give the crude acid chloride as white solid, which was used in the next step directly.

The acid chloride obtained above was re-dissolved in dichloromethane (5 mL), and then added to a solution of 2-methylbenzo[d]thiazol-5-amine (68 mg, 0.42 mmol) and triethylamine (128 μL, 0.92 mmol) in dichloromethane (5 mL). After addition, the reaction was allowed to warmed up to room temperature and stirred for 1 hour. Then, it was washed with 1 N HCl (20 mL), and the aqueous layer was extracted with ethyl acetate (20 mL×2). The combined organic layer was washed with brine (20 mL) and dried over anhydrous sodium sulfate. After concentrated, the crude product was purified through silica gel column (ethyl acetate:hexanes=40:60) to afford 140 mg of compound 4-(Benzyl-methyl-sulfamoyl)-N-(2-methyl-benzothiazol-5-yl)-benzamide as a white solid. Yield, 67%. $^1$H NMR (300 MHz, CDCl$_3$): δ 8.23 (d, J=1.8 Hz, 1H), 8.16 (s, 1H), 8.0b6 (d, J=8.4 Hz, 2H), 7.93-7.91 (m, 2H), 7.82 (d, J=8.7 Hz, 1H), 7.74 (dd, J=9.0, 2.1 Hz, 1H), 7.36-7.28 (m, 5H), 4.17 (s, 2H), 2.85 (s, 3H), 2.63 (s, 1H). MS: MH$^+$=452.

Example 26

Synthesis of 4-(Benzyl-methyl-sulfamoyl)-N-(2-methyl-1H-indol-5-yl)-benzamide

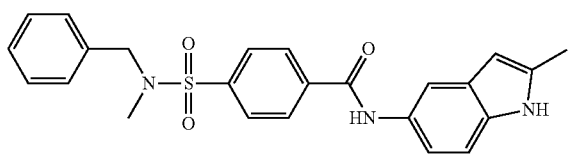 [SMILES: Cc1cc2cc(NC(=O)c3ccc(S(=O)(=O)N(C)Cc4ccccc4)cc3)ccc2[nH]1]

4-(Benzyl-methyl-sulfamoyl)-N-(2-methyl-1H-indol-5-yl)-benzamide was prepared by the same procedures of 4-(Benzyl-methyl-sulfamoyl)-N-(2-methyl-benzothiazol-5-yl)-benzamide in example 25. $^1$H NMR (300 MHz, CDCl$_3$): δ 8.79 (s, 1H), 8.05 (d, J=6.6 Hz, 2H), 7.88 (d, J=7.5 Hz, 2H), 7.79 (s, 1H), 7.30-7.27 (m, 6H), 6.19 (s, 1H), 4.16 (s, 2H), 2.62 (s, 3H), 2.43 (s, 3H). MS: MNa$^+$=456.

The following compounds can be prepared by the procedure of 4-(Benzyl-methyl-sulfamoyl)-N-(2-methyl-benzothiazol-5-yl)-benzamide. The skilled practitioner will know how to substitute the appropriate reagents, starting materials and purification methods known to those skilled in the art, in order to prepare the compounds provided herein.

Example 27

Synthesis of N-Benzothiazol-6-yl-4-(benzyl-methyl-sulfamoyl)-benzamide

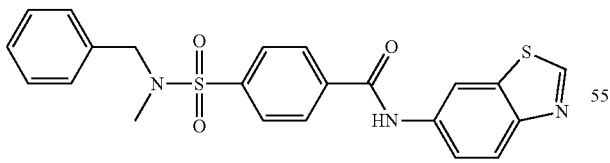

N-Benzothiazol-6-yl-4-(benzyl-methyl-sulfamoyl)-benzamide was prepared by the same procedures of 4-(Benzyl-methyl-sulfamoyl)-N-(2-methyl-benzothiazol-5-yl)-benzamide in example 1. $^1$H NMR (300 MHz, CDCl$_3$): δ 8.96 (s, 1H), 8.80 (s, 1H), 8.72 (d, J=1.8 Hz, 1H), 8.08 (d, J=8.7 Hz, 1H), 8.01 (d, J=8.4 Hz, 2H), 7.78 (d, J=8.7 Hz, 2H), 7.61 (dd, J=9.0, 2.1 Hz, 1H), 7.35-7.27 (m, 5H), 4.15 (s, 2H), 2.62 (s, 3H). MS: MH$^+$=438.

Example 28

Synthesis of 4-(Benzyl-methyl-sulfamoyl)-N-(2-methyl-benzothiazol-6-yl)-benzamide

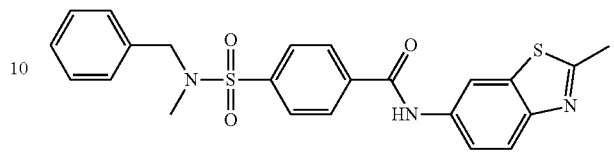

4-(Benzyl-methyl-sulfamoyl)-N-(2-methyl-benzothiazol-6-yl)-benzamide was prepared by the same procedures of 4-(Benzyl-methyl-sulfamoyl)-N-(2-methyl-benzothiazol-5-yl)-benzamide in example 1. $^1$H NMR (300 MHz, CDCl$_3$): δ 8.55 (d, J=1.8 Hz, 1H), 8.26 (s, 1H), 8.04 (d, J=8.4 Hz, 2H), 7.93-7.88 (m, 3H), 7.46 (dd, J=8.7, 2.4 Hz, 1H), 7.35-7.31 (m, 5H), 4.18 (s, 2H), 2.84 (s, 3H), 2.64 (s, 3H). MS: MH$^+$=452.

Example 29

Synthesis of 4-(Benzyl-methyl-sulfamoyl)-N-pyridin-4-ylmethyl-benzamide

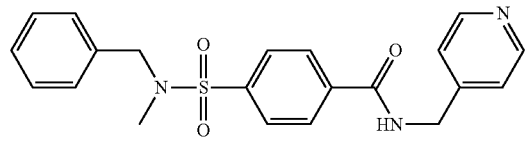 [SMILES: CN(Cc1ccccc1)S(=O)(=O)c1ccc(C(=O)NCc2ccncc2)cc1]

$^1$H NMR (300 MHz, CDCl$_3$): δ 8.49 (d, J=5.1 Hz, 2H, CH$_{ar}$), 7.99 (d, J=8.4 Hz, 2H), 7.80 (d, J=8.4 Hz, 2H), 7.62 (t, J=5.4 Hz, 1H), 7.36-7.25 (m, 7H), 4.66 (d, J=5.7 Hz, 2H), 4.12 (s, 2H), 2.59 (s, 3H). MS: MH$^+$=396.

Example 30

Synthesis of 1-Benzenesulfonyl-pyrrolidine-2-carboxylic acid (pyridin-4-ylmethyl)-amide

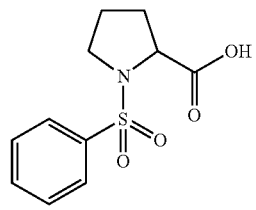 [SMILES: O=C(O)C1CCCN1S(=O)(=O)c1ccccc1]

To a solution of D,L-proline (2.00 g, 17.4 mmol) in 1 N NaOH (34.8 mL, 34.8 mmol), at 0° C., was added benzenesulfonyl chloride (2.65 mL, 20.8 mmol) slowly. After addition, the reaction was stirred at room temperature for 24 hours. Then, the pH of the mixture was adjusted to 11~12 and washed with ethyl acetate (2×30 mL). The aqueous layer was acidified to pH 1~2 and extracted with ethyl acetate (30 mL×3). The combined organic layer was dried over anhydrous sodium sulfate and concentrated to afford 4.14 g of 1-(phenylsulfonyl)pyrrolidine-2-carboxylic acid as white solid. $^1$H NMR (300 MHz, CDCl$_3$): δ 7.91-7.88 (m, 2H, CH$_{ar}$), 7.67-7.53 (m, 3H, CH$_{ar}$), 4.33-4.29 (m, 1H, CH), 3.58-3.51 (m, 1H, CH), 3.33-3.25 (m, 1H, CH), 2.17-1.74 (m, 4H, 2×CH$_2$). MS: MH$^+$=256.

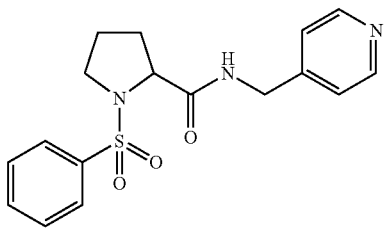 [SMILES: O=C(NCc1ccncc1)C1CCCN1S(=O)(=O)c1ccccc1]

To a suspension of 1-(phenylsulfonyl)pyrrolidine-2-carboxylic acid (128 mg, 0.5 mmol) in dichloromethane (5 mL), was added oxalyl chloride (51 μL, 0.6 mmol) at room temperature, followed by 3 drops of N,N-dimethylformamide. After stirring for 1 hour, the solvent and excessive oxalyl chloride were removed by evaporation to give the crude acid chloride as white solid, which was used in the next step directly.

The acid chloride obtained was re-dissolved in dichloromethane (5 mL), and then added to a solution of pyridin-4-ylmethanamine (46 μL, 0.45 mmol) and triethylamine (139 μL, 1 mmol) in dichloromethane (5 mL) at 0° C. After addition, the reaction was allowed to warmed up to room temperature and stirred for another hour. Then, it was washed with water (20 mL×2), brine (20 mL), dried over anhydrous sodium sulfate, and filtered. The solvent were removed under vacuum and the crude product was purified by silica gel chromatography (methanol:ethyl acetate=2:98 to 4:96) to afford 145 mg of the title compound. $^1$H NMR (300 MHz, CDCl$_3$): δ 8.58 (d, J=5.7 Hz, 2H), 7.88-7.85 (m, 2H), 7.71-7.66 (m, 1H), 7.61-7.56 (m, 2H), 7.46 (s, 1H), 7.27-7.25 (m, 2H), 4.65-4.43 (m, 2H), 4.19-4.15 (m, 1H), 3.64-3.58 (m, 1H), 3.24-3.16 (m, 1H), 2.24-2.19 (m, 1H), 1.78-1.60 (m, 3H). MS: MH$^+$=346.

Example 31

Synthesis of 1-(phenylsulfonyl)-N-(pyridin-4-ylmethyl)-1H-indole-2-carboxamide

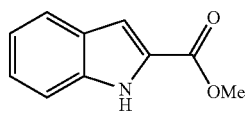 [SMILES: COC(=O)c1cc2ccccc2[nH]1]

Synthesis of methyl 1H-indole-2-carboxylate

A reaction mixture of 1H-indole-2-carboxylic acid (1.61 g, 10 mmol) and conc. sulfuric acid (0.5 mL) in methanol (50 mL) was refluxed for 24 hours. Then, the solvent was removed by evaporation, followed by addition of water (50 mL). The pH was adjusted to 7~8 by sodium bicarbonate powder and the mixture was extracted with ethyl acetate (30 mL×3). The combined extraction was dried over anhydrous sodium sulfate, filtered, and concentrated to give 1.58 g of the title compound as light-brown solid. The material was used without further purification. MS: MNa$^+$=338.

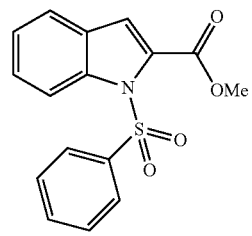 [SMILES: COC(=O)c1cc2ccccc2n1S(=O)(=O)c1ccccc1]

Synthesis of methyl 1-(phenylsulfonyl)-1H-indole-2-carboxylate

To a solution of methyl 1H-indole-2-carboxylate (350 mg, 2 mmol) in N,N-dimethylformamide (10 mL), was added sodium hydride (60%, 120 mg, 3.0 mmol), followed by addition of benzenesulfonyl chloride (0.26 mL, 2 mmol) at room temperature. After stirring for 1 hour, the reaction mixture was diluted with ethyl acetate (30 mL) and washed with brine (20 mL×3). The organic layer was dried over anhydrous sodium sulfate, filtered, concentrated, and purified by silica gel chromatography (ethyl acetate:hexanes=5:95 to 20:80) to afford 605 mg of the title compound as white solid.

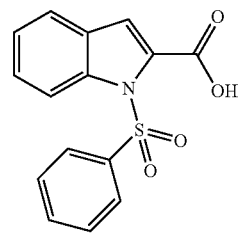 [SMILES: O=C(O)c1cc2ccccc2n1S(=O)(=O)c1ccccc1]

Synthesis of 1-(phenylsulfonyl)-1H-indole-2-carboxylic acid

To a solution of methyl 1-(phenylsulfonyl)-1H-indole-2-carboxylate (473 mg, 1.5 mmol) in tetrahydrofuran/methanol/water (5:5:1, 11 mL) was added lithium hydroxide monohydrate (441 mg, 10.5 mmol). The reaction mixture was heated to reflux for 5 hours. After cooling to room temperature, it was concentrated, followed by addition of water (10 mL). The pH was adjusted to 2 with 1N HCl and extracted with ethyl acetate (15 mL×3). The combined extraction was dried over anhydrous sodium sulfate, filtered, and concentrated. The crude product was purified by recrystallization in a mixture of dichloromethane and hexanes to afford 295 mg of the title compound as white solid.

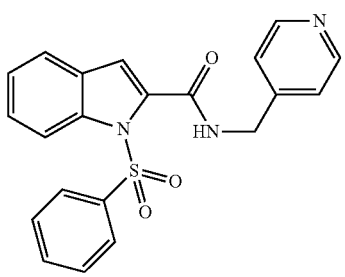 [SMILES: O=C(NCc1ccncc1)c1cc2ccccc2n1S(=O)(=O)c1ccccc1]

Synthesis of 1-(phenylsulfonyl)-N-(pyridin-4-ylmethyl)-1H-indole-2-carboxamide To a suspension of 1-(phenylsulfonyl)-1H-indole-2-carboxylic acid (151 mg, 0.5 mmol) in dichloromethane (5 mL), was added oxalyl chloride (51 µL, 0.6 mmol) at room temperature, followed by 3 drops of N,N-dimethylformamide. After stirred for 1 hr, the solvent and excessive oxalyl chloride were removed by evaporation to give the crude acid chloride as white solid, which was used in the next step directly.

The acid chloride was re-dissolved in dichloromethane (5 mL), and then added to a solution of pyridin-4-ylmethanamine (46 µL, 0.45 mmol) and triethylamine (139 µL, 1 mmol) in dichloromethane (5 mL) at 0° C. After addition, the reaction was allowed to warmed up to room temperature and stirred for another hour. Then, it was washed with water (20 mL), brine (20 mL), dried over anhydrous sodium sulfate, and filtered. The solvents were removed under vacuum and the crude product was purified by preparative TLC (ethyl acetate:hexanes=70:30) to afford 86 mg of the title compound. $^1$H NMR (300 MHz, CDCl$_3$): δ 8.53 (s, 2H), 8.07-8.00 (m, 3H), 7.52-7.16 (m, 9H), 6.96 (s, 1H), 4.65 (d, J=5.4 Hz, 2H). MS: MH$^+$=392.

Formulations

The present invention also relates to compositions or formulations which comprise the covalently closed circular DNA inhibitors according to the present invention. In general, the compositions of the present invention comprise an effective amount of one or more functionalized sulfonamides and salts thereof according to the present invention which are effective for providing treating or preventing diseases that involve the formation of covalently closed circular DNA, for example, hepatitis B infection; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known antiviral agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more functionalized sulfonamides according to the present invention and one or more excipients; from about 0.01 mg to about 100 mg of one or more functionalized sulfonamides according to the present invention and one or more excipients; and from about 0.1 mg to about 10 mg of one or more functionalized sulfonamides according to the present invention; and one or more excipients.

Procedures

The following procedures can be utilized in evaluating and selecting compounds as covalently closed circular DNA formation inhibitors.

Cell cultures: HepG2.2.15 cells were maintained in DMEM/F12 medium (Mediatech, Manassas, Va.) supplemented with 10% fetal bovine serum, 100 U/ml penicillin and 100 μg/ml streptomycin, plus 400 μg/ml G418. Tetracycline inducible HBV producer cells, specifically HepDE19 and HepDES19 cells, were maintained in the same way as HepG2.2.15, but with the addition of 1 μg/ml tetracycline (Guo, H., D. Jiang, T. Zhou, A. Cuconati, T. M. Block, and J. T. Guo. 2007). To initiate HBV replication and cccDNA formation in HepDE19 and HepDES19 cells, tetracycline was withdrawn from the culture medium and the cells were cultured for the indicated time period.

High throughput compound screen and assay: HepDE19 cells were cultured under tetracycline containing medium until confluent, the cells were then trypsinized and seeded in 96-well plates at a density of $5.0 \times 10^4$ cells/well with tetracycline-free medium to induce HBV replication. Immediately following cell seeding, compounds were added to screening plates by means of automated liquid handling (Beckman Coulter, Brea, Calif.), at a final concentration of 10 μM in 1.0% DMSO. Each screening plate consisted of 80 compound test wells, 4 wells of cells with 1.0% DMSO only, 4 wells with DMSO and without cells, and 4 wells of cells with DMSO and 50 μM lamivudine (3TC) as a reference inhibitor. Screening plates were incubated at 37° C. in 5.0% $CO_2$ atmosphere for seven days. Intracellular HBeAg (precore) accumulation was assayed by indirect ELISA assay as follows. Media was removed from wells and the cell monolayer was fixed with 100% ice cold methanol for 20 min, followed with two washes (150 μl each) with PBS containing 0.5% Tween-20 (PBST) with 1 min incubation at room temperature. Wells were blocked for 12 hours at 4° C. with 100 μl PBST containing 2% bovine serum albumin (PBST/BSA), followed by incubation with 25 μl of PBST/BSA containing mouse monoclonal anti-HBeAg Ab (clone M2110146, Fitzgerald International, Acton Mass.) diluted 1:3200, 1 hour at 37° C. Wells were washed three times with PBST as above, excepting that plates were shaken at 600 rpm for 4 minutes between washes. This was followed with addition of 25 μl PBST/BSA containing horseradish peroxidase-conjugated anti-mouse Ab (diluted 1:5000), with incubation at 37° C. for 1 hour. This step was followed by three washes with shaking, and addition of 50 ul BM Blue POD substrate (Roche Applied Science, Indianapolis, Ind.). Signal was allowed to develop for 20 minutes and optical absorbance was determined at a wavelength of 650 nm with a reference reading at 490 nm. Wells where signal was reduced by 50% were defined as containing a hit compound.

To confirm activity of hit compounds, effective concentration inhibiting 50% of secretion activity ($EC_{50}$) was determined by incubating cells with compounds in duplicate wells, at concentrations from 50 μM to 0.016 μM (in half log steps), carrying out ELISA as described above, and best fit curve analysis of results with XLfit 4.0 (IDBS; Bridgewater, N.J.). Degree of inhibition was calculated against multiple negative control samples where only DMSO was incubated with cells. In addition, each plate had multiple wells containing 50 μM 3TC as a reference inhibitor. Only curves with $R^2$ values of above 0.5 were considered to produce valid $EC_{50}$ values.

Concentration exhibiting 50% cytotoxicity ($CC_{50}$) was determined by plating cells at $1.0 \times 10^4$ cells/well (20% confluence), to detect inhibition of cell growth as compared with absence of compounds. Cell plates were then incubated with compound dilutions and controls as described above, and addition of 3-[4,5-dimethylthiazol-2-yl]-2,5-diphenyltetrazolium bromide (MTT, Sigma-Aldrich) was added to a final concentration of 0.5 mg/ml (Mosmann, T. 1983). Plates were again incubated at 37° C. for 4 hrs, after which 10% SDS/0.01N HCl was added to each well in a volume equal to the medium (100 μl), followed by overnight incubation. Absorbance was read in the Rainbow spectrophotometer (Tecan US Inc., Durham, N.C.) at 570 nm (reference wavelength of 630 nm), and analyzed with XLfit 4.0 as described above.

Selective index (SI) for each compound was determined as SI=$CC_{50}$/$EC_{50}$. Compound hits with SI>4 were counter-screened through HepG2.2.15 cells, in which the majority of HBeAg expression is cccDNA-independent. Those compounds that did not significantly reduce HBeAg level in HepG2.2.15 cells were forwarded to the secondary assay.

Viral nucleic acid analysis: Total cellular RNA was extracted with TRIzol reagent (Invitrogen, Grand Island, N.Y.) by following manufacturer's directions. Ten microgram of total cellular RNA was resolved in 1.5% agarose gel containing 2.2 M formaldehyde and transferred onto Hybond-XL membrane (GE Healthcare, Piscataway, N.J.) in 20×SSC buffer. Intracellular hepadnaviral core DNA and cccDNA (Hirt DNA) were extracted as described previously (Guo, H., D. Jiang, T. Zhou, A. Cuconati, T. M. Block, and J. T. Guo. 2007. Guo, H., D. Jiang, T. Zhou, A. Cuconati, T. M. Block, and J. T. Guo. 2007. Guo, H., R. Mao, T. M. Block, and J. T. Guo. 2010. Guo, H., W. S. Mason, C. E. Aldrich, J. R. Saputelli, D. S. Miller, A. R. Jilbert, and J. E. Newbold. 2005). Half of the DNA samples recovered from one well of a 6-well-plate were resolved by electrophoresis into a 1.2% agarose gel and blotted onto Hybond-XL membrane. Membranes were probed with either an $\alpha$-$^{32}$P-UTP (800 Ci/mmol, Perkin Elmer) labeled hepadnaviral minus (detecting DNA) or plus strand (detecting RNA) specific full-length riboprobe and exposed to a phosphorimager screen (Fuji Film, Tokyo, Japan). Hybridization signals were visualized by Typhoon FLA-7000 (GE Healthcare) and quantified with ImageQuantTL software (GE Healthcare).

Endogenous DNA polymerase reaction (EPR): The EPR was performed as previously described with modifications (Guo, H., R. Mao, T. M. Block, and J. T. Guo. 2010). Briefly, EPR mixture was assembled with 10 µl of HBV virion stock (~5×$10^7$ genome equivalents) concentrated from the supernatant of HepDE19 cells cultured in tetracycline-free medium (Guo, H., D. Jiang, T. Zhou, A. Cuconati, T. M. Block, and J. T. Guo. 2007, plus 15 µl of 2×EPR buffer which consisted of 0.3 M NaCl, 0.1 M Tris-HCl (pH 8.0), 20 mM $MgCl_2$, 2 mM dithiothreitol, 0.2% (vol/vol) Nonidet P-40, 0.2 mM each of dATP/dGTP/dTTP, and 10 µM $\alpha$-$^{32}$P-dCTP. Compounds were added as indicated and water was supplemented to bring the reaction volume to 30 µl. As a positive control, 0.2 mM of dGTP in the 2×EPR buffer was replaced with 0.2 mM ddGTP. After incubation at 37° C. for 1 hours, the reaction solution was dotted on Whatman 3M filter (Millipore, Billerica, Mass.) and subjected to rinse with 10% trichloride acid for 30 min at room temperature, followed by 3 times of wash with 95% ethanol, 5 min each. The radioactivity (counts of per minute, CPM) of acid insoluble $^{32}$P was counted with a liquid scintillation counter (PerkinElmer, Waltham, Mass.).

Identification of novel cccDNA inhibitors by HTS: Compounds are screened initially at 10 µM followed by $EC_{50}$ determination by Using the HepDE19 cell system, in which the HBeAg is expressed in a cccDNA-dependent manner and serves as surrogate readout for cccDNA (Guo, H., D. Jiang, T. Zhou, A. Cuconati, T. M. Block, and J. T. Guo. 2007). Compounds were added simultaneously with tetracycline withdrawal, in order to identify inhibitors of cccDNA establishment and/or maintenance. HBeAg was detected using an in-house developed indirect ELISA or commercial ELISA assay. Nontoxic compounds causing a 50% reduction of HBeAg level were declared as primary hits. Hits were counterscreened in HepG2.2.15 cells, in which HBeAg is predominantly produced in a cccDNA-independent manner. Following $EC_{50}$ and $CC_{50}$ determinations, confirmed hits were selected and advanced to the measurement of HBV cccDNA by Southern blotting, in which HepDE19 cells were incubated with compound at 10 µM after tetracycline withdrawal, for a total incubation time of 14 days to ensure sufficient cccDNA accumulation. FIG. 1 presents representative data for 2-[benzenesulfonyl-(2-chloro-5-trifluoromethyl-phenyl)-amino]-N-pyridin-4-ylm-ethyl-acetamide. FIG. 4 presents representative data for 4-(benzyl-methyl-sulfamoyl)-N-(2-methyl-benzothiazol-5-yl)-benzamide.

Identification of compounds that inhibits cccDNA accumulation in HepDES19 cells: Compounds were tested on HepDES19 cells, which have a higher level of cccDNA production than HepDE19 cells (Guo, H., D. Jiang, T. Zhou, A. Cuconati, T. M. Block, and J. T. Guo. 2007). Briefly, after withdrawal of tetracycline, HepDES19 cells were left untreated, or were treated with compound at serial concentrations; tetracycline-free media was changed every other day with fresh compound supplementation. The concentration of DMSO in all experimental groups was normalized at 0.1%. The cells were harvested at day 12, viral RNA (top panel), core DNA (middle panel), and Hirt DNA (DP-rcDNA and cccDNA) (bottom panels) were extracted and analyzed by Northern blot and Southern blot, respectively. Shorter exposure of the Hirt DNA blot was used for the quantitative determination of DP-rcDNA signals. Treatment with 2-[benzenesulfonyl-(2-chloro-5-trifluoromethyl-phenyl)-amino]-N-pyridin-4-ylmethyl-acetamide resulted in a dose dependent reduction of cccDNA in HepDES19 cells with the $EC_{50}$ of 10 µM, along with a significant reduction of the putative cccDNA precursor, DP-rcDNA (FIG. 2, bottom panels). The reduction between DP-rcDNA and cccDNA was proportional compared with untreated control. Although cccDNA formation in HepDES19 cells is driven by the transgene-derived pgRNA transcription and DNA replication, the observed slight reduction of viral RNA and DNA replicative intermediates with compound treatment at high concentrations (FIG. 2 top and middle panels) did not quantitatively account for the reduction of cccDNA, and their decrease ought to be a consequence of the reduction of cccDNA, which, once established, contributes approximately 10% of the total viral RNA and DNA production in HBV stable cell lines (Chou, Y. C., K. S. Jeng, M. L. Chen, H. H. Liu, T. L. Liu, Y. L. Chen, Y. C. Liu, C. P. Hu, and C. Chang. 2005. Guo, H., T. Zhou, D. Jiang, A. Cuconati, G. H. Xiao, T. M. Block, and J. T. Guo. 2007. Zhou, T., H. Guo, J. T. Guo, A. Cuconati, A. Mehta, and T. M. Block. 2006).

Treatment with 4-(Benzyl-methyl-sulfamoyl)-N-(2-methyl-benzothiazol-5-yl)-benzamide at concentrations that proved nontoxic to confluent cells resulted in the reduction of cccDNA in HepDES19 cells with the $EC_{50}$ of 3 µM, along with a similar level reduction of the putative cccDNA precursor, DP-rcDNA (FIG. 5, bottom panels). The reduction between DP-rcDNA and cccDNA was proportional compared with untreated control. Although cccDNA formation in HepDES19 cells is driven by the transgene-derived pgRNA transcription and DNA replication, the observed slight reduction of viral RNA and DNA replicative intermediates upon treatment with 4-(Benzyl-methyl-sulfamoyl)-N-(2-methyl-benzothiazol-5-yl)-benzamide at high concentrations (FIG. 5 top and middle panels) did not quantitatively account for the reduction of cccDNA, and their decrease ought to be a consequence of the reduction of cccDNA, which, once established, contributes approximately 10% of the total viral RNA and DNA production in HBV stable cell lines (Chou, Y. C., K. S. Jeng, M. L. Chen, H. H. Liu, T. L. Liu, Y. L. Chen, Y. C. Liu, C. P. Hu, and C. Chang. 2005. Guo, H., T. Zhou, D. Jiang, A. Cuconati, G. H. Xiao, T. M. Block, and J. T. Guo. 2007. Zhou, T., H. Guo, J. T. Guo, A. Cuconati, A. Mehta, and T. M. Block. 2006).

2-[benzenesulfonyl-(2-chloro-5-trifluoromethyl-phenyl)-amino]-N-pyridin-4-ylmethyl-acetamide is not a HBV polymerase inhibitor. The concept that 2-[benzenesulfonyl-(2-chloro-5-trifluoromethyl-phenyl)-amino]-N-pyridin-4-ylmethyl-acetamide directly target cccDNA formation was further supported by the observations that 2-[benzenesulfonyl-(2-chloro-5-trifluoromethyl-phenyl)-amino]-N-pyridin-4-ylmethyl-acetamide did not inhibit HBV polymerase activity in the in vitro endogenous polymerase reaction (FIG. 3), suggesting that 2-[benzenesulfonyl-(2-chloro-5-trifluoromethyl-phenyl)-amino]-N-pyridin-4-ylmethyl-acetamide does not directly target viral polymerase catalyzed DNA replication. In addition, 2-[benzenesulfonyl-(2-chloro-5-trifluoromethyl-phenyl)-amino]-N-pyridin-4-ylmethyl-acetamide did not reduce the steady state levels of HBV RNA and core DNA in HepDES19 cells at an early time point (day 4) of treatment, when the cccDNA was undetectable by Southern blotting. Further, treatment with 2-[benzenesulfonyl-(2-chloro-5-trifluoromethyl-phenyl)-amino]-N-pyridin-4-ylmethyl-acetamide led to a significant reduction of DP-rcDNA at early time point, indicating that HBV rcDNA deproteinization and/or the stability of DP-rcDNA is inhibited by 2-[benzenesulfonyl-(2-chloro-5-trifluoromethyl-phenyl)-amino]-N-pyridin-4-ylmethyl-acetamide. Further analysis demonstrated that 2-[benzenesulfonyl-(2-chloro-5-trifluoromethyl-phenyl)-amino]-N-pyridin-4-ylmethyl-acetamide did not alter the stability of HBV Dp-rcDNA and cccDNA, indicating that 2-[benzenesulfonyl-(2-chloro-5-trifluoromethyl-phenyl)-amino]-N-pyridin-4-ylmethyl-acetamide possess a novel mechanisms to directly inhibit cccDNA biosynthesis.

4-(Benzyl-methyl-sulfamoyl)-N-(2-methyl-benzothiazol-5-yl)-benzamide is not a HBV polymerase inhibitor: The concept that 4-(benzyl-methyl-sulfamoyl)-N-(2-methyl-benzothiazol-5-yl)-benzamide directly target cccDNA formation was further supported by the observations that 4-(benzyl-methyl-sulfamoyl)-N-(2-methyl-benzothiazol-5-yl)-benzamide did not inhibit HBV polymerase activity in the in vitro endogenous polymerase reaction (FIG. 6), suggesting that 4-(Benzyl-methyl-sulfamoyl)-N-(2-methyl-benzothiazol-5-yl)-benzamide does not directly target viral polymerase catalyzed DNA replication. In addition, 4-(Benzyl-methyl-sulfamoyl)-N-(2-methyl-benzothiazol-5-yl)-benzamide did not reduce the steady state levels of HBV RNA and core DNA in HepDES19 cells at an early time point (day 4) of treatment, when the cccDNA was undetectable by Southern blotting. Further, treatment with 4-(benzyl-methyl-sulfamoyl)-N-(2-methyl-benzothiazol-5-yl)-benzamide led to a significant reduction of DP-rcDNA at early time point, indicating that HBV rcDNA deproteinization and/or the stability of DP-rcDNA is inhibited by DSS compound. Further analysis demonstrated that 4-(benzyl-methyl-sulfamoyl)-N-(2-methyl-benzothiazol-5-yl)-benzamide did not alter the stability of HBV Dp-rcDNA and cccDNA, indicating that 4-(benzyl-methyl-sulfamoyl)-N-(2-methyl-benzothiazol-5-yl)-benzamide possess a novel mechanisms to directly inhibit cccDNA biosynthesis.

Results for representative compounds according to the present invention are listed in Table 3.

TABLE 3

Representative examples of compounds of the disclosure and their potencies in cccDNA inhibition assays and cytoxicity assays.

| Entry | Structure | cccDNA inhibition | | $CC_{50}$ ($\mu M$) |
|---|---|---|---|---|
| | | Concentration ($\mu M$) | % Reduction | |
| CCC-0975 | [structure] | 1<br>3<br>10 | 10<br>20<br>70 | >50 |
| CCC-1002-2 | [structure] | 1<br>3<br>10 | 30<br>30<br>90 | >50 |

TABLE 3-continued

Representative examples of compounds of the disclosure and their potencies in cccDNA inhibition assays and cytoxicity assays.

| Entry | Structure | cccDNA inhibition Concentration (μM) | % Reduction | $CC_{50}$ (μM) |
|---|---|---|---|---|
| CCC-1022-3 | | 1<br>3<br>10 | 20<br>50<br>75 | >50 |
| CCC-Lu25-41 | | 3<br>10<br>30 | 10<br>30<br>40 | >50 |
| CCC-Lu25-22 | | 3<br>10<br>30 | 40<br>70<br>70 | >50 |
| IHVR-13102 | | 3<br>10<br>30 | 30<br>80<br>30 | >50 |
| IHVR-13106 | | 1<br>3<br>10 | 0<br>70<br>80 | >50 |

TABLE 3-continued

Representative examples of compounds of the disclosure and their potencies in cccDNA inhibition assays and cytotoxicity assays.

| Entry | Structure | cccDNA inhibition Concentration (μM) | % Reduction | CC$_{50}$ (μM) |
|---|---|---|---|---|
| IHVR-29022 | 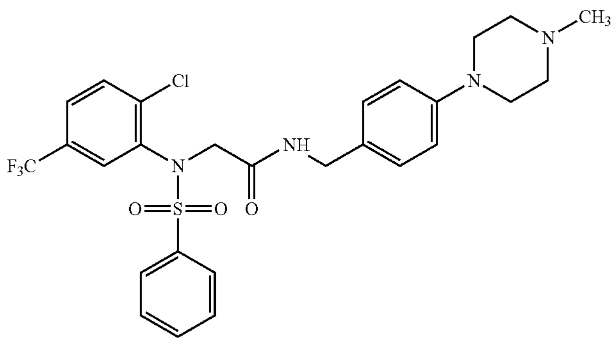 [SMILES: CN1CCN(c2ccc(CNC(=O)CN(c3cc(C(F)(F)F)ccc3Cl)S(=O)(=O)c3ccccc3)cc2)CC1] | 3 | 30 | 49.5 |
| IHVR-29023 | 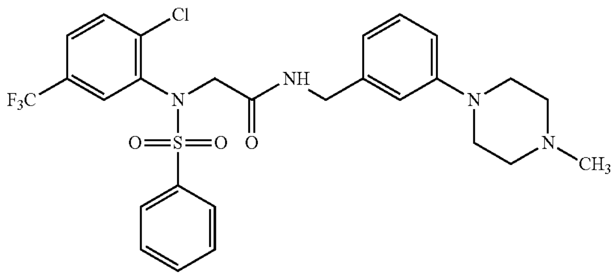 [SMILES: CN1CCN(c2cccc(CNC(=O)CN(c3cc(C(F)(F)F)ccc3Cl)S(=O)(=O)c3ccccc3)c2)CC1] | 3 | 30 | 38.7 |
| CCC-Lu25-51 | 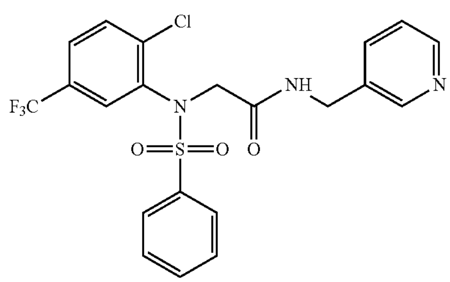 | 3 | 80 | >50 |
| CCC-Lu25-52 | 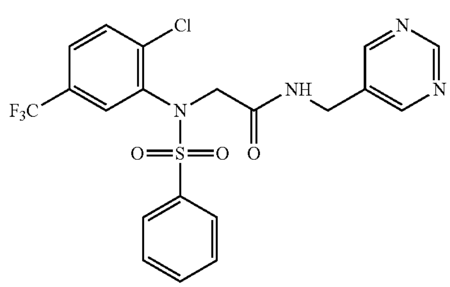 [SMILES: O=C(CN(c1cc(C(F)(F)F)ccc1Cl)S(=O)(=O)c1ccccc1)NCc1cncnc1] | 3 | 80 | >50 |
| CCC-Lu25-53 | 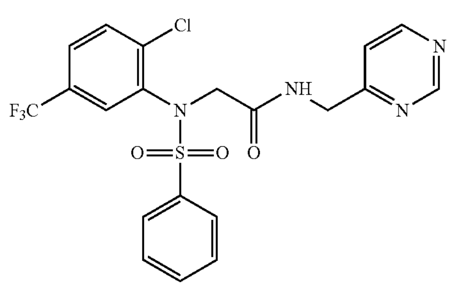 [SMILES: O=C(CN(c1cc(C(F)(F)F)ccc1Cl)S(=O)(=O)c1ccccc1)NCc1ccncn1] | 3 | 70 | >50 |

TABLE 3-continued

Representative examples of compounds of the disclosure and their potencies in cccDNA inhibition assays and cytoxicity assays.

| Entry | Structure | cccDNA inhibition Concentration (μM) | % Reduction | CC$_{50}$ (μM) |
|---|---|---|---|---|
| CCC-Lu25-54 | 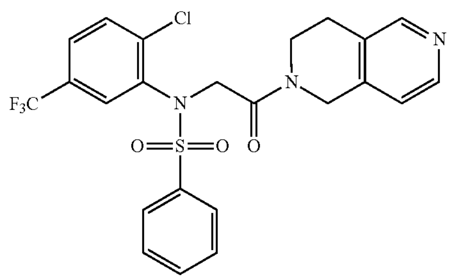 [SMILES: O=C(CN(c1cc(C(F)(F)F)ccc1Cl)S(=O)(=O)c1ccccc1)N1CCc2cnccc2C1] | 3 | 50 | >50 |
| CCC-Lu25-55 | 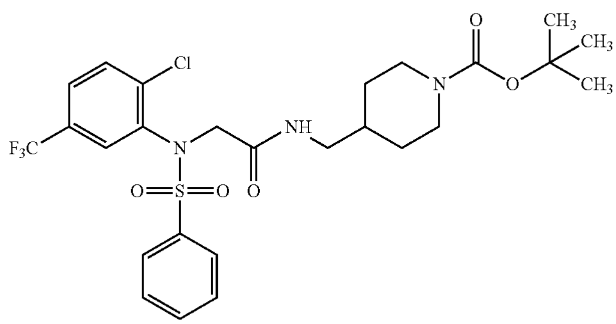 [SMILES: CC(C)(C)OC(=O)N1CCC(CNC(=O)CN(c2cc(C(F)(F)F)ccc2Cl)S(=O)(=O)c2ccccc2)CC1] | 3 | 95 | 19.1 |
| CCC-Lu25-56 | 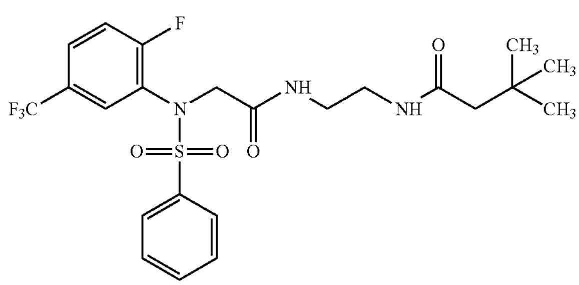 [SMILES: CC(C)(C)CC(=O)NCCNC(=O)CN(c1cc(C(F)(F)F)ccc1F)S(=O)(=O)c1ccccc1] | 3 | 70 | 28.4 |
| CCC-Lu25-61-1 | 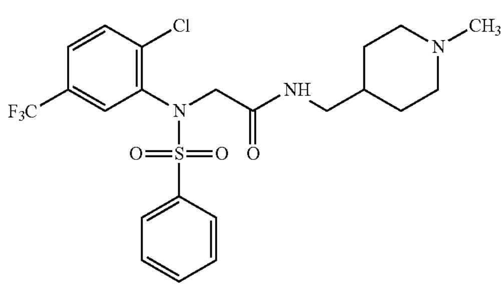 [SMILES: CN1CCC(CNC(=O)CN(c2cc(C(F)(F)F)ccc2Cl)S(=O)(=O)c2ccccc2)CC1] | 3 | 30 | >50 |
| CCC-Lu25-61-2 | 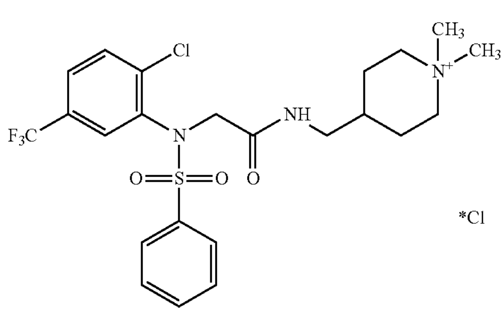 [SMILES: C[N+]1(C)CCC(CNC(=O)CN(c2cc(C(F)(F)F)ccc2Cl)S(=O)(=O)c2ccccc2)CC1] | 3 | 30 | >50 |

TABLE 3-continued
Representative examples of compounds of the disclosure and their potencies in cccDNA inhibition assays and cytoxicity assays.
| Entry | Structure | cccDNA inhibition Concentration (μM) | % Reduction | CC$_{50}$ (μM) |
|---|---|---|---|---|
| CCC-Lu25-20 | 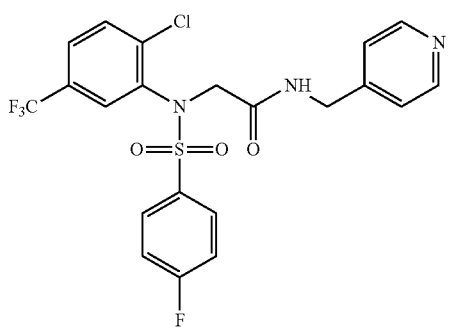 [SMILES: O=C(CN(c1cc(C(F)(F)F)ccc1Cl)S(=O)(=O)c1ccc(F)cc1)NCc1ccncc1] | 3<br>10<br>30 | 20<br>60<br>70 | >50 |
| CCC-Lu25-32 | 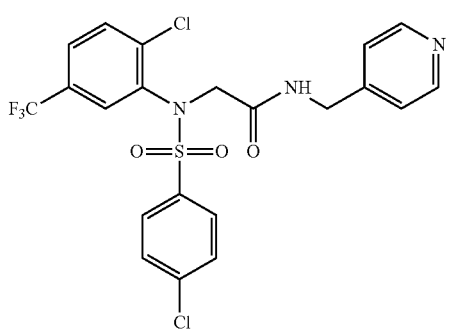 [SMILES: O=C(CN(c1cc(C(F)(F)F)ccc1Cl)S(=O)(=O)c1ccc(Cl)cc1)NCc1ccncc1] | 3<br>10<br>30 | 95<br>95<br>95 | >50 |
| CCC-Lu25-38 | 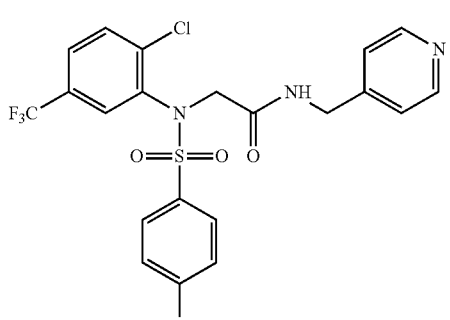 | 3<br>10<br>30 | 95<br>95<br>95 | >50 |
| CCC-Lu25-39 | 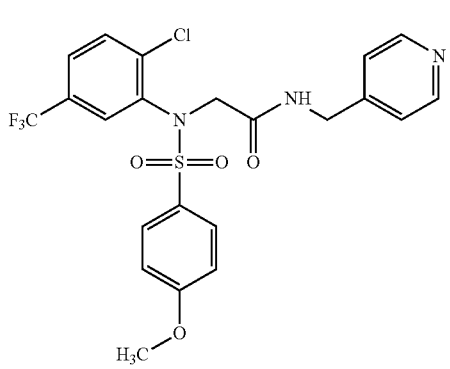 [SMILES: COc1ccc(S(=O)(=O)N(CC(=O)NCc2ccncc2)c2cc(C(F)(F)F)ccc2Cl)cc1] | 3<br>10<br>30 | 95<br>95<br>95 | 49.2 |

TABLE 3-continued

Representative examples of compounds of the disclosure and their potencies in cccDNA inhibition assays and cytoxicity assays.

| Entry | Structure | cccDNA inhibition Concentration (μM) | % Reduction | CC$_{50}$ (μM) |
|---|---|---|---|---|
| CCC-Lu25-42 | 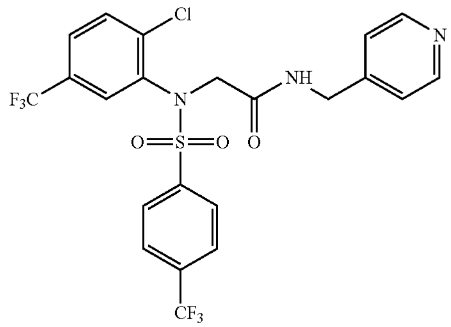 [SMILES: O=C(CN(c1cc(C(F)(F)F)ccc1Cl)S(=O)(=O)c1ccc(C(F)(F)F)cc1)NCc1ccncc1] | 1<br>3<br>10 | 20<br>90<br>95 | >50 |
| CCC-Lu25-50 | 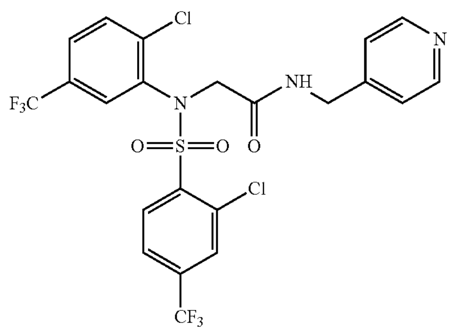 [SMILES: O=C(CN(c1cc(C(F)(F)F)ccc1Cl)S(=O)(=O)c1ccc(C(F)(F)F)cc1Cl)NCc1ccncc1] | 3 | 95 | 30.22 |
| IHVR-13108 | 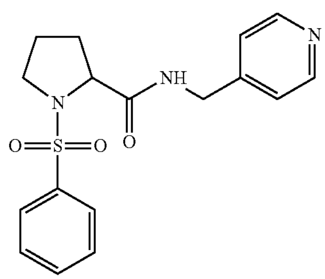 [SMILES: O=C(NCc1ccncc1)C1CCCN1S(=O)(=O)c1ccccc1] | 1<br>3<br>10 | 10<br>70<br>50 | >50 |
| IHVR 13022-1 | 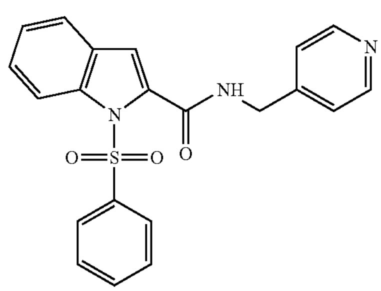 [SMILES: O=C(NCc1ccncc1)c1cc2ccccc2n1S(=O)(=O)c1ccccc1] | 1<br>3<br>10 | 50<br>60<br>65 | >50 |
| CCC-0346 | 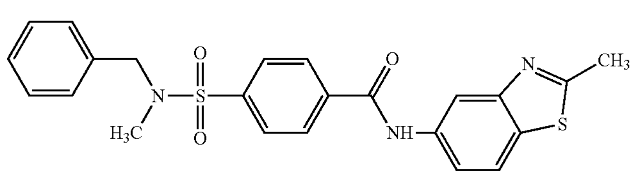 [SMILES: Cc1nc2cc(NC(=O)c3ccc(S(=O)(=O)N(C)Cc4ccccc4)cc3)ccc2s1] | 0.3<br>1<br>3 | 20<br>30<br>60 | 3 |

TABLE 3-continued

Representative examples of compounds of the disclosure and their potencies in cccDNA inhibition assays and cytotoxicity assays.

| Entry | Structure | cccDNA inhibition Concentration (μM) | % Reduction | $CC_{50}$ (μM) |
|---|---|---|---|---|
| IHVR-13006 | | 0.3<br>1<br>3 | 2<br>50<br>50 | 5.9 |
| IHVR-13009 | | 3<br>10<br>30 | 15<br>15<br>30 | >50 |
| IHVR-13004 | | 0.3<br>1<br>3 | 0<br>0<br>50 | 34.1 |
| IHVR-13003-1 | | 3<br>10<br>30 | 3<br>5<br>10 | >50 |

What is claimed is:

1. A compound having formula (Ia):

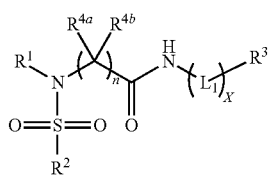

or hydrates, solvates and pharmaceutically acceptable salts thereof, wherein:

(a) $R^1$ is 2-halo-5-trifluoromethyl phenyl;

$R^2$ is selected from the group consisting of substituted phenyl, and optionally substituted heteroaryl; and $R^3$ is selected from the group consisting of optionally substituted phenyl, optionally substituted $C_1$-$C_6$ linear alkyl, optionally substituted $C_1$-$C_6$ branched alkyl, optionally substituted $C_3$-$C_7$ cycloalkyl,

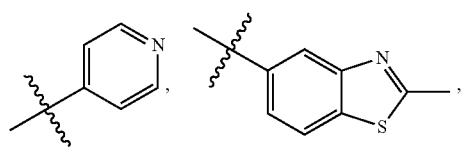

-continued

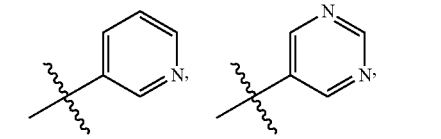

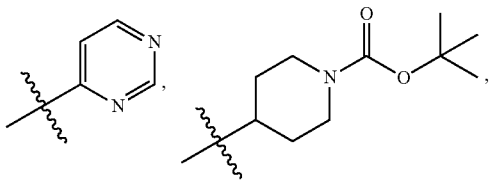

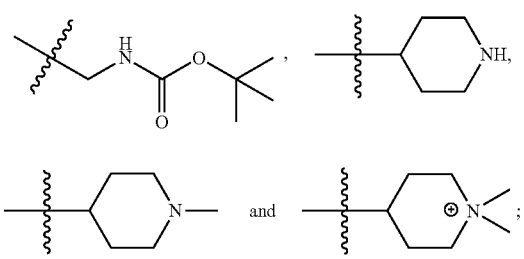

or (b) $R^1$ is 2,5-substituted phenyl, wherein the substituents at the 2-position and 5-position of the phenyl are independently selected from the group consisting of halo and trifluoromethyl;

$R^2$ is phenyl; and
$R^3$ is selected from the group consisting of

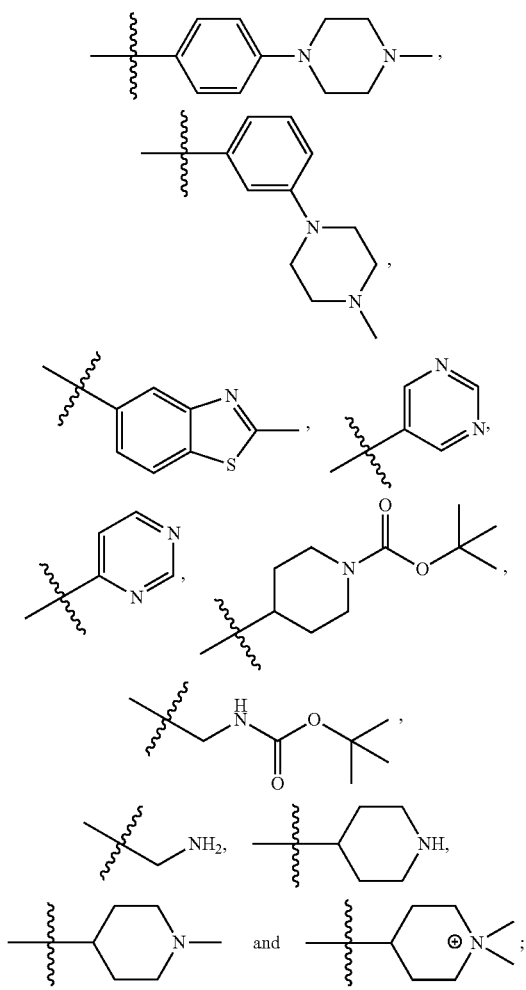

n is 1;
$L^1$ is, independently, $-[C(R^{4a}R^{4b})]_m-$;
m is 1 or 2;
at each occurrence $R^{4a}$ and $R^{4b}$ are each independently selected from a group consisting of hydrogen and methyl; or $R^{4a}$ and $R^{4b}$ are taken together with the carbon atom to which they are bound to form a cyclopropyl ring; and
x is 1.

2. The compound of claim 1 having formula (Ie):

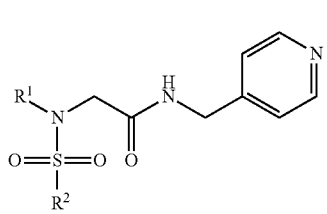

or hydrates, solvates and pharmaceutically acceptable salts thereof.

3. The compound of claim 1 having formula (If) in (a):

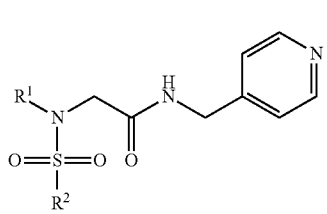

or hydrates, solvates and pharmaceutically acceptable salts thereof.

4. A compound having formula (Ig) in (a):

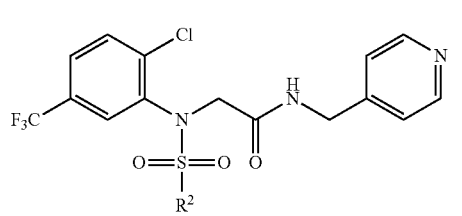

or hydrates, solvates and pharmaceutically acceptable salts thereof.

5. The compound of claim 1 having formula (Ih) in (b):

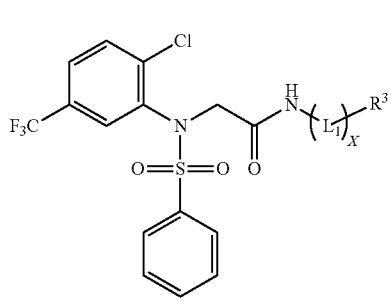

or hydrates, solvates and pharmaceutically acceptable salts thereof.

6. The compound of claim 1, wherein
in (a) $R^1$ is selected from the group consisting of 2-chloro-5-trifluoromethyl-phenyl, 2 bromo-5-trifluoromethyl-phenyl and 2-fluoro-5-trifluoromethyl-phenyl, and
in (b) $R^1$ is selected from the group consisting of 2-chloro-5-trifluoromethyl-phenyl, 2-fluoro-5-chloro-phenyl, 2-bromo-5-trifluoromethyl-phenyl and 2-fluoro-5-trifluoromethyl-phenyl.

7. The compound of claim 1, wherein in (a) $R^2$ is selected from the group consisting of 4-methyl-phenyl, 4-fluoro-phenyl, 4-chloro-phenyl, 4-methoxyphenyl, 4-trifluoromethyl-phenyl and 2-chloro-4-trifluoromethyl-phenyl.

8. The compound of claim 1, wherein in (a) $R^3$ is selected from the group consisting of:

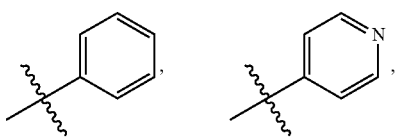

-continued

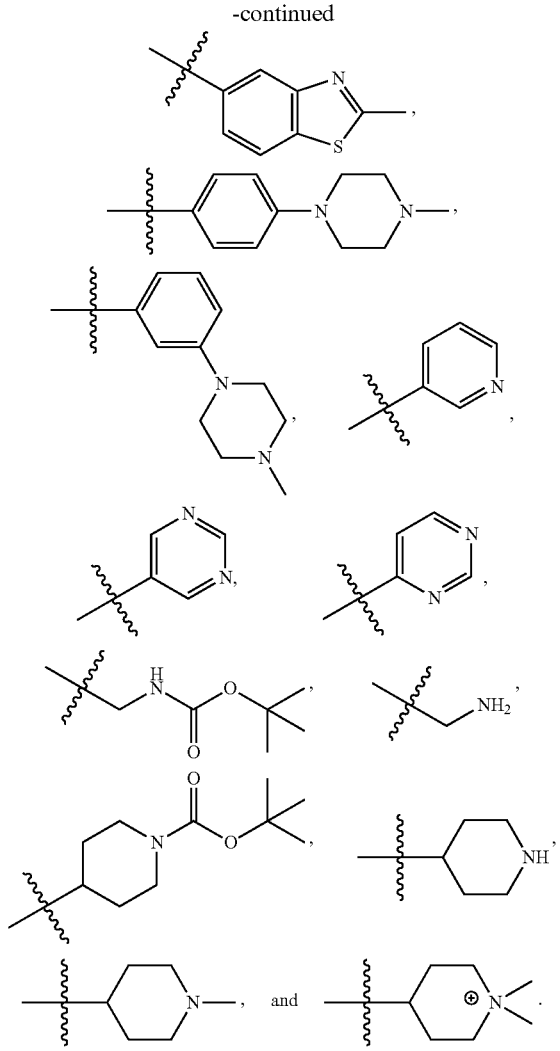

9. The compound of claim 1, wherein in (b) R³ is selected from the group consisting of:

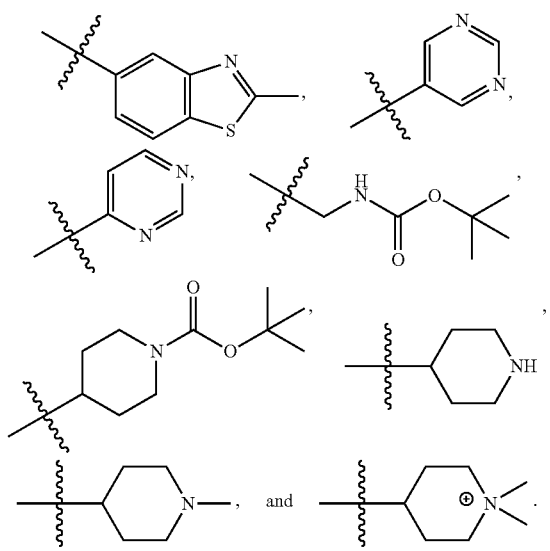

10. A compound selected from the group consisting of:

2-[(2-Chloro-5-trifluoromethyl-phenyl)-(toluene-4-sulfonyl)-amino]-N-pyridin-4-ylmethyl-acetamide

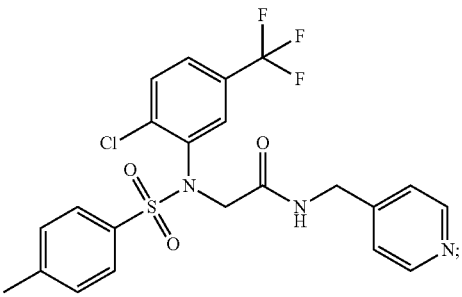 [SMILES: Cc1ccc(S(=O)(=O)N(CC(=O)NCc2ccncc2)c2cc(C(F)(F)F)ccc2Cl)cc1]

2-[(2-Chloro-5-trifluoromethyl-phenyl)-(4-fluoro-benzenesulfonyl)-amino]-N-pyridin-4-ylmethyl-acetamide

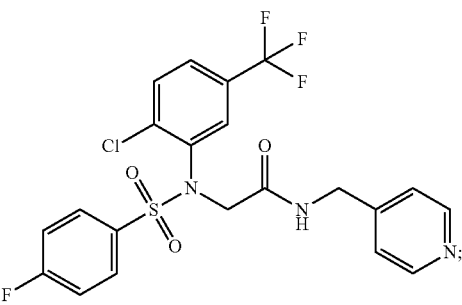 [SMILES: O=C(CN(c1cc(C(F)(F)F)ccc1Cl)S(=O)(=O)c1ccc(F)cc1)NCc1ccncc1]

2-(N-(2-chloro-5-(trifluoromethyl)phenyl) phenyl sulfonamido)-N-(pyridin-4-ylmethyl) propanamide

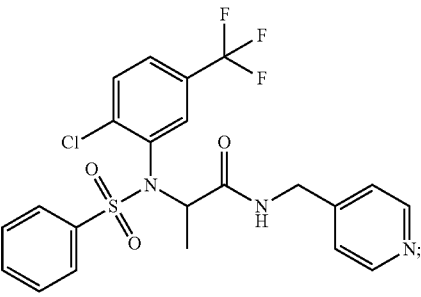 [SMILES: CC(C(=O)NCc1ccncc1)N(c1cc(C(F)(F)F)ccc1Cl)S(=O)(=O)c1ccccc1]

4-(N-(2-chloro-5-(trifluoromethyl)phenyl) phenyl sulfonamido)-N-(pyridin-4-ylmethyl) butanamide

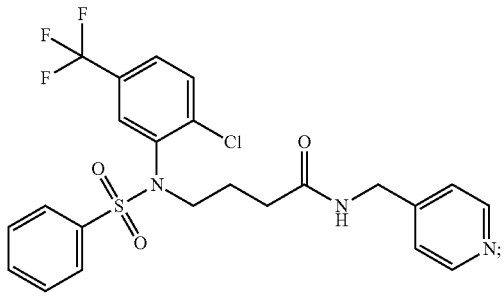 [SMILES: O=C(CCCN(c1cc(C(F)(F)F)ccc1Cl)S(=O)(=O)c1ccccc1)NCc1ccncc1]

87

2-(4-chloro-N-(2-chloro-5-(trifluoromethyl)phenyl) phenylsulfonamido)-N-(pyridin-4-ylmethyl) acetamide

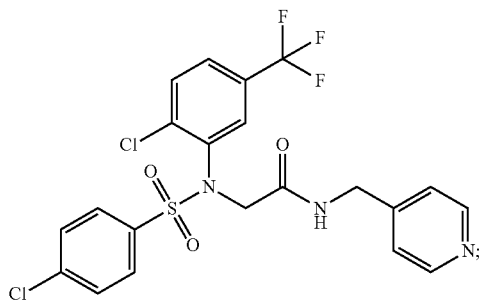 [SMILES: O=C(CN(c1cc(C(F)(F)F)ccc1Cl)S(=O)(=O)c1ccc(Cl)cc1)NCc1ccncc1]

2-(N-(2-chloro-5-(trifluoromethyl)phenyl)-4-methoxyphenylsulfonamido)-N-(pyridin-4-ylmethyl)acetamide

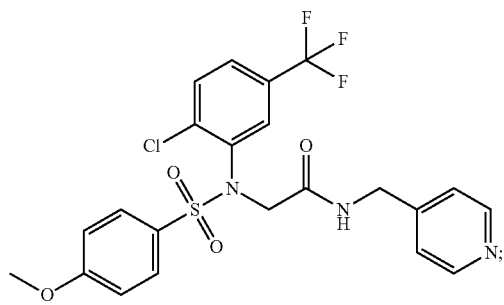 [SMILES: COc1ccc(S(=O)(=O)N(CC(=O)NCc2ccncc2)c2cc(C(F)(F)F)ccc2Cl)cc1]

2-(N-(5-chloro-2-fluorophenyl)phenylsulfonamido)-N-(pyridin-4-ylmethyl)acetamide

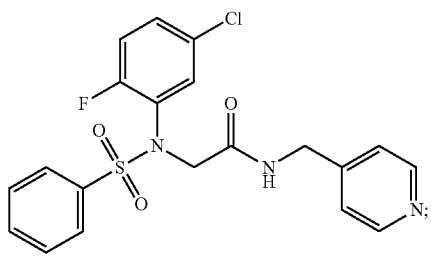 [SMILES: O=C(CN(c1cc(Cl)ccc1F)S(=O)(=O)c1ccccc1)NCc1ccncc1]

2-(N-(2-chloro-5-(trifluoromethyl)phenyl)-4-(trifluoromethyl)phenylsulfonamido)-N-(pyridin-4-ylmethyl)acetamide

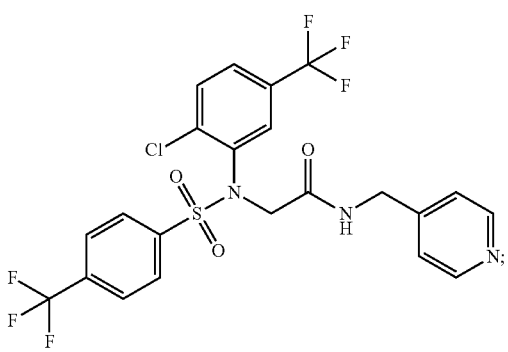 [SMILES: O=C(CN(c1cc(C(F)(F)F)ccc1Cl)S(=O)(=O)c1ccc(C(F)(F)F)cc1)NCc1ccncc1]

88

2-(2-chloro-N-(2-chloro-5-(trifluoromethyl)phenyl)-4-(trifluoromethyl) phenyl sulfonamido)-N-(pyridin-4-ylmethyl)acetamide

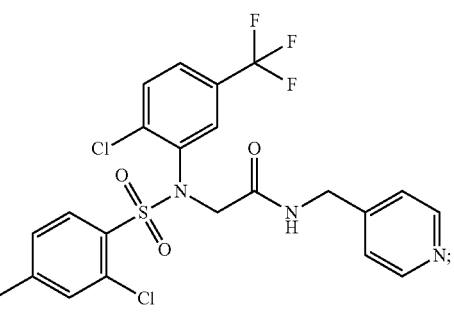

2-(N-(2-chloro-5-(trifluoromethyl)phenyl)phenyl sulfonamido)-N-(pyrimidin-5-ylmethyl) acetamide

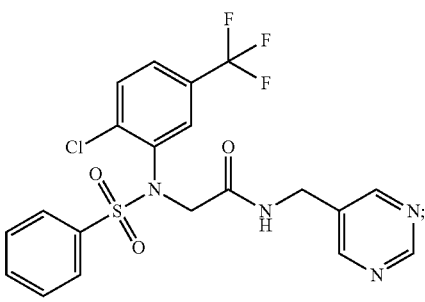 [SMILES: O=C(CN(c1cc(C(F)(F)F)ccc1Cl)S(=O)(=O)c1ccccc1)NCc1cncnc1]

2-(N-(2-chloro-5-(trifluoromethyl)phenyl)phenyl sulfonamido)-N-(pyrimidin-4-ylmethyl) acetamide

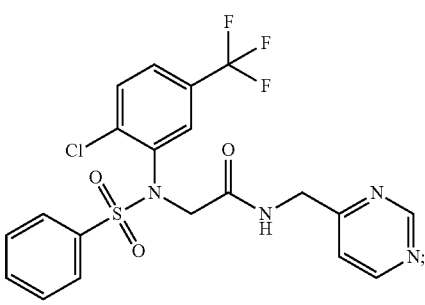 [SMILES: O=C(CN(c1cc(C(F)(F)F)ccc1Cl)S(=O)(=O)c1ccccc1)NCc1ccncn1]

tert-butyl 4-((2-(N-(2-chloro-5-(trifluoromethyl)phenyl) phenylsulfonamido)acetamido) methyl) piperidine-1-carboxylate

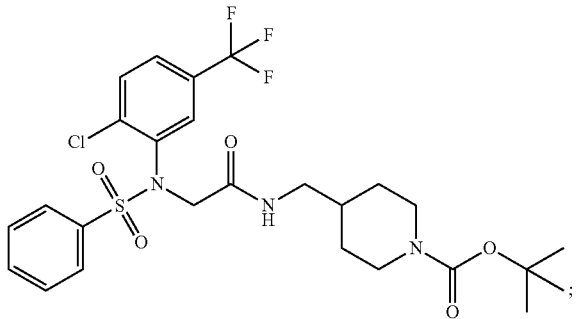 [SMILES: CC(C)(C)OC(=O)N1CCC(CNC(=O)CN(c2cc(C(F)(F)F)ccc2Cl)S(=O)(=O)c2ccccc2)CC1]

| 89 | 90 |
|---|---|
| tert-butyl (2-(2-(N-(2-chloro-5-(trifluoromethyl)phenyl)phenylsulfonamido)acetamido) ethyl)carbamate | 4-((2-(N-(2-chloro-5-(trifluoromethyl)phenyl) phenylsulfonamido)acetamido)methyl)-1,1-dimethylpiperidin-1-ium |

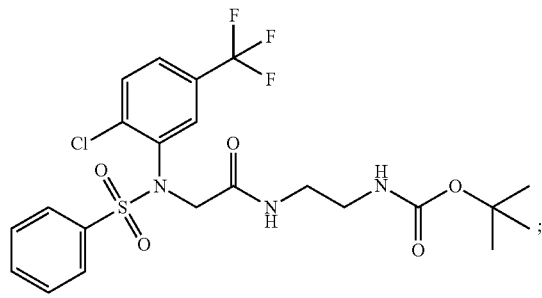 [SMILES: CC(C)(C)OC(=O)NCCNC(=O)CN(c1cc(C(F)(F)F)ccc1Cl)S(=O)(=O)c1ccccc1]

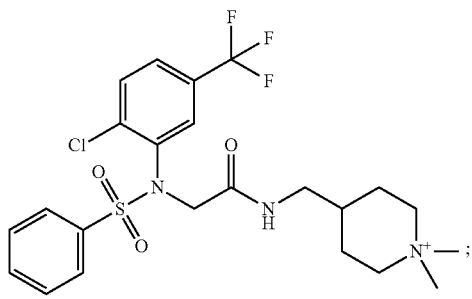

2-(N-(2-chloro-5-(trifluoromethyl)phenyl)phenylsulfonamido)-N-(piperidin-4-ylmethyl) acetamide 2-[Benzenesulfonyl-(2-bromo-5-trifluoromethyl-phenyl)-amino]-N-pyridin-4-ylmethyl-acetamide

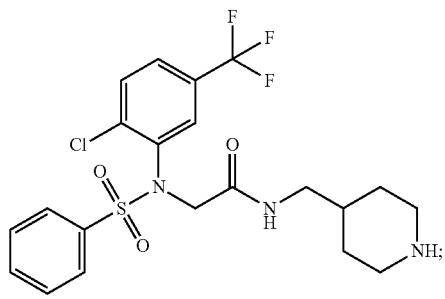 [SMILES: O=C(CN(c1cc(C(F)(F)F)ccc1Cl)S(=O)(=O)c1ccccc1)NCC1CCNCC1]

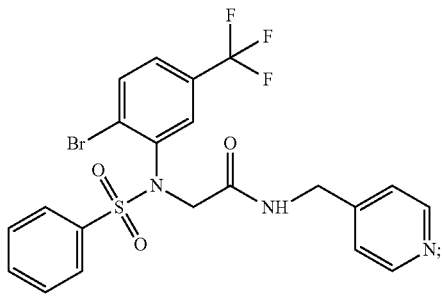

N-(2-aminoethyl)-2-(N-(2-chloro-5-(trifluoromethyl)phenyl)phenylsulfonamido) acetamide 2-[Benzenesulfonyl-(2-fluoro-5-trifluoromethyl-phenyl)-amino]-N-pyridin-4-ylmethyl-acetamide

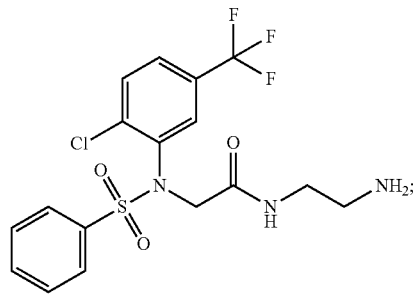 [SMILES: NCCNC(=O)CN(c1cc(C(F)(F)F)ccc1Cl)S(=O)(=O)c1ccccc1]

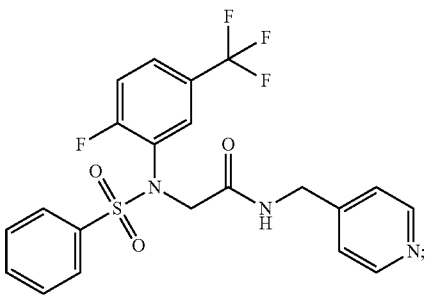

2-(N-(2-chloro-5-(trifluoromethyl)phenyl)phenylsulfonamido)-N-((1-methylpiperidin-4-yl)methyl)acetamide 2-[Benzenesulfonyl-(2-chloro-5-trifluoromethyl-phenyl)-amino]-N-pyridin-4-yl methyl-propionamide

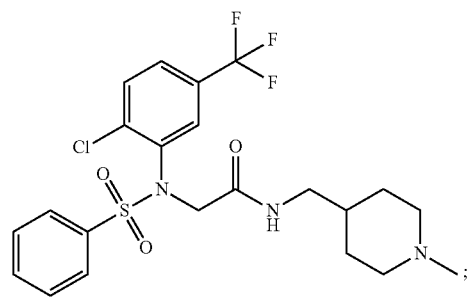 [SMILES: CN1CCC(CNC(=O)CN(c2cc(C(F)(F)F)ccc2Cl)S(=O)(=O)c2ccccc2)CC1]

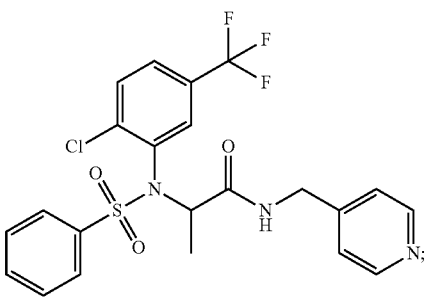 [SMILES: CC(C(=O)NCc1ccncc1)N(c1cc(C(F)(F)F)ccc1Cl)S(=O)(=O)c1ccccc1]

2-[Benzenesulfonyl-(2-chloro-5-trifluoromethyl-phenyl)-amino]-N-(2-methyl-benzothiazol-5-yl)-acetamide

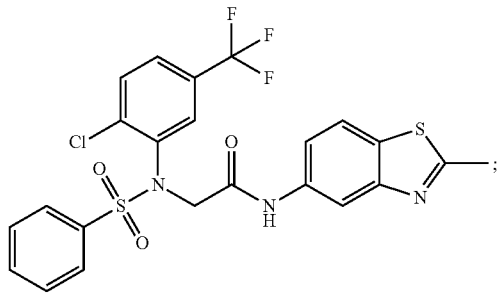 [SMILES: Cc1nc2cc(NC(=O)CN(c3cc(C(F)(F)F)ccc3Cl)S(=O)(=O)c3ccccc3)ccc2s1]

2-[Benzenesulfonyl-(2-chloro-5-trifluoromethyl-phenyl)-amino]-N-[4-(4-methyl-piperazin-1-yl)-benzyl]-acetamide

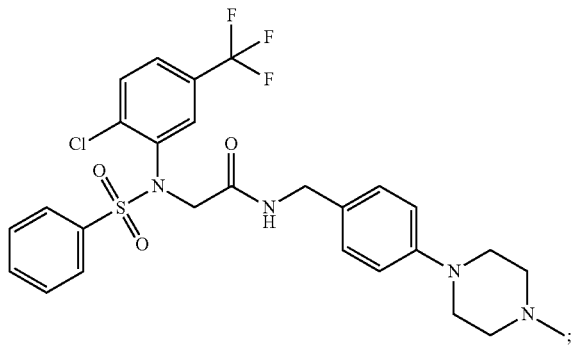 [SMILES: CN1CCN(c2ccc(CNC(=O)CN(c3cc(C(F)(F)F)ccc3Cl)S(=O)(=O)c3ccccc3)cc2)CC1]

2-[Benzenesulfonyl-(2-chloro-5-trifluoromethyl-phenyl)-amino]-N-[3-(4-methyl-piperazin-1-yl)-benzyl]-acetamide

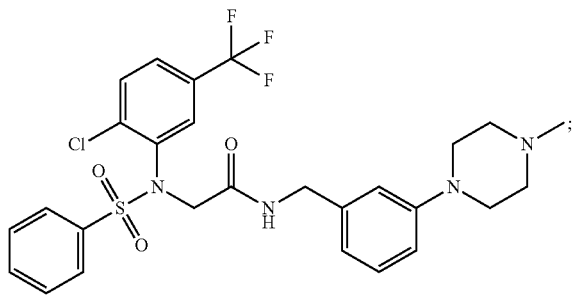 [SMILES: CN1CCN(c2cccc(CNC(=O)CN(c3cc(C(F)(F)F)ccc3Cl)S(=O)(=O)c3ccccc3)c2)CC1]

and a pharmaceutically acceptable form thereof.

11. A pharmaceutical composition comprising at least one compound according to claim 1 and at least one pharmaceutically acceptable excipient.

12. A pharmaceutical composition comprising at least one compound according to claim 2 and at least one pharmaceutically acceptable excipient.

13. A pharmaceutical composition comprising at least one compound according to claim 3 and at least one pharmaceutically acceptable excipient.

14. A pharmaceutical composition comprising at least one compound according to claim 4 and at least one pharmaceutically acceptable excipient.

15. A pharmaceutical composition comprising at least one compound according to claim 5 and at least one pharmaceutically acceptable excipient.

16. A pharmaceutically acceptable composition comprising at least one pharmaceutically acceptable excipient and at least one compound selected from the group consisting of:
2-[Benzenesulfonyl-(2-chloro-5-trifluoromethyl-phenyl)-amino]-N-pyridin-4-ylmethyl-acetamide;
2-[(2-Chloro-5-trifluoromethyl-phenyl)-(toluene-4-sulfonyl)-amino]-N-pyridin-4-ylmethyl-acetamide;
2-[(2-Chloro-5-trifluoromethyl-phenyl)-(4-fluoro-benzenesulfonyl)-amino]-N-pyridin-4-ylmethyl-acetamide;
2-(N-(2-chloro-5-(trifluoromethyl)phenyl) phenylsulfonamido)-N-(pyridin-4-ylmethyl) propanamide;
4-(N-(2-chloro-5-(trifluoromethyl)phenyl) phenylsulfonamido)-N-(pyridin-4-ylmethyl) butanamide;
2-(4-chloro-N-(2-chloro-5-(trifluoromethyl)phenyl)phenylsulfonamido)-N-(pyridin-4-ylmethyl)acetamide;
2-(N-(2-chloro-5-(trifluoromethyl)phenyl)-4-methoxyphenylsulfonamido)-N-(pyridin-4-ylmethyl)acetamide;
2-(N-(5-chloro-2-fluorophenyl)phenylsulfonamido)-N-(pyridin-4-ylmethyl)acetamide;
2-(N-(2-chloro-5-(trifluoromethyl)phenyl)-4-(trifluoromethyl)phenylsulfonamido)-N-(pyridin-4-ylmethyl)acetamide;
2-(2-chloro-N-(2-chloro-5-(trifluoromethyl)phenyl)-4-(trifluoromethyl) phenylsulfonamido)-N-(pyridin-4-ylmethyl)acetamide;
2-(N-(2-chloro-5-(trifluoromethyl)phenyl)phenyl sulfonamido)-N-(pyridin-3-ylmethyl) acetamide;
2-(N-(2-chloro-5-(trifluoromethyl)phenyl)phenyl sulfonamido)-N-(pyrimidin-5-ylmethyl) acetamide;
2-(N-(2-chloro-5-(trifluoromethyl)phenyl)phenyl sulfonamido)-N-(pyrimidin-4-ylmethyl) acetamide;
tert-butyl 4-((2-(N-(2-chloro-5-(trifluoromethyl)phenyl) phenylsulfonamido)acetamido) methyl) piperidine-1-carboxylate;
tert-butyl (2-(2-(N-(2-chloro-5-(trifluoromethyl)phenyl) phenylsulfonamido)acetamido) ethyl)carbamate;
2-(N-(2-chloro-5-(trifluoromethyl)phenyl)phenylsulfonamido)-N-(piperidin-4-ylmethyl) acetamide;
N-(2-aminoethyl)-2-(N-(2-chloro-5-(trifluoromethyl) phenyl)phenylsulfonamido) acetamide;
2-(N-(2-chloro-5-(trifluoromethyl)phenyl)phenylsulfonamido)-N-((1-methylpiperidin-4-yl)methyl)acetamide;
4-((2-(N-(2-chloro-5-(trifluoromethyl)phenyl) phenylsulfonamido)acetamido)methyl)-1,1-dimethylpiperidin-1-ium chloride;
2-[Benzenesulfonyl-(2-bromo-5-trifluoromethyl-phenyl)-amino]-N-pyridin-4-ylmethyl-acetamide;
2-[Benzenesulfonyl-(2-fluoro-5-trifluoromethyl-phenyl)-amino]-N-pyridin-4-ylmethyl-acetamide;
2-[Benzenesulfonyl-(2-chloro-5-trifluoromethyl-phenyl)-amino]-N-pyridin-4-ylmethyl-propionamide;
2-[Benzenesulfonyl-(2-chloro-5-trifluoromethyl-phenyl)-amino]-N-(2-methyl-benzothiazol-5-yl)-acetamide;
2-[Benzenesulfonyl-(2-chloro-5-trifluoromethyl-phenyl)-amino]-N-benzyl-acetamide;
2-[Benzenesulfonyl-(2-chloro-5-trifluoromethyl-phenyl)-amino]-N-[4-(4-methyl-piperazin-1-yl)-benzyl]-acetamide;
2-[Benzenesulfonyl-(2-chloro-5-trifluoromethyl-phenyl)-amino]-N-[3-(4-methyl-piperazin-1-yl)-benzyl]-acetamide;
and a pharmaceutically acceptable form thereof.

17. A method of treating a disease associated with covalently closed circular DNA formation, said method comprising administering to a subject an effective amount of at least one compound according to the claim 1 to treat the disease.

18. The method of claim 17, wherein the at least one compound is administered in a composition further comprising at least one pharmaceutically acceptable excipient.

19. A method of treating a disease associated with covalently closed circular DNA formation, said method comprising administering to a subject an effective amount of at least one compound according to the claim 2 to treat the disease.

20. The method of claim 19, wherein the at least one compound is administered in a composition further comprising at least one pharmaceutically acceptable excipient.

21. A method of treating a disease associated with covalently closed circular DNA formation, said method comprising administering to a subject an effective amount of at least one compound according to the claim 3 to treat the disease.

22. The method of claim 21, wherein the at least one compound is administered in a composition further comprising at least one pharmaceutically acceptable excipient.

23. A method of treating a disease associated with covalently closed circular DNA formation, said method comprising administering to a subject an effective amount of at least one compound according to the claim 4 to treat the disease.

24. The method of claim 23, wherein the at least one compound is administered in a composition further comprising at least one pharmaceutically acceptable excipient.

25. A method of treating a disease associated with covalently closed circular DNA formation, said method comprising administering to a subject an effective amount of at least one compound according to the claim 5 to treat the disease.

26. The method of claim 25, wherein the at least one compound is administered in a composition further comprising at least one pharmaceutically acceptable excipient.

27. A method of treating a disease associated with covalently closed circular DNA formation, said method comprising administering to a subject an effective amount of at least one compound selected from the group consisting of:
- 2-[Benzenesulfonyl-(2-chloro-5-trifluoromethyl-phenyl)-amino]-N-pyridin-4-ylmethyl-acetamide;
- 2-[(2-Chloro-5-trifluoromethyl-phenyl)-(toluene-4-sulfonyl)-amino]-N-pyridin-4-ylmethyl-acetamide;
- 2-[(2-Chloro-5-trifluoromethyl-phenyl)-(4-fluoro-benzenesulfonyl)-amino]-N-pyridin-4-ylmethyl-acetamide;
- 2-(N-(2-chloro-5-(trifluoromethyl)phenyl) phenyl sulfonamido)-N-(pyridin-4-ylmethyl)propanamide;
- 4-(N-(2-chloro-5-(trifluoromethyl)phenyl) phenyl sulfonamido)-N-(pyridin-4-ylmethyl)butanamide;
- 2-(4-chloro-N-(2-chloro-5-(trifluoromethyl)phenyl) phenyl sulfonamido)-N-(pyridin-4-ylmethyl)acetamide;
- 2-(N-(2-chloro-5-(trifluoromethyl)phenyl)-4-methoxyphenylsulfonamido)-N-(pyridin-4-ylmethyl)acetamide;
- 2-(N-(5-chloro-2-fluorophenyl)phenylsulfonamido)-N-(pyridin-4-ylmethyl)acetamide;
- 2-(N-(2-chloro-5-(trifluoromethyl)phenyl)-4-(trifluoromethyl)phenylsulfonamido)-N-(pyridin-4-ylmethyl)acetamide;
- 2-(2-chloro-N-(2-chloro-5-(trifluoromethyl)phenyl)-4-(trifluoromethyl) phenylsulfonamido)-N-(pyridin-4-ylmethyl)acetamide;
- 2-(N-(2-chloro-5-(trifluoromethyl)phenyl)phenyl sulfonamido)-N-(pyridin-3-ylmethyl)acetamide;
- 2-(N-(2-chloro-5-(trifluoromethyl)phenyl)phenyl sulfonamido)-N-(pyrimidin-5-ylmethyl)acetamide;
- 2-(N-(2-chloro-5-(trifluoromethyl)phenyl)phenyl sulfonamido)-N-(pyrimidin-4-ylmethyl)acetamide;
- tert-butyl 4-((2-(N-(2-chloro-5-(trifluoromethyl)phenyl) phenylsulfonamido)acetamido) methyl) piperidine-1-carboxylate;
- tert-butyl (2-(2-(N-(2-chloro-5-(trifluoromethyl)phenyl) phenylsulfonamido)acetamido) ethyl)carbamate;
- 2-(N-(2-chloro-5-(trifluoromethyl)phenyl)phenylsulfonamido)-N-(piperidin-4-ylmethyl) acetamide;
- N-(2-aminoethyl)-2-(N-(2-chloro-5-(trifluoromethyl) phenyl)phenylsulfonamido) acetamide;
- 2-(N-(2-chloro-5-(trifluoromethyl)phenyl)phenylsulfonamido)-N-((1-methylpiperidin-4-yl)methyl)acetamide;
- 4-((2-(N-(2-chloro-5-(trifluoromethyl)phenyl) phenylsulfonamido)acetamido)methyl)-1,1-dimethylpiperidin-1-ium chloride;
- 2-[Benzenesulfonyl-(2-bromo-5-trifluoromethyl-phenyl)-amino]-N-pyridin-4-ylmethyl-acetamide;
- 2-[Benzenesulfonyl-(2-fluoro-5-trifluoromethyl-phenyl)-amino]-N-pyridin-4-ylmethyl-acetamide;
- 2-[Benzenesulfonyl-(2-chloro-5-trifluoromethyl-phenyl)-amino]-N-pyridin-4-ylmethyl-propionamide;
- 2-[Benzenesulfonyl-(2-chloro-5-trifluoromethyl-phenyl)-amino]-N-(2-methyl-benzothiazol-5-yl)-acetamide;
- 2-[Benzenesulfonyl-(2-chloro-5-trifluoromethyl-phenyl)-amino]-N-benzyl-acetamide;
- 2-[Benzenesulfonyl-(2-chloro-5-trifluoromethyl-phenyl)-amino]-N-[4-(4-methyl-piperazin-1-yl)-benzyl]-acetamide;
- 2-[Benzenesulfonyl-(2-chloro-5-trifluoromethyl-phenyl)-amino]-N-[3-(4-methyl-piperazin-1-yl)-benzyl]-acetamide;

and a pharmaceutically acceptable form thereof.

28. The method of claim 17, wherein the disease is hepatitis B.

29. The method of claim 19, wherein the disease is hepatitis B.

30. The method of claim 21, wherein the disease is hepatitis B.

31. The method of claim 23, wherein the disease is hepatitis B.

32. The method of claim 25, wherein the disease is hepatitis B.

33. The method of claim 27, wherein the disease is hepatitis B.

* * * * *